(12) United States Patent
Buettelmann et al.

(10) Patent No.: US 7,943,619 B2
(45) Date of Patent: May 17, 2011

(54) ISOXAZOLO-PYRIDAZINE DERIVATIVES

(75) Inventors: Bernd Buettelmann, Schopfheim (DE);
Roland Jakob-Roetne, Inzlingen (DE);
Henner Knust, Rheinfelden (DE);
Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 233 days.

(21) Appl. No.: 12/277,331

(22) Filed: Nov. 25, 2008

(65) Prior Publication Data
US 2009/0143385 A1 Jun. 4, 2009

(30) Foreign Application Priority Data

Dec. 4, 2007 (EP) .................................. 07122293

(51) Int. Cl.
C07D 417/12 (2006.01)
A61K 31/501 (2006.01)
A61P 25/28 (2006.01)

(52) U.S. Cl. .................... 514/252.05; 544/238
(58) Field of Classification Search ................ 544/238; 514/252.05
See application file for complete search history.

(56) References Cited

U.S. PATENT DOCUMENTS

| 4,639,266 | A | 1/1987 | Heubach et al. |
| 2003/0055085 | A1 | 3/2003 | Wagener et al. |
| 2004/0006226 | A1 | 1/2004 | Ladduwahetty et al. |
| 2010/0144744 | A1* | 6/2010 | Li et al. ............ 514/249 |

FOREIGN PATENT DOCUMENTS

| DE | 3525205 | 3/1986 |
| GB | 2336589 | 10/1999 |
| JP | 2007/230909 | 9/2007 |
| WO | WO 01/029015 | 4/2001 |
| WO | WO 01/34603 | 5/2001 |
| WO | WO 02/50062 A2 | 6/2002 |
| WO | WO 02/081474 A1 | 10/2002 |
| WO | WO 03/004027 | 1/2003 |
| WO | WO 03/015771 | 2/2003 |
| WO | WO 03/044017 | 5/2003 |
| WO | WO 2004/048349 | 6/2004 |
| WO | WO 2005/014553 | 2/2005 |
| WO | WO 2005/118568 | 12/2005 |
| WO | WO 2005/123672 A2 | 12/2005 |
| WO | WO 2006/037480 | 4/2006 |
| WO | WO 2006/044617 | 4/2006 |
| WO | WO 2006/069155 | 6/2006 |
| WO | WO 2008025539 | * 8/2006 |
| WO | WO 2006/095822 | 9/2006 |
| WO | WO 2007/009275 | 1/2007 |
| WO | WO 2007/039389 | 4/2007 |
| WO | WO 2007/052843 | 5/2007 |
| WO | WO 2007/076260 | 7/2007 |
| WO | WO 2008/025539 | 3/2008 |
| WO | WO 2008/025540 | 3/2008 |

OTHER PUBLICATIONS

McNamara et al., Psychobiology (1993), vol. 21, pp. 101-108.
Goodman et al., Tetrahedron (1999) vol. 55 pp. 15067-15070.
Abstract corresponding to JP 2007/230909 (Document B8).
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Seydel et al., J. Med. Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.
Database Caplus, chemical Abstracts Service XP002514136, 2006.

* cited by examiner

*Primary Examiner* — James O Wilson
*Assistant Examiner* — Cecilia M Jaisle
(74) *Attorney, Agent, or Firm* — George W. Johnston; Patricia S. Rocha-Tramaloni; Kimberly J. Prior

(57) ABSTRACT

The invention relates to isoxazolo-pyridazine compounds, in particular those of formula I as described above and to a pharmaceutically acceptable salts thereof, having affinity and selectivity for the GABA A α5 receptor binding site, their manufacture, pharmaceutical compositions containing them and their use as cognitive enhancers or for the treatment of cognitive disorders like Alzheimer's disease.

15 Claims, No Drawings

ISOXAZOLO-PYRIDAZINE DERIVATIVES

PRIORITY TO RELATED APPLICATION(S)

This application claims the benefit of European Patent Application No. 07122293.9, filed Dec. 4, 2007, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex is a membrane-bound heteropentameric protein polymer composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhances spatial learning in the Morris water-maze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without pro-convulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides isoxazolo-pyridazine derivatives having affinity and selectivity for the GABA A α5 receptor binding site, their manufacture, pharmaceutical compositions containing them and their use as cognitive enhancers or for the treatment of cognitive disorders like Alzheimer's disease.

In particular, the present invention provides with isoxazolo-pyridazine derivatives of formula I

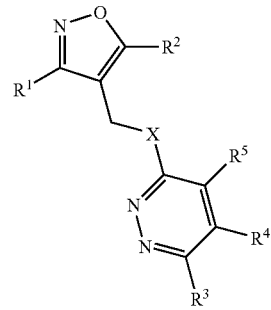

wherein $R^1$ to $R^5$ and X are as described in claim 1.

The most preferred indication in accordance with the present invention is Alzheimer's disease

DETAILED DESCRIPTION OF THE INVENTION

The following definitions of the general terms used in the present description apply irrespective of whether the terms in question appear alone or in combination.

As used herein, the term "alkyl" denotes a saturated straight- or branched-chain hydrocarbon group containing from 1 to 7 carbon atoms, for example, methyl, ethyl, propyl, isopropyl, n-butyl, iso-butyl, sec-butyl, tert-butyl and the like. Preferred alkyl groups are groups with 1 to 4 carbon atoms.

The term "halo" or "halogen" denotes chloro, iodo, fluoro and bromo.

The term "halo-$C_{1-7}$-alkyl", "$C_{1-7}$-haloalkyl" or "$C_{1-7}$-alkyl optionally substituted with halo" denotes a $C_{1-7}$-alkyl group as defined above wherein at least one of the hydrogen atoms of the alkyl group is replaced by a halogen atom, preferably fluoro or chloro, most preferably fluoro. Examples of halo-$C_{1-7}$-alkyl include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro, as well as those groups specifically illustrated by the examples herein below. Among the preferred halo-$C_{1-7}$-alkyl groups are difluoro- or trifluoro-methyl or -ethyl.

The term "hydroxy-$C_{1-7}$-alkyl", "$C_{1-7}$-hydroxyalkyl" or "$C_{1-7}$-alkyl optionally substituted with hydroxy" denotes a $C_{1-7}$-alkyl group as defined above wherein at least one of the hydrogen atoms of the alkyl group is replaced by a hydroxy group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more hydroxy group(s), in particular with one, two or three hydroxy groups, preferably with one hydroxy group, as well as those groups specifically illustrated by the examples herein below.

The term "cyano-$C_{1-7}$-alkyl", "$C_{1-7}$-cyanoalkyl" or "$C_{1-7}$-alkyl optionally substituted with cyano" denotes a $C_{1-7}$-alkyl group as defined above wherein at least one of the hydrogen atoms of the alkyl group is replaced by a cyano group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more cyano group(s), preferably by one, two or three, and more preferably by one cyano group, as well as those groups specifically illustrated by the examples herein below.

The term "alkoxy" denotes a group —O—R wherein R is alkyl as defined above.

The term "aryl" refers to a monovalent aromatic carbocyclic ring system, preferably to phenyl or naphthyl, and more preferably to phenyl. Aryl is optionally substituted as described herein.

The term "aromatic" means aromatic according to Hückel's rule. A cyclic molecule follows Hückel's rule when the number of its π-electrons equals 4n+2 where n is zero or any positive integer.

The term "$C_{1-7}$-haloalkoxy" or "halo-$C_{1-7}$-alkoxy" denotes a $C_{1-7}$-alkoxy group as defined above wherein at least one of the hydrogen atoms of the alkoxy group is replaced by a halogen atom, preferably fluoro or chloro, most preferably fluoro. Examples of halo-$C_{1-7}$-alkoxy include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro atoms, as well as those groups specifically illustrated by the examples herein below. Among the preferred halo-$C_{1-7}$-alkoxy groups are difluoro- or trifluoro-methoxy or -ethoxy substituted as described above, preferably —$OCF_3$.

The term "cycloalkyl" refers to a monovalent saturated cyclic hydrocarbon radical of 3 to 7 ring carbon atoms, preferably 3 to 6 carbon atoms, such as cyclopropyl, cyclobutyl, cyclopentyl, or cyclohexyl.

The term "heterocycloalkyl" refers to a monovalent 3 to 7 membered saturated monocyclic ring containing one, two or three ring heteroatoms selected from N, O and S. One or two ring heteroatoms are preferred. Preferred are 4 to 6 membered heterocycloalkyl or 5 to 6 membered heterocycloalkyl, each containing one or two ring heteroatoms selected from N, O and S. "Heterocycloalkyl" is hence a subgroup of "heterocyclyl" as defined below. Examples for heterocycloalkyl moieties are tetrahydrofuranyl, tetrahydropyranyl, pyrrolidinyl, morpholinyl, thiomorpholinyl, 1,1-dioxo-thiomorpholinyl, piperidinyl, or piperazinyl. Preferred heterocycloalkyl are tetrahydropyranyl, pyrrolidinyl, morpholinyl, or thiomorpholinyl. Heterocycloalkyl is optionally substituted as described herein.

The term "heteroaryl" refers to a monovalent aromatic 5- or 6-membered monocyclic ring containing one, two, or three ring heteroatoms selected from N, O, and S, the remaining ring atoms being C. Preferably, the 5- or 6-membered heteroaryl ring contains one or two ring heteroatoms. 6-membered heteroaryl are preferred. Examples for heteroaryl moieties include but are not limited to furanyl, thiophenyl, pyridinyl, pyrimidinyl, pyrazinyl, pyrazolyl, imidazolyl, oxazolyl, isoxazolyl, thiazolyl, isothiazolyl, triazolyl, 1,2,4-oxadiazolyl, or 1,3,4-oxadiazolyl. Preferred heteroaryl groups are furanyl, pyrazolyl, or isoxazolyl.

The term "heterocyclyl" or "heterocyclyl moiety" refers to a monovalent saturated or partially saturated 3- to 7-membered monocyclic or 9- to 10-membered bicyclic ring system wherein one, two, three or four ring carbon atoms have been replaced by N, O or S, and with the attachment point on the saturated or partially unsaturated ring of said ring system. Such bicyclic heterocyclyl moieties hence include aromatic rings annelated to saturated rings. Where applicable, "heterocyclyl moiety" further includes cases where two residues R' and R" together with the nitrogen to which they are bound form such a heterocyclyl moiety. Examples for heterocyclyl include but are not limited to tetrahydropyridinyl, oxetanyl, isoxazolidinyl, dihydropyridazinyl, tetrahydrofuranyl, tetrahydropyranyl, tetrahydrothiopyranyl, piperidinyl, piperazinyl, pyrrolidinyl, morpholinyl, or thiomorpholinyl. Preferred heterocyclyl are tetrahydropyranyl, pyrrolidinyl, morpholinyl, thiomorpholinyl or 1,1-dioxo-thiomorpholinyl. Heterocyclyl is optionally substituted as described herein. Examples for substituted heterocyclyl include, but are not limited to pyrrolidinonyl or dioxothiomorpholinyl.

The term "oxo" when referring to substituents on heterocycloalkyl, heterocyclyl or on a heterocycle means that an oxygen atom is attached to the ring. Thereby, the "oxo" may either replace two hydrogen atoms on a carbon atom, or it may simply be attached to sulfur, so that the sulfur exists in oxidized form, i.e. bearing one or two oxygens.

When indicating the number of substituents, the term "one or more" means from one substituent to the highest possible number of substitution, i.e. replacement of one hydrogen up to replacement of all hydrogens by substituents. Thereby, one, two or three substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

In detail, the present invention relates to compounds of the general formula (I)

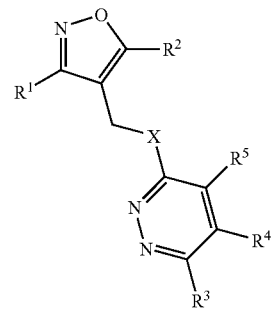

I wherein
X is O or NH;
$R^1$ is phenyl, pyridinyl, or pyrimidinyl each optionally substituted with one, two or three halo,
$R^2$ is $C_{1-4}$alkyl, H or $C_{1-4}$haloalkyl;
$R^3$, $R^4$, and $R^5$ each are independently
  H,
  $C_{1-7}$alkyl, optionally substituted with one or more halo, cyano, or hydroxy,
  $C_{1-7}$alkoxy, optionally substituted with one or more halo,
  CN,
  halo,
  $NO_2$,
  —C(O)—$R^a$, wherein $R^a$ is hydroxy, $C_{1-7}$alkoxy, $C_{1-7}$alkyl, phenoxy or phenyl,
  —$NR^bR^c$, wherein $R^b$ and $R^c$ are each independently
    hydrogen,
    $C_{1-7}$alkyl,
    —C(O)$C_{1-7}$alkyl, optionally substituted with one or more halo,
    —C(O)($CH_2$)$_m$—O—$C_{1-7}$alkyl, wherein m is 0, 1, 2, 3, 4, 5 or 6, —C(O)C(O)OC$_{1-7}$-alkyl,
—C(O)CH$_2$C(O)OC$_{1-7}$-alkyl,
—C(O)R$^i$, wherein R$^i$ is phenyl or 5- to 6-membered heteroaryl, each optionally substituted with one or more E,
—C(O)—C$_{3-7}$cycloalkyl, optionally substituted with one or more B,
—C(O)—R$^{ii}$, wherein R$^{ii}$ is 3- to 7-membered heterocyclyl, optionally substituted by one or more A,
3- to 7-membered heterocyclyl, optionally substituted with one or more A,
5- or 6-membered heteroaryl, optionally substituted with one or more E,
—C(O)—NR$^d$R$^e$, wherein R$^d$ and R$^e$ are each independently
H,
C$_{1-7}$alkyl, optionally substituted with one or more halo, hydroxy, or cyano,
—(CH$_2$)$_t$—C$_{3-7}$cycloalkyl, optionally substituted by one or more B, and t is 0, 1, 2, 3 or 4,
—(CH$_2$)$_u$—O—C$_{1-7}$alkyl, wherein u is 2, 3, 4, 5 or 6,
—(CH$_2$)$_x$-heterocyclyl, wherein x is 0, 1, 2, 3 or 4, and wherein heterocyclyl is optionally substituted by one or more A
R$^d$ and R$^e$ together with the nitrogen to which they are bound form a heterocyclyl moiety, optionally substituted with one or more A, or
R$^3$ together with the neighboring pyridazine-nitrogen form a 5-membered annelated aromatic ring with two additional ring nitrogen atoms, the annelated ring is optionally substituted by R$^f$, wherein R$^f$ is C$_{1-7}$-alkyl, —C(O)OC$_{1-7}$alkyl, —C(O)C$_{1-7}$alkyl, 5- or 6-membered heteroaryl or phenyl, each optionally substituted by one or more E,
A is hydroxy, oxo, C$_{1-7}$alkyl, C$_{1-7}$alkoxy, C$_{1-7}$haloalkyl, C$_{1-7}$hydroxyalkyl, halo, or CN,
B is halo, hydroxy, CN, C$_{1-4}$alkyl, or C$_{1-4}$haloalkyl,
E is halo, CN, NO$_2$, hydroxy, C$_{1-7}$alkyl, C$_{1-7}$alkoxy, C$_{1-7}$haloalkyl, C$_{1-7}$hydroxyalkyl, C$_{1-7}$cyanoalkyl, C$_{1-7}$haloalkoxy, or C$_{3-7}$cycloalkyl,
or a pharmaceutically acceptable salt thereof.

In certain embodiments of the compound of formula I, X is O or NH. Each of these alternatives may be combined with any other embodiment as disclosed herein.

Further, it is to be understood that every embodiment relating to a specific residue R$^1$ to R$^5$ as disclosed herein may be combined with any other embodiment relating to another residue R$^1$ to R$^5$ as disclosed herein.

In certain embodiments of the compound of formula I, R$^1$ is phenyl, pyridinyl, or pyrimidinyl, each optionally substituted with one, two or three halo. Preferred halo substituents are chloro and fluoro. Preferably, phenyl is optionally substituted with one, two or three, more preferably with one or two, and in particular with one halo substituent selected from chloro and fluoro, preferably fluoro. Thereby, the halo substituents are located at the ortho, meta or para-position, and preferably at the meta or para position of the phenyl ring in respect to the attachment to the isoxazole.

In certain embodiments of the compound of formula I, R$^2$ is C$_{1-4}$alkyl or C$_{1-4}$haloalkyl. Preferably, R$^2$ is methyl or trifluoromethyl, more preferably methyl.

In certain embodiments of the compound of formula I, R$^3$ is as defined above.

In certain embodiments of the compound of formula I, R$^4$ is H, or C$_{1-7}$alkyl. Preferably, R$^4$ is H or C$_{1-4}$alkyl. More preferably, R$^4$ is H or methyl.

In certain embodiments of the compound of formula I, R$^5$ is H, or C$_{1-7}$alkyl. Preferably, R$^5$ is H or C$_{1-4}$alkyl. More preferably, R$^5$ is H or methyl.

In certain embodiments of the compound of formula I, R$^4$ and R$^5$ are each independently H, or C$_{1-7}$alkyl, preferably H or methyl, and R$^3$ is as defined above.

In certain embodiments of the compound of formula I, R$^3$ is
H,
C$_{1-7}$alkyl, optionally substituted with one or more halo, cyano, or hydroxy,
C$_{1-7}$alkoxy, optionally substituted with one or more halo,
halo,
—C(O)—R$^a$, wherein R$^a$ is hydroxy, C$_{1-7}$alkoxy, or C$_{1-7}$alkyl,
—NR$^b$R$^c$, wherein R$^b$ and R$^c$ are each independently
hydrogen,
C$_{1-7}$alkyl,
—C(O)C$_{1-7}$alkyl, optionally substituted with one or more halo,
—C(O)(CH$_2$)$_m$—O—C$_{1-7}$alkyl, wherein m is 0, 1, 2, 3, 4, 5 or 6, preferably 0 or 1,
—C(O)C(O)OC$_{1-7}$-alkyl,
—C(O)CH$_2$C(O)OC$_{1-7}$-alkyl,
—C(O)R$^i$, wherein R$^i$ is phenyl or 5- to 6-membered heteroaryl, each optionally substituted with one or more E,
—C(O)—C$_{3-7}$cycloalkyl, optionally substituted with one or more B,
—C(O)—R$^{ii}$, wherein R$^{ii}$ is 3- to 7-membered heterocyclyl, optionally substituted by one or more A,
3- to 7-membered heterocyclyl, optionally substituted with one or more A,
5- or 6-membered heteroaryl, optionally substituted with one or more E,
—C(O)—NR$^d$R$^e$, wherein R$^d$ and R$^e$ are each independently
H,
C$_{1-7}$alkyl, optionally substituted with one or more halo, hydroxy, or cyano,
—(CH$_2$)$_t$—C$_{3-7}$cycloalkyl, optionally substituted by one or more B, and t is 0, 1, 2, 3 or 4, preferably 0 or 1;
—(CH$_2$)$_u$—O—C$_{1-7}$alkyl, wherein u is 2, 3, 4, 5 or 6, preferably 2,
—(CH$_2$)$_x$-heterocyclyl, wherein x is 0, 1, 2, 3 or 4, preferably 0, and wherein heterocyclyl is optionally substituted by one or more A
R$^d$ and R$^e$ together with the nitrogen to which they are bound form a heterocyclyl moiety, optionally substituted with one or more A, or
R$^3$ together with the neighboring pyridazine-nitrogen form a 5-membered annelated aromatic ring with two additional ring nitrogen atoms, the annelated ring is optionally substituted by R$^f$, wherein R$^f$ is C$_{1-7}$-alkyl, —C(O)OC$_{1-7}$alkyl, or 5-membered heteroaryl,
A is hydroxy, oxo, C$_{1-7}$alkyl, C$_{1-7}$alkoxy, C$_{1-7}$haloalkyl, C$_{1-7}$hydroxyalkyl, halo, or CN,
B is halo, hydroxy, CN, C$_{1-4}$alkyl, or C$_{1-4}$haloalkyl,
E is halo, CN, NO$_2$, hydroxy, C$_{1-7}$alkyl, C$_{1-7}$alkoxy, C$_{1-7}$haloalkyl, C$_{1-7}$hydroxyalkyl, C$_{1-7}$cyanoalkyl, C$_{1-7}$haloalkoxy, or C$_{3-7}$cycloalkyl,
In certain embodiments of the compound of formula I, R$^3$ is
H,
C$_{1-7}$alkyl, optionally substituted with one or more halo, cyano, or hydroxy, $C_{1-7}$alkoxy, optionally substituted with one or more halo, halo,
—C(O)—$R^a$, wherein $R^a$ is hydroxy, $C_{1-7}$alkoxy, or $C_{1-7}$alkyl,
—$NR^bR^c$, wherein $R^b$ and $R^c$ are each independently
hydrogen,
$C_{1-7}$alkyl,
—C(O)$C_{1-7}$alkyl, optionally substituted with one or more halo,
—C(O)(CH$_2$)$_m$—O—$C_{1-7}$alkyl, wherein m is 0 or 1,
—C(O)C(O)O$C_{1-7}$-alkyl,
—C(O)CH$_2$C(O)O$C_{1-7}$-alkyl,
—C(O)$R^i$, wherein $R^i$ is phenyl, furanyl, or isoxazolyl, each optionally substituted with one or more E,
—C(O)—$C_{3-7}$cycloalkyl, optionally substituted with one or more B,
—C(O)—$R^{ii}$, wherein $R^{ii}$ is tetrahydropyranyl, optionally substituted with one or more A,
pyrrolidinyl or morpholinyl, each optionally substituted with one or more A,
pyrazolyl, optionally substituted with one or more E,
—C(O)—$NR^dR^e$, wherein $R^d$ and $R^e$ are each independently
H,
$C_{1-7}$alkyl, optionally substituted with one or more halo, or hydroxy,
—(CH$_2$)$_t$—$C_{3-7}$cycloalkyl, optionally substituted by one or more B, and t is 0 or 1;
—(CH$_2$)$_2$—O—$C_{1-7}$alkyl,
tetrahydropyranyl, optionally substituted by one or more A
$R^d$ and $R^e$ together with the nitrogen to which they are bound form morpholinyl, or thiomorpholinyl, each optionally substituted with one or more A, or
$R^3$ together with the neighboring pyridazine-nitrogen form a 5-membered annelated aromatic ring with two additional ring nitrogen atoms, the annelated ring is optionally substituted by $R^f$, wherein $R^f$ is $C_{1-7}$-alkyl, —C(O)O$C_{1-7}$alkyl, or furanyl,
A is hydroxy, oxo, $C_{1-7}$alkyl, $C_{1-7}$alkoxy, $C_{1-7}$haloalkyl, $C_{1-7}$hydroxyalkyl, halo, or CN,
B is halo, hydroxy, CN, $C_{1-4}$alkyl, or $C_{1-4}$haloalkyl,
E is halo, CN, NO$_2$, hydroxy, $C_{1-7}$alkyl, $C_{1-7}$alkoxy, $C_{1-7}$haloalkyl, $C_{1-7}$hydroxyalkyl, $C_{1-7}$cyanoalkyl, $C_{1-7}$haloalkoxy, or $C_{3-7}$cycloalkyl.

In certain embodiments of the invention, $R^3$, $R^4$ and $R^5$ are not simultaneously hydrogen.

A certain embodiment of the invention encompasses one of the above-mentioned combinations, namely the compound of general formula (I)

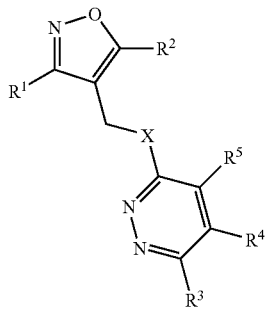

I wherein
X is O or NH;
$R^1$ is phenyl, pyridinyl or pyrimidinyl, each optionally substituted with one or two chloro or fluoro,
$R^2$ is methyl, H or trifluoromethyl, preferably methyl,
$R^3$ is H,
$C_{1-7}$alkyl, optionally substituted with one or more halo, cyano, or hydroxy,
$C_{1-7}$alkoxy, optionally substituted with one or more halo, halo,
—C(O)—$R^a$, wherein $R^a$ is hydroxy, $C_{1-7}$alkoxy, or $C_{1-7}$alkyl,
—$NR^bR^c$, wherein $R^b$ and $R^c$ are each independently
hydrogen,
$C_{1-7}$alkyl,
—C(O)$C_{1-7}$alkyl, optionally substituted with one or more halo,
—C(O)(CH$_2$)$_m$—O—$C_{1-7}$alkyl, wherein m is 0, 1, 2, 3, 4, 5 or 6, preferably 0 or 1,
—C(O)C(O)O$C_{1-7}$-alkyl,
—C(O)CH$_2$C(O)O$C_{1-7}$-alkyl,
—C(O)$R^i$, wherein $R^i$ is phenyl or 5- to 6-membered heteroaryl, each optionally substituted with one or more E,
—C(O)—$C_{3-7}$cycloalkyl, optionally substituted with one or more B,
—C(O)—$R^{ii}$, wherein $R^{ii}$ is 3- to 7-membered heterocyclyl, optionally substituted by one or more A,
3- to 7-membered heterocyclyl, optionally substituted with one or more A,
5- or 6-membered heteroaryl, optionally substituted with one or more E,
—C(O)—$NR^dR^e$, wherein $R^d$ and $R^e$ are each independently
H,
$C_{1-7}$alkyl, optionally substituted with one or more halo, hydroxy, or cyano,
—(CH$_2$)$_t$—$C_{3-7}$cycloalkyl, optionally substituted by one or more B, and t is 0, 1, 2, 3 or 4, preferably 0 or 1;
—(CH$_2$)$_u$—O—$C_{1-7}$alkyl, wherein u is 2, 3, 4, 5 or 6, preferably 2,
—(CH$_2$)$_x$-heterocyclyl, wherein x is 0, 1, 2, 3 or 4, preferably 0, and wherein heterocyclyl is optionally substituted by one or more A
$R^d$ and $R^e$ together with the nitrogen to which they are bound form a heterocyclyl moiety, optionally substituted with one or more A, or
$R^3$ together with the neighboring pyridazine-nitrogen form a 5-membered annelated aromatic ring with two additional ring nitrogen atoms, the annelated ring is optionally substituted by $R^f$, wherein $R^f$ is $C_{1-7}$-alkyl, —C(O)O$C_{1-7}$alkyl, or 5-membered heteroaryl,
$R^4$ and $R^5$ are each independently H or $C_{1-7}$alkyl,
A is hydroxy, oxo, $C_{1-7}$alkyl, $C_{1-7}$alkoxy, $C_{1-7}$haloalkyl, $C_{1-7}$hydroxyalkyl, halo, or CN,
B is halo, hydroxy, CN, $C_{1-4}$alkyl, or $C_{1-4}$haloalkyl,
E is halo, CN, NO$_2$, hydroxy, $C_{1-7}$alkyl, $C_{1-7}$alkoxy, $C_{1-7}$haloalkyl, $C_{1-7}$hydroxyalkyl, $C_{1-7}$cyanoalkyl, $C_{1-7}$haloalkoxy, or $C_{3-7}$cycloalkyl,
or a pharmaceutically acceptable salt thereof.

It is to be understood, that every other combination of $R^1$ to $R^5$, X, A, B and E as mentioned defined herein is herewith disclosed.

A preferred embodiment of the invention encompasses a compound of formula I

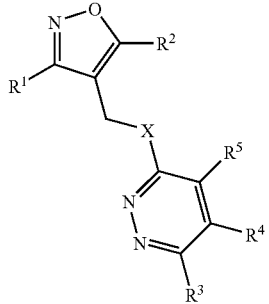

wherein
X is O or NH;
R¹ is phenyl, pyridinyl, or pyrimidinyl, each optionally substituted with one halo;
R² is H or $C_{1-4}$alkyl;
R⁴ is H or $C_{1-7}$alkyl;
R⁵ is H or $C_{1-7}$alkyl;
R³ is H,
  $C_{1-7}$alkyl,
  $C_{1-7}$alkoxy;
  halo,
  —C(O)—$R^a$, wherein $R^a$ is hydroxy, $C_{1-7}$alkoxy;
  —$NR^bR^c$, wherein $R^b$ and $R^c$ are each independently
    hydrogen,
    $C_{1-7}$alkyl,
    —C(O)$C_{1-7}$alkyl, optionally substituted with one or more halo,
    —C(O)(CH₂)$_m$—O—$C_{1-7}$alkyl, wherein m is 0 or 1;
    —C(O)C(O)O$C_{1-7}$-alkyl,
    —C(O)CH₂C(O)O$C_{1-7}$-alkyl,
    —C(O)$R^i$, wherein $R^i$ is phenyl or 5- to 6-membered heteroaryl, each optionally substituted with one E,
    —C(O)—$C_{3-7}$cycloalkyl;
    —C(O)—$R^{ii}$, wherein $R^{ii}$ is 3- to 7-membered heterocyclyl,
  3- to 7-membered heterocyclyl, optionally substituted with one A;
  5- or 6-membered heteroaryl;
  —C(O)—$NR^dR^e$, wherein $R^d$ and $R^e$ are each independently
    H,
    $C_{1-7}$alkyl, optionally substituted with one or more halo or hydroxy;
    —(CH₂)$_t$—$C_{3-7}$cycloalkyl, and t is 0, 1;
    —(CH₂)$_u$—O—$C_{1-7}$alkyl, wherein u is 2;
    -heterocyclyl;
    $R^d$ and $R^e$ together with the nitrogen to which they are bound form a heterocyclyl moiety, or
  R³ together with the neighboring pyridazine-nitrogen form a 5-membered annelated aromatic ring with two additional ring nitrogen atoms, the annelated ring is optionally substituted by $R^f$, wherein $R^f$ is $C_{1-7}$-alkyl, —C(O)O$C_{1-7}$alkyl or 5- or 6-membered heteroaryl;
A is oxo;
E is $C_{1-7}$alkyl;
or a pharmaceutically acceptable salt thereof.

Preferred compounds of present invention are those as listed in the examples below. Particularly preferred are the following compounds:

3-chloro-6-(5-methyl-3-phenyl-isoxazol-4-ylmethoxy)-pyridazine,
3-bromo-6-(5-methyl-3-phenyl-isoxazol-4-ylmethoxy)-pyridazine,
3-methyl-6-(5-methyl-3-phenyl-isoxazol-4-ylmethoxy)-pyridazine,
6-(5-methyl-3-phenyl-isoxazol-4-ylmethoxy)-pyridazine-3-carboxylic acid ethyl ester,
6-(5-methyl-3-phenyl-isoxazol-4-ylmethoxy)-pyridazine-3-carboxylic acid (2-methoxy-ethyl)-amide,
6-(5-methyl-3-phenyl-isoxazol-4-ylmethoxy)-pyridazine-3-carboxylic acid isopropylamide,
6-(5-methyl-3-phenyl-isoxazol-4-ylmethoxy)-pyridazine-3-carboxylic acid cyclopropylamide,
6-(5-methyl-3-phenyl-isoxazol-4-ylmethoxy)-pyridazine-3-carboxylic acid (tetrahydro-pyran-4-yl)-amide,
6-(5-methyl-3-phenyl-isoxazol-4-ylmethoxy)-pyridazine-3-carboxylic acid (2-hydroxy-ethyl)-amide,
6-(5-methyl-3-phenyl-isoxazol-4-ylmethoxy)-pyridazine-3-carboxylic acid (2-hydroxy-1,1-dimethyl-ethyl)-amide,
3-methoxy-6-(5-methyl-3-phenyl-isoxazol-4-ylmethoxy)-pyridazine,
6-(5-methyl-3-phenyl-isoxazol-4-ylmethoxy)-pyridazin-3-ylamine,
N-[6-(5-methyl-3-phenyl-isoxazol-4-ylmethoxy)-pyridazin-3-yl]-acetamide,
N-[6-(5-methyl-3-phenyl-isoxazol-4-ylmethoxy)-pyridazin-3-yl]-isobutyramide,
cyclopropanecarboxylic acid [6-(5-methyl-3-phenyl-isoxazol-4-ylmethoxy)-pyridazin-3-yl]-amide,
cyclobutanecarboxylic acid [6-(5-methyl-3-phenyl-isoxazol-4-ylmethoxy)-pyridazin-3-yl]-amide,
tetrahydro-pyran-4-carboxylic acid [6-(5-methyl-3-phenyl-isoxazol-4-ylmethoxy)-pyridazin-3-yl]-amide,
1-[6-(5-methyl-3-phenyl-isoxazol-4-ylmethoxy)-pyridazin-3-yl]-pyrrolidin-2-one,
N-[6-(5-methyl-3-phenyl-isoxazol-4-ylmethoxy)-pyridazin-3-yl]-oxalamic acid methyl ester,
N-[6-(5-methyl-3-phenyl-isoxazol-4-ylmethoxy)-pyridazin-3-yl]-benzamide,
furan-2-carboxylic acid [6-(5-methyl-3-phenyl-isoxazol-4-ylmethoxy)-pyridazin-3-yl]-amide,
isoxazole-5-carboxylic acid [6-(5-methyl-3-phenyl-isoxazol-4-ylmethoxy)-pyridazin-3-yl]-amide,
[6-(5-methyl-3-phenyl-isoxazol-4-ylmethoxy)-pyridazin-3-yl]-carbamic acid ethyl ester,
4-[6-(5-methyl-3-phenyl-isoxazol-4-ylmethoxy)-pyridazin-3-yl]-morpholine,
methyl-[6-(5-methyl-3-phenyl-isoxazol-4-ylmethoxy)-pyridazin-3-yl]-amine,
dimethyl-[6-(5-methyl-3-phenyl-isoxazol-4-ylmethoxy)-pyridazin-3-yl]-amine,
3-(3,5-dimethyl-pyrazol-1-yl)-6-(5-methyl-3-phenyl-isoxazol-4-ylmethoxy)-pyridazine,
5-methyl-6-(5-methyl-3-phenyl-isoxazol-4-ylmethoxy)-pyridazine-3-carboxylic acid ethyl ester,
3-chloro-4-methyl-6-(5-methyl-3-phenyl-isoxazol-4-ylmethoxy)-pyridazine,
4-methyl-6-(5-methyl-3-phenyl-isoxazol-4-ylmethoxy)-pyridazine-3-carboxylic acid ethyl ester,
4-methyl-6-(5-methyl-3-phenyl-isoxazol-4-ylmethoxy)-pyridazine-3-carboxylic acid (tetrahydro-pyran-4-yl)-amide,
4-methyl-6-(5-methyl-3-phenyl-isoxazol-4-ylmethoxy)-pyridazine-3-carboxylic acid cyclopropylamide,
4-methyl-6-(5-methyl-3-phenyl-isoxazol-4-ylmethoxy)-pyridazine-3-carboxylic acid isopropylamide, 6-[3-(3-fluoro-phenyl)-5-methyl-isoxazol-4-ylmethoxy]-pyridazine-3-carboxylic acid ethyl ester,
6-[3-(3-fluoro-phenyl)-5-methyl-isoxazol-4-ylmethoxy]-pyridazine-3-carboxylic acid methylamide,
6-[3-(3-fluoro-phenyl)-5-methyl-isoxazol-4-ylmethoxy]-pyridazine-3-carboxylic acid ethylamide,
6-[3-(3-fluoro-phenyl)-5-methyl-isoxazol-4-ylmethoxy]-pyridazine-3-carboxylic acid (2-hydroxy-ethyl)-amide,
6-[3-(3-fluoro-phenyl)-5-methyl-isoxazol-4-ylmethoxy]-pyridazine-3-carboxylic acid isopropylamide,
6-[3-(3-fluoro-phenyl)-5-methyl-isoxazol-4-ylmethoxy]-pyridazine-3-carboxylic acid cyclopropylamide,
3-chloro-6-[3-(4-fluoro-phenyl)-5-methyl-isoxazol-4-ylmethoxy]-pyridazine,
6-[3-(4-fluoro-phenyl)-5-methyl-isoxazol-4-ylmethoxy]-pyridazine-3-carboxylic acid ethyl ester,
6-[3-(4-fluoro-phenyl)-5-methyl-isoxazol-4-ylmethoxy]-pyridazine-3-carboxylic acid cyclopropylmethyl-amide,
6-[3-(4-fluoro-phenyl)-5-methyl-isoxazol-4-ylmethoxy]-pyridazine-3-carboxylic acid (2,2,2-trifluoro-ethyl)-amide,
6-[3-(4-fluoro-phenyl)-5-methyl-isoxazol-4-ylmethoxy]-pyridazine-3-carboxylic acid isopropylamide,
6-[3-(4-fluoro-phenyl)-5-methyl-isoxazol-4-ylmethoxy]-pyridazine-3-carboxylic acid cyclopropylamide,
6-[3-(4-fluoro-phenyl)-5-methyl-isoxazol-4-ylmethoxy]-pyridazine-3-carboxylic acid (tetrahydro-pyran-4-yl)-amide,
(1,1-dioxo-1λ6-thiomorpholin-4-yl)-{6-[3-(4-fluoro-phenyl)-5-methyl-isoxazol-4-ylmethoxy]-pyridazin-3-yl}-methanone,
6-(5-methyl-3-phenyl-isoxazol-4-ylmethoxy)-[1,2,4]triazolo[4,3-b]pyridazine,
6-(5-methyl-3-phenyl-isoxazol-4-ylmethoxy)-[1,2,4]triazolo[4,3-b]pyridazine-3-carboxylic acid ethyl ester,
6-[3-(4-fluoro-phenyl)-5-methyl-isoxazol-4-ylmethoxy]-[1,2,4]triazolo[4,3-b]pyridazine,
3-chloro-6-(5-methyl-3-pyridin-2-yl-isoxazol-4-ylmethoxy)-pyridazine,
6-(5-methyl-3-pyridin-2-yl-isoxazol-4-ylmethoxy)-pyridazine-3-carboxylic acid ethyl,
6-(5-methyl-3-pyridin-2-yl-isoxazol-4-ylmethoxy)-pyridazine-3-carboxylic acid (tetrahydro-pyran-4-yl)-amide,
6-(5-methyl-3-pyridin-2-yl-isoxazol-4-ylmethoxy)-pyridazine-3-carboxylic acid isopropylamide,
[6-(5-methyl-3-pyridin-2-yl-isoxazol-4-ylmethoxy)-pyridazin-3-yl]-morpholin-4-yl-methanone
6-(5-methyl-3-pyridin-2-yl-isoxazol-4-ylmethoxy)-pyridazine-3-carboxylic acid cyclopropylamide,
6-(5-methyl-3-pyridin-2-yl-isoxazol-4-ylmethoxy)-pyridazine-3-carboxylic acid (2,2,2-trifluoro-ethyl)-amide,
(1,1-dioxo-1λ6-thiomorpholin-4-yl)-[6-(5-methyl-3-pyridin-2-yl-isoxazol-4-ylmethoxy)-pyridazin-3-yl]-methanone,
6-(5-methyl-3-pyridin-2-yl-isoxazol-4-ylmethoxy)-pyridazine-3-carboxylic acid cyclopropylmethyl-amide,
6-(5-methyl-3-pyridin-2-yl-isoxazol-4-ylmethoxy)-pyridazine-3-carboxylic acid (2-hydroxy-ethyl)-amide,
6-(5-methyl-3-pyridin-2-yl-isoxazol-4-ylmethoxy)-pyridazine-3-carboxylic acid methylamide,
6-(5-methyl-3-pyridin-2-yl-isoxazol-4-ylmethoxy)-pyridazine-3-carboxylic acid ethylamide,
[6-(5-methyl-3-pyridin-2-yl-isoxazol-4-ylmethoxy)-pyridazin-3-yl]-thiomorpholin-4-yl-methanone,
6-(5-methyl-3-pyridin-2-yl-isoxazol-4-ylmethoxy)-pyridazine-3-carboxylic acid (2-hydroxy-1,1-dimethyl-ethyl)-amide,
6-(5-methyl-3-pyridin-2-yl-isoxazol-4-ylmethoxy)-pyridazine-3-carboxylic acid (2-methoxy-ethyl)-amide,
6-(5-methyl-3-pyridin-4-yl-isoxazol-4-ylmethoxy)-pyridazine-3-carboxylic acid (2-hydroxy-ethyl)-amide,
6-(5-methyl-3-pyridin-4-yl-isoxazol-4-ylmethoxy)-pyridazine-3-carboxylic acid methylamide,
6-(5-methyl-3-pyridin-4-yl-isoxazol-4-ylmethoxy)-pyridazine-3-carboxylic acid ethylamide,
3-chloro-6-[3-(5-fluoro-pyridin-2-yl)-5-methyl-isoxazol-4-ylmethoxy]-pyridazine,
6-[3-(5-fluoro-pyridin-2-yl)-5-methyl-isoxazol-4-ylmethoxy]-pyridazine-3-carboxylic acid ethyl ester,
6-[3-(5-fluoro-pyridin-2-yl)-5-methyl-isoxazol-4-ylmethoxy]-pyridazine-3-carboxylic acid (2-hydroxy-1,1-dimethyl-ethyl)-amide,
6-[3-(5-chloro-pyridin-2-yl)-5-methyl-isoxazol-4-ylmethoxy]-pyridazine-3-carboxylic acid,
6-(5-methyl-3-pyrimidin-4-yl-isoxazol-4-ylmethoxy)-pyridazine-3-carboxylic acid (2-hydroxy-ethyl)-amide,
6-(5-methyl-3-pyrimidin-4-yl-isoxazol-4-ylmethoxy)-pyridazine-3-carboxylic acid (2-hydroxy-1,1-dimethyl-ethyl)-amide,
6-{[3-(3-fluoro-phenyl)-5-methyl-isoxazol-4-ylmethyl]-amino}-pyridazine-3-carboxylic acid cyclopropylamide,
6-{[3-(3-fluoro-phenyl)-5-methyl-isoxazol-4-ylmethyl]-amino}-pyridazine-3-carboxylic acid cyclopropylmethyl-amide,
6-{[3-(3-fluoro-phenyl)-5-methyl-isoxazol-4-ylmethyl]-amino}-pyridazine-3-carboxylic acid (2,2,2-trifluoro-ethyl)-amide,
6-{[3-(5-chloro-pyridin-2-yl)-5-methyl-isoxazol-4-ylmethyl]-amino}-pyridazine-3-carboxylic acid (2-hydroxy-1,1-dimethyl-ethyl)-amide,
6-[3-(4-fluoro-phenyl)-isoxazol-4-ylmethoxy]-pyridazine-3-carboxylic acid ethyl ester,
6-[3-(4-fluoro-phenyl)-isoxazol-4-ylmethoxy]-pyridazine-3-carboxylic acid isopropylamide,
6-[3-(4-fluoro-phenyl)-isoxazol-4-ylmethoxy]-pyridazine-3-carboxylic acid (tetrahydro-pyran-4-yl)-amide,
6-(3-pyridin-2-yl-isoxazol-4-ylmethoxy)-pyridazine-3-carboxylic acid isopropylamide,
6-(3-pyridin-2-yl-isoxazol-4-ylmethoxy)-pyridazine-3-carboxylic acid cyclopropylamide,
6-(3-pyridin-2-yl-isoxazol-4-ylmethoxy)-pyridazine-3-carboxylic acid cyclopropylmethyl-amide,
6-(3-pyridin-2-yl-isoxazol-4-ylmethoxy)-pyridazine-3-carboxylic acid (2,2,2-trifluoro-ethyl)-amide, or
6-[3-(5-fluoro-pyridin-2-yl)-isoxazol-4-ylmethoxy]-pyridazine-3-carboxylic acid (2-hydroxy-1,1-dimethyl-ethyl)-amide.

The present compounds of formula I (X=O) and their pharmaceutically acceptable salts can be prepared by a process comprising the steps of:
a) reacting a compound of formula II:

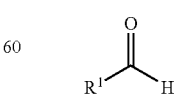

II with hydroxylamine hydrochloride in a suitable solvent, such as ethanol and water, in the presence of a base, such as aqueous sodium hydroxide, to give a compound of formula III:

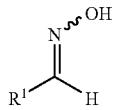
III b) reacting the compound of formula III with a chlorinating agent such as N-chlorosuccinimide, in a suitable solvent, such as DMF, to give a compound of formula IV:

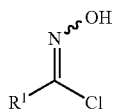
IV c1) and then either reacting the compound of formula IV with a compound of formula V:

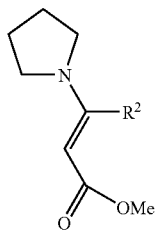
V in the presence of a suitable base, such as triethylamine, in a suitable solvent, such as chloroform, or alternatively c2) reacting the compound of formula IV with a compound of formula VI:

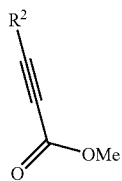
VI in the presence of a suitable base, such as triethylamine, in a suitable solvent, such as diethylether, to give a compound of formula VII:

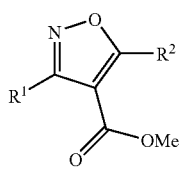
VII d) reacting a compound of formula VII with a reducing agent, such as lithiumaluminiumhydride, in a suitable solvent, such as THF to give a compound of formula VIII:

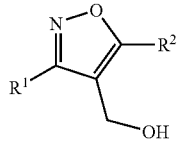
VIII e1) reacting compounds of formula VIII with a compound of formula IX:

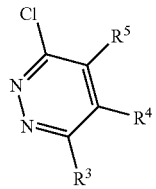
IX in the presence of a suitable base, such as sodium hydride, in a suitable solvent, such as THF, or alternatively e2) reacting compounds of formula VIII with a compound of formula X:

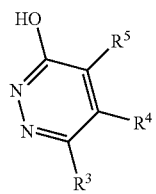
X in the presence of triphenylphosphine and diethylazodicarboxylate, in a suitable solvent, such as THF, to give a compound of formula I-a:

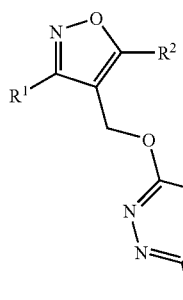
I-a wherein $R^1$ to $R^5$ are as described for formula I hereinabove, and, if desired, converting a compound of formula I into a pharmaceutically acceptable salt.

The present compounds of formula I (X=NH) and their pharmaceutically acceptable salts can be prepared by a process comprising the steps of:

f) reacting a compound of formula VIII:

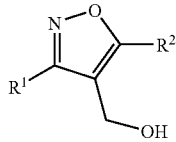

VIII with phthalimide in the presence of triphenylphosphine and diethylazodicarboxylate, in a suitable solvent, such as THF, to give a compound of formula XI:

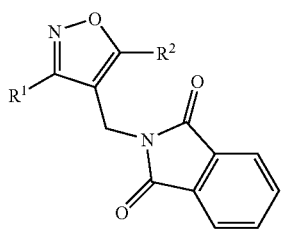

XI g) reacting the compound of formula XI with hydrazine, to give a compound of formula XII:

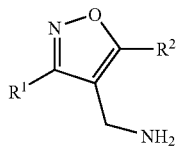

XII h) reacting compounds of formula XII with a compound of formula IX:

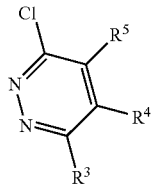

IX in the presence of a suitable base, such as sodium hydride, or N,N-diisopropyl ethyl amine, in a suitable solvent, such as THF or DMSO, under traditional heating or microwave irradiation at elevated temperatures, such as 160° C., to give a compound of formula I-b:

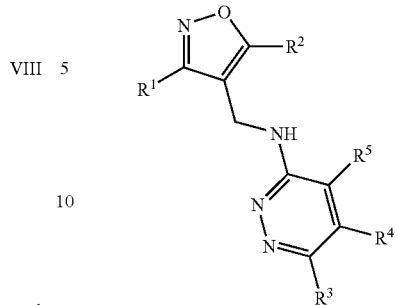

I-b

The present compounds of formula I-c (X=O) and their pharmaceutically acceptable salts can be prepared by a process comprising the steps of:

i) reacting compounds of formula VIII

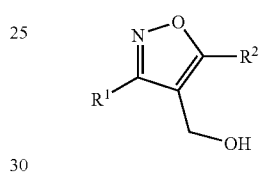

VIII with a compound of formula XIII

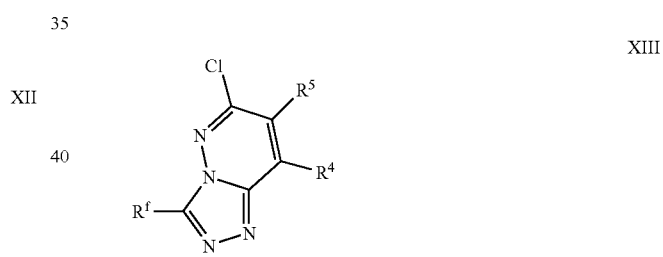

XIII in the presence of a suitable base, such as sodium hydride, in a suitable solvent, such as THF, to give a compound of formula I-c:

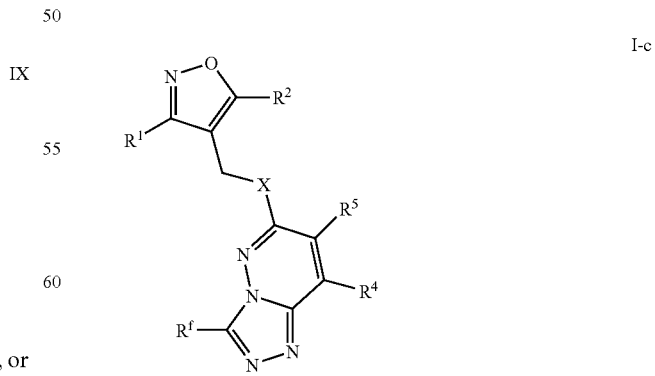

I-c

In accordance with Schemes 1-5, compounds of formula I can be prepared following standard methods.

Scheme 1
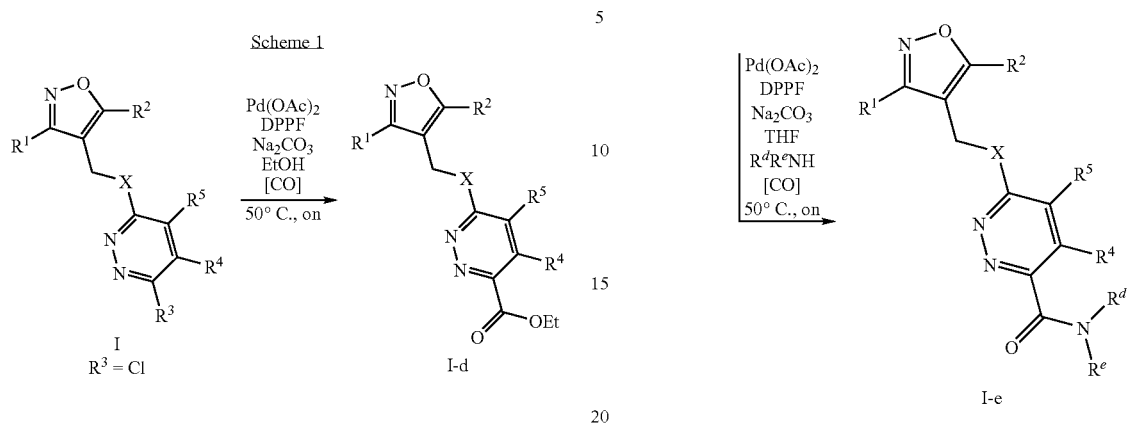
Scheme 2
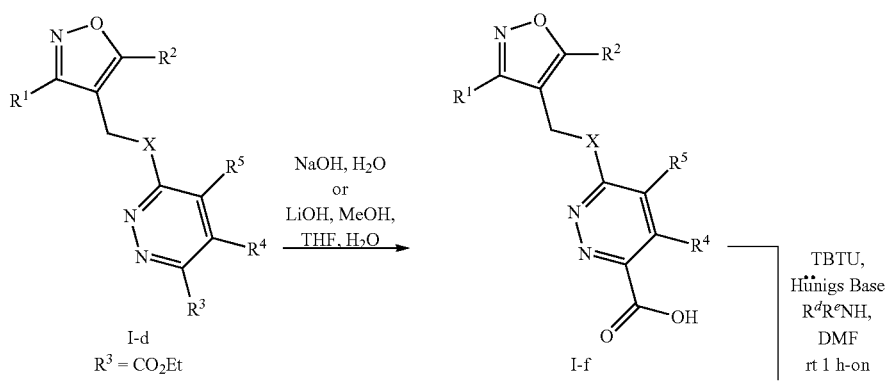
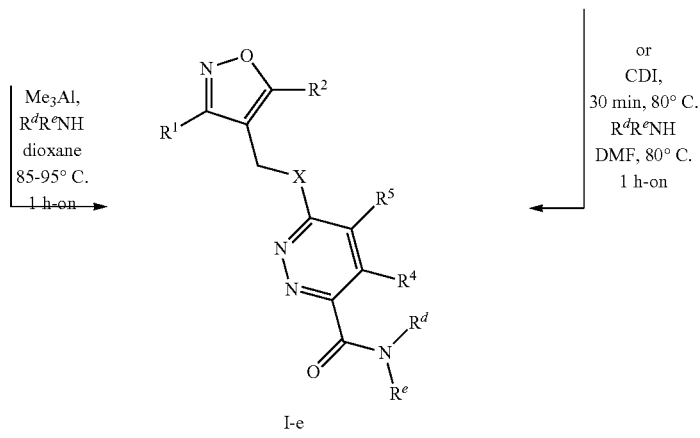

Scheme 3

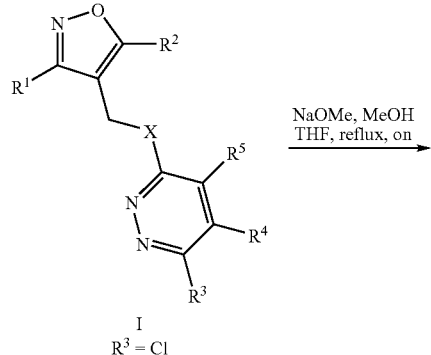

Scheme 4

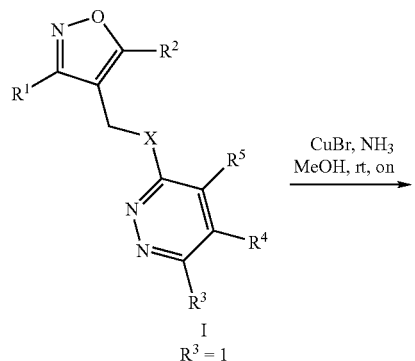

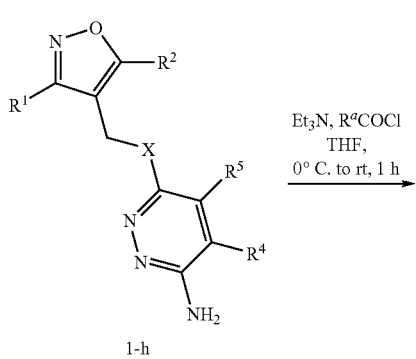

Scheme 5

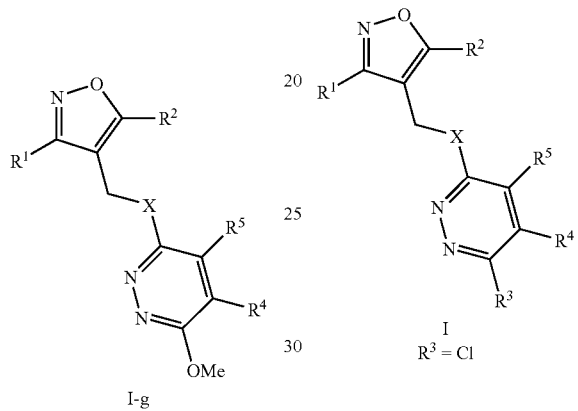

on=overnight
rt=room temperature
DMF=N,N-dimethylformamide
TBTU=O-(benzotriazol-1-yl)-N,N,N',N'-tetramethyluronium tetrafluoroborate As mentioned earlier, the compounds of formula I and their pharmaceutically usable salts possess valuable pharmacological properties. Compounds of the present invention are ligands for GABA A receptors containing the α5 subunit and are therefore useful in the therapies where cognitive enhancement is required.

The compounds were investigated in accordance with the test given hereinafter:

Membrane Preparation and Binding Assay

The affinity of compounds at GABA A receptor subtypes was measured by competition for [3H]flumazenil (85

Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 μL (96-well plates) which contained 100 μL of cell membranes, [3H]flumazenil at a concentration of 1 nM for α1, α2, α3 subunits and 0.5 nM for α5 subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit.

Representative test results are shown in the table below:

TABLE 1

| Ex. | hKi [nM] |
| --- | --- |
| 1 | 9.6 |
| 2 | 7.6 |
| 4 | 6.2 |
| 5 | 5.5 |
| 6 | 5.4 |
| 7 | 5.9 |
| 8 | 3.5 |
| 9 | 4.8 |
| 12 | 3.4 |
| 13 | 7.7 |
| 14 | 12.3 |
| 15 | 4.1 |
| 17 | 3.9 |
| 20 | 7.9 |
| 21 | 5.3 |
| 22 | 10.1 |
| 25 | 8.7 |
| 27 | 4 |
| 28 | 5.1 |
| 30 | 13.7 |
| 32 | 6.9 |
| 33 | 5.4 |
| 34 | 8.6 |
| 36 | 9.4 |
| 37 | 6.3 |
| 38 | 8.4 |
| 39 | 5.1 |
| 40 | 2.2 |
| 41 | 2.3 |
| 42 | 1.9 |
| 44 | 3.4 |
| 45 | 1.4 |

TABLE 1-continued

| Ex. | hKi [nM] |
| --- | --- |
| 46 | 3.6 |
| 49 | 9.6 |
| 50 | 4.1 |
| 51 | 6.1 |
| 52 | 6.6 |
| 54 | 8.4 |
| 55 | 6.7 |
| 57 | 4.6 |
| 58 | 3.3 |
| 59 | 4.6 |
| 60 | 3.5 |
| 61 | 3.4 |
| 62 | 1.7 |
| 63 | 2.4 |
| 66 | 11.7 |
| 86 | 6.6 |
| 91 | 7.5 |
| 92 | 3.8 |
| 93 | 2.9 |
| 94 | 2.9 |
| 95 | 2.7 |
| 96 | 25.9 |
| 97 | 1.6 |
| 98 | 2.8 |
| 99 | 18.1 |
| 100 | 4.1 |
| 101 | 1.4 |
| 102 | 0.9 |
| 103 | 1.5 |
| 104 | 27.8 |
| 105 | 4.0 |
| 106 | 1.6 |
| 107 | 23.3 |
| 108 | 9 |
| 109 | 14.2 |
| 110 | 1.6 |
| 111 | 1.2 |
| 112 | 1.5 |
| 113 | 2.1 |
| 114 | 4.7 |
| 115 | 14.8 |
| 118 | 28.9 |
| 119 | 7.3 |
| 121 | 27.6 |
| 122 | 34.7 |
| 124 | 31.5 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc. can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, in the case of oral administration a daily dosage of about 0.1 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition can be manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition can be manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture then can be returned to the mixer, the talc can be added thereto and mixed thoroughly. The mixture can be filled by machine into hard gelatin capsules.

EXAMPLE C

Suppositories of the following composition can be manufactured:

|  | mg/supp. |
|---|---|
| Active substance | 15 |
| Suppository mass | 128 |
| Total | 1300 |

The suppository mass can be melted in a glass or steel vessel, mixed thoroughly and cooled to 45° C.

Thereupon, the finely powdered active substance can be added thereto and stirred until it has dispersed completely. The mixture then can be poured into suppository moulds of suitable size, left to cool, the suppositories then can be removed from the moulds and packed individually in wax paper or metal foil.

The following examples 1-127 are provided for illustration of the invention. They should not be considered as limiting the scope of the invention, but merely as being representative thereof.

EXAMPLE 1

3-Chloro-6-(5-methyl-3-phenyl-isoxazol-4-yl-methoxy)-pyridazine

To a solution of (5-methyl-3-phenyl-isoxazol-4-yl)-methanol (5.0 g, 26.4 mmol) in THF (50 mL) was added sodium hydride (55% dispersion in mineral oil, 1.27 g, 29.1 mmol). The mixture was stirred at room temperature for 30 min. After addition of 3,6-dichloropyridazine (4.33 g, 29.1 mmol) the mixture was stirred at room temperature for another 5 h. Then the mixture was evaporated, extracted (ethyl acetate/water) and the organic phase was dried with sodium sulfate and concentrated. Chromatography ($SiO_2$, heptane:ethyl acetate=100:0 to 70:30) afforded the title compound (6.62 g, 83%) as a white solid. MS: m/e=302.0 $[M+H]^+$.

EXAMPLE 2

3-Bromo-6-(5-methyl-3-phenyl-isoxazol-4-yl-methoxy)-pyridazine

As described for example 1, (5-methyl-3-phenyl-isoxazol-4-yl)-methanol (2.46 g, 13 mmol) was converted using 3,6-dibromopyridazine instead of 3,6-dichloropyridazine to the title compound (3.99 g, 89%) as a white solid. MS: m/e=348.0/346.1 $[M+H]^+$.

EXAMPLE 3

3-(5-Methyl-3-phenyl-isoxazol-4-ylmethoxy)-pyridazine

Ammonium formate (0.20 g, 3.2 mmol) was added to a solution of 3-bromo-6-(5-methyl-3-phenyl-isoxazol-4-yl-methoxy)-pyridazine (0.54 g, 1.6 mmol) in ethanol (8 mL). The reaction flask was flushed with argon. Palladium on charcoal (10%, 0.05 g) was added and the mixture was heated to 40° C. After 16 h, additional ammonium formate (0.20 g, 3.2 mmol) and palladium on charcoal (10%, 0.05 g) was added and the mixture was heated to 40° C. for another 24 h. The mixture was filtered, concentrated and extracted (ethyl acetate/sodium bicarbonate solution). The organic layer was dried over sodium sulfate, concentrated and chromatographed (SiO$_2$, heptane:ethyl acetate=100:0 to 60:40) to afford the title compound (160 mg, 38%) as a colorless oil. MS: m/e=268.1 [M+H]$^+$.

EXAMPLE 4

3-Methyl-6-(5-methyl-3-phenyl-isoxazol-4-yl-methoxy)-pyridazine

To a solution of (5-methyl-3-phenyl-4-isoxazolyl)methanol (0.50 g, 2.64 mmol) in THF (8 mL) was added sodium hydride (55% dispersion in mineral oil, 0.16 g, 3.17 mmol) at 0° C. The reaction mixture was stirred for 30 min while it was allowed to warm up to room temperature. 3-Chloro-6-methylpyridazine (0.36 g, 2.77 mmol) was added and stirring was continued for 2 h. Water (10 mL) was added and the mixture was extracted with ethyl acetate (40 mL). The combined organic layers were washed with brine (10 mL) and dried over sodium sulfate. Concentration and purification of the residue by chromatography (SiO$_2$, heptane:ethyl acetate=100:0 to 50:50) afforded the title compound (220 mg, 30%) as a yellow oil. MS: m/e=282.3 [M+H]$^-$.

EXAMPLE 5

6-(5-Methyl-3-phenyl-isoxazol-4-ylmethoxy)-pyridazine-3-carboxylic acid ethyl ester To a solution of 3-chloro-6-(5-methyl-3-phenyl-isoxazol-4-ylmethoxy)-pyridazine (200 mg, 0.66 mmol) in ethanol (3 mL) was added sodium carbonate (70 mg, 0.66 mmol), 1,1'-bis(diphenylphosphino)ferrocene (37 mg, 0.06 mmol) and palladium(II) acetate (15 mg, 0.06 mmol). The resulting mixture was stirred at 50° C. for 1 h under a carbon monoxide atmosphere. After cooling to room temperature it was filtered through Celite® and concentrated. Purification by chromatography (SiO$_2$, heptane:ethyl acetate=100:0 to 60:40) afforded the title compound (196 mg, 87%) as a light yellow oil. MS: m/e=340.2 [M+H]$^+$.

EXAMPLE 6

6-(5-Methyl-3-phenyl-isoxazol-4-ylmethoxy)-pyridazine-3-carboxylic acid (2-methoxy-ethyl)-amide To a solution of 3-chloro-6-(5-methyl-3-phenyl-isoxazol-4-ylmethoxy)-pyridazine (200 mg, 0.66 mmol) in THF (5 mL) was added 2-methoxyethylamine (0.29 mL, 3.30 mmol), sodium carbonate (70 mg, 0.66 mmol), 1,1'-bis(diphenylphosphino)ferrocene (37 mg, 0.06 mmol) and palladium (II) acetate (15 mg, 0.06 mmol). The resulting mixture was stirred at 50° C. for 18 h under a carbon monoxide atmosphere then filtered through Celite®. Concentration and purification by chromatography (SiO$_2$, heptane:ethyl acetate=100:0 to 50:50) afforded the title compound (61 mg, 25%) as a light yellow oil. MS: m/e=369.0 [M+H]$^+$.

EXAMPLE 7

6-(5-Methyl-3-phenyl-isoxazol-4-ylmethoxy)-pyridazine-3-carboxylic acid isopropylamide As described for example 6, 3-chloro-6-(5-methyl-3-phenyl-isoxazol-4-ylmethoxy)-pyridazine (200 mg, 0.66 mmol) was converted, using isopropylamine instead of 2-methoxyethylamine, to the title compound (50 mg, 21%) which was obtained as a white solid. MS: m/e=353.2 [M+H]$^+$.

EXAMPLE 8

6-(5-Methyl-3-phenyl-isoxazol-4-ylmethoxy)-pyridazine-3-carboxylic acid cyclopropylamide As described for example 6, 3-chloro-6-(5-methyl-3-phenyl-isoxazol-4-ylmethoxy)-pyridazine (200 mg, 0.66 mmol) was converted, using cyclopropylamine instead of 2-methoxyethylamine, to the title compound (31 mg, 13%) which was obtained as a white solid. MS: m/e=351.3 [M+H]$^+$.

EXAMPLE 9

6-(5-Methyl-3-phenyl-isoxazol-4-ylmethoxy)-pyridazine-3-carboxylic acid (tetrahydro-pyran-4-yl)-amide As described for example 6, 3-chloro-6-(5-methyl-3-phenyl-isoxazol-4-ylmethoxy)-pyridazine (200 mg, 0.66 mmol) was converted, using 4-aminotetrahydropyran instead of 2-methoxyethylamine, to the title compound (50 mg, 19%) which was obtained as an off white solid. MS: m/e=395.2 [M+H]$^+$.

EXAMPLE 10

[6-(5-Methyl-3-phenyl-isoxazol-4-ylmethoxy)-pyridazin-3-yl]-morpholin-4-yl-methanone As described for example 6, 3-chloro-6-(5-methyl-3-phenyl-isoxazol-4-ylmethoxy)-pyridazine (200 mg, 0.66 mmol) was converted, using morpholine instead of 2-methoxyethylamine, to the title compound (16 mg, 6%) which was obtained as a colourless crystalline solid. MS: m/e=381.3 [M+H]$^+$.

EXAMPLE 11

(1,1-Dioxo-1λ6-thiomorpholin-4-yl)-[6-(5-methyl-3-phenyl-isoxazol-4-ylmethoxy)-pyridazin-3-yl]-methanone a) 6-(5-Methyl-3-phenyl-isoxazol-4-ylmethoxy)-pyridazine-3-carboxylic acid To a solution of 6-(5-methyl-3-phenyl-isoxazol-4-ylmethoxy)-pyridazine-3-carboxylic acid ethyl ester (3.1 g, 9.0 mmol) in ethanol (15 mL) was added aqueous sodium hydroxide (1 N, 27.5 mL). After heating at 60° C. for 30 min it was cooled to ambient temperature and and aqueous sodium carbonate (2 M, 50 mL) added. Addition of aqueous sodium hydroxide (1 M, 50 mL) was followed by extraction with tert-butylmethylether. The aqueous phase was acidified with aqueous hydrogen chloride (25%) to pH=2 and extracted with tert-butylmethylether and ethyl acetate. The combined organic layers were dried over sodium sulfate and concentration afforded the title compound (2.8 g, 100%) as a white solid after trituration from tert-butylmethylether. MS: m/e=309.3 [M−H]$^-$.

b) (1,1-Dioxo-1λ6-thiomorpholin-4-yl)-[6-(5-methyl-3-phenyl-isoxazol-4-ylmethoxy)-pyridazin-3-yl]-methanone To a solution of 6-(5-methyl-3-phenyl-isoxazol-4-ylmethoxy)-pyridazine-3-carboxylic acid (200 mg, 0.64 mmol)

in DMF (8 mL) were added 2-(1H-benzotriazole-1-yl)-1,1,3,3-tetramethyluronium tetrafluoroborate (227 mg, 0.70 mmol), N,N-diisopropyl ethyl amine (550 µL, 3.2 mmol) and thiomorpholine 1,1-dioxide (0.104 g, 0.77 mmol). The resulting reaction mixture was stirred for 30 min at room temperature and diluted with water. The mixture was then extracted with ethyl acetate and the combined organic layers washed with aqueous sodium carbonate (saturated) and dried over sodium sulfate. Concentration and purification by chromatography ($SiO_2$, heptane:ethyl acetate=100:0 to 6:4) afforded the title compound (176 mg, 63%) as a white solid. MS: m/e=429.2 $[M+H]^+$.

EXAMPLE 12

6-(5-Methyl-3-phenyl-isoxazol-4-ylmethoxy)-pyridazine-3-carboxylic acid (2-hydroxy-ethyl)-amide To a solution of 6-(5-methyl-3-phenyl-isoxazol-4-ylmethoxy)-pyridazine-3-carboxylic acid (200 mg, 0.64 mmol) in DMF (8 mL) was added 1,1-carbonyl-diimidazole (135 mg, 0.83 mmol) and the mixture was stirred for 4 h at room temperature. Ethanolamine (0.27 mL, 4.50 mmol) was added and stirring was continued for 1 h. Water (20 mL) was added and the mixture was extracted with ethyl acetate (90 mL). The combined organic layers were washed with water (60 mL) and dried over sodium sulfate. Concentration and purification by chromatography ($SiO_2$, heptane:ethyl acetate=95:5 to 30:70) afforded the title compound (215 mg, 94%) as a white foam. MS: m/e=355.2 $[M+H]^+$.

EXAMPLE 13

6-(5-Methyl-3-phenyl-isoxazol-4-ylmethoxy)-pyridazine-3-carboxylic acid (2-hydroxy-1,1-dimethyl-ethyl)-amide As described for example 12, 6-(5-methyl-3-phenyl-isoxazol-4-ylmethoxy)-pyridazine-3-carboxylic acid (200 mg, 0.64 mmol) was converted, using 2-amino-2-methyl-propanol instead of ethanolamine, to the title compound ($SiO_2$, heptane:ethyl acetate=95:5 to 50:50, 202 mg, 82%) which was obtained as a white foam. MS: m/e=383.3 $[M+H]^+$.

EXAMPLE 14

3-Methoxy-6-(5-methyl-3-phenyl-isoxazol-4-ylmethoxy)-pyridazine

To a solution of 3-chloro-6-(5-methyl-3-phenyl-isoxazol-4-ylmethoxy)-pyridazine (200 mg, 0.66 mmol) in a mixture of methanol (3 mL) and THF (1 mL) was added dropwise sodium methoxide (5.4 M in MeOH, 0.16 mL, 0.86 mmol) and the reaction mixture was heated under reflux for 24 h. After dilution with tert-butylmethylether (4 mL) and water (2 mL) it was extracted with tert-butylmethylether (15 mL) and dried over sodium sulfate. Concentration and purification by chromatography ($SiO_2$, heptane:ethyl acetate=100:0 to 50:50) afforded the title compound (56 mg, 27%) as a colorless oil. MS: m/e=298.3 $[M+H]^+$.

EXAMPLE 15

6-(5-Methyl-3-phenyl-isoxazol-4-ylmethoxy)-pyridazin-3-ylamine a) 3-Iodo-6-(5-methyl-3-phenyl-isoxazol-4-ylmethoxy)-pyridazine As described for example 1, (5-methyl-3-phenyl-isoxazol-4-yl)-methanol (10.0 g, 53 mmol) was converted using 3-chloro-6-iodopyridazine (Goodman, A. J.; Stanforth, S. P.; Tarbit, B. *Tetrahedron* 1999, 55, 15067) instead of 3,6-dichloropyridazine to the title compound (16.9 g, 81%) which was contaminated with ca. 20% of 3-chloro-6-(5-methyl-3-phenyl-isoxazol-4-ylmethoxy)-pyridazine. The product was obtained as an off white solid. MS: m/e=394.0 $[M+H]^+$.

b) 6-(5-Methyl-3-phenyl-isoxazol-4-ylmethoxy)-pyridazin-3-ylamine

3-Iodo-6-(5-methyl-3-phenyl-isoxazol-4-ylmethoxy)-pyridazine (example 15a) (200 mg, 0.5 mmol) was dissolved in a solution of ammonia in methanol (7 M, 3 mL). After addition of copper(I) bromide (88 mg, 0.6 mmol) the mixture was stirred for 16 h at room temperature. The precipitate was filtered and the organic phase was adsorbed on silica. Chromatography ($SiO_2$, dichloromethane:methanol=100:0 to 95:5) afforded the title compound (66 mg, 46%) as a light yellow solid. MS: m/e=283.1 $[M+H]^+$.

EXAMPLE 16

N-Acetyl-N-[6-(5-methyl-3-phenyl-isoxazol-4-ylmethoxy)-pyridazin-3-yl]-acetamide To a solution of 6-(5-methyl-3-phenyl-isoxazol-4-ylmethoxy)-pyridazin-3-ylamine (200 mg, 0.7 mmol) in THF (4 mL) was added triethylamine (0.12 mL, 0.85 mmol). The mixture was cooled in an ice bath and a solution of acetyl chloride (0.067 ml, 0.85 mmol) in THF (1 ml) was added dropwise. After stirring for 1 h at room temperature the precipitate was filtered and the organic phase was evaporated. Chromatography ($SiO_2$, dichloromethane:methanol=100:0 to 98:2) afforded the title compound (160 mg, 62%) as a light yellow oil. MS: m/e=367.4 $[M+H]^+$.

EXAMPLE 17

N-[6-(5-Methyl-3-phenyl-isoxazol-4-ylmethoxy)-pyridazin-3-yl]-acetamide

A solution of N-acetyl-N-[6-(5-methyl-3-phenyl-isoxazol-4-ylmethoxy)-pyridazin-3-yl]-acetamide (70 mg, 0.19 mmol) in methanol (2 mL) was treated with sodium bicarbonate (1 spatula) and stirred at room temperature for 16 h. The solvent was evaporated and the residue was extracted (dichloromethane/water). The organic phase was dried over sodium sulfate and concentrated. Crystallization of the residue from diisopropylether afforded the title compound as a light brown solid (40 mg, 65%). MS: m/e=325.4 $[M+H]^+$.

EXAMPLE 18

2-Methoxy-N-[6-(5-methyl-3-phenyl-isoxazol-4-ylmethoxy)-pyridazin-3-yl]-acetamide To a solution of 6-(5-methyl-3-phenyl-isoxazol-4-ylmethoxy)-pyridazin-3-ylamine (200 mg, 0.7 mmol) in THF (4 mL) was added triethylamine (0.12 mL, 0.85 mmol). The mixture was cooled in an ice bath and a solution of methoxyacetyl chloride (0.092 mL, 0.85 mmol) in THF (1 mL) was added dropwise. After stirring for 1 h at room temperature the precipitate was filtered and the organic phase was evaporated. The residue was dissolved in methanol (5 mL), sodium bicarbonate (1 spatula) was added and the mixture was stirred at room temperature for 2 h. The solvent was evaporated and the residue was extracted (dichloromethane/water). Then the organic phase was dried over sodium sulfate and concentrated. Chromatography (SiO$_2$, dichloromethane:methanol=100:0 to 98:2) afforded the title compound (180 mg, 73%) as a white solid. MS: m/e=355.3 [M+H]$^+$.

EXAMPLE 19

N-[6-(5-Methyl-3-phenyl-isoxazol-4-ylmethoxy)-pyridazin-3-yl]-butyramide

As described for example 18, 6-(5-methyl-3-phenyl-isoxazol-4-ylmethoxy)-pyridazin-3-ylamine (200 mg, 0.7 mmol) was converted, using butyryl chloride instead of methoxyacetyl chloride, to the title compound (155 mg, 62%) which was obtained as a white solid. MS: m/e=353.3 [M+H]$^-$.

EXAMPLE 20

N-[6-(5-Methyl-3-phenyl-isoxazol-4-ylmethoxy)-pyridazin-3-yl]-isobutyramide

As described for example 18, 6-(5-methyl-3-phenyl-isoxazol-4-ylmethoxy)-pyridazin-3-ylamine (200 mg, 0.7 mmol) was converted, using isobutyryl chloride instead of methoxyacetyl chloride, to the title compound (180 mg, 72%) which was obtained as a white solid. MS: m/e=353.2 [M+H]$^-$.

EXAMPLE 21

Cyclopropanecarboxylic acid [6-(5-methyl-3-phenyl-isoxazol-4-ylmethoxy)-pyridazin-3-yl]-amide As described for example 18, 6-(5-methyl-3-phenyl-isoxazol-4-ylmethoxy)-pyridazin-3-ylamine (200 mg, 0.7 mmol) was converted, using cyclopropanecarbonyl chloride instead of methoxyacetyl chloride, to the title compound (185 mg, 75%) which was obtained as a white solid. MS: m/e=351.3 [M+H]$^+$.

EXAMPLE 22

Cyclobutanecarboxylic acid [6-(5-methyl-3-phenyl-isoxazol-4-ylmethoxy)-pyridazin-3-yl]-amide As described for example 18, 6-(5-methyl-3-phenyl-isoxazol-4-ylmethoxy)-pyridazin-3-ylamine (200 mg, 0.7 mmol) was converted, using cyclobutanecarbonyl chloride instead of methoxyacetyl chloride, to the title compound (165 mg, 64%) which was obtained as a white solid. MS: m/e=365.4 [M+H]$^+$.

EXAMPLE 23

2,2-Dimethyl-N-[6-(5-methyl-3-phenyl-isoxazol-4-ylmethoxy)-pyridazin-3-yl]-propionamide As described for example 18, 6-(5-methyl-3-phenyl-isoxazol-4-ylmethoxy)-pyridazin-3-ylamine (280 mg, 1 mmol) was converted, using pivaloyl chloride instead of methoxyacetyl chloride, to the title compound (320 mg, 87%) which was obtained as a white solid. MS: m/e=367.1 [M+H].

EXAMPLE 24

Cyclopentanecarboxylic acid [6-(5-methyl-3-phenyl-isoxazol-4-ylmethoxy)-pyridazin-3-yl]-amide As described for example 18, 6-(5-methyl-3-phenyl-isoxazol-4-ylmethoxy)-pyridazin-3-ylamine (280 mg, 1 mmol) was converted, using cyclopentanecarbonyl chloride instead of methoxyacetyl chloride, to the title compound (295 mg, 78%) which was obtained as a white solid. MS: m/e=379.4 [M+H]$^+$.

EXAMPLE 25

Tetrahydro-pyran-4-carboxylic acid [6-(5-methyl-3-phenyl-isoxazol-4-ylmethoxy)-pyridazin-3-yl]-amide As described for example 18, 6-(5-methyl-3-phenyl-isoxazol-4-ylmethoxy)-pyridazin-3-ylamine (280 mg, 1 mmol) was converted, using tetrahydro-2H-pyran-4-carbonyl chloride instead of methoxyacetyl chloride, to the title compound (360 mg, 91%) which was obtained as a white solid. MS: m/e=395.1 [M+H]$^+$.

EXAMPLE 26

4-Chloro-N-[6-(5-methyl-3-phenyl-isoxazol-4-ylmethoxy)-pyridazin-3-yl]-butyramide To a solution of 6-(5-methyl-3-phenyl-isoxazol-4-ylmethoxy)-pyridazin-3-ylamine (1.0 g, 3.5 mmol) in THF (15 ml) was added triethylamine (0.59 mL, 4.3 mmol). The mixture was cooled in an ice bath and a solution of 4-chlorobutyryl chloride (0.48 mL, 4.3 mmol) in THF (5 mL) was added dropwise. After stirring for 1 h at room temperature the precipitate was filtered and the organic phase was evaporated. The residue was dissolved in methanol (20 mL), sodium bicarbonate (1 spatula) was added and the mixture was stirred at room temperature for 1 h. The solvent was evaporated and the residue was extracted (dichloromethane/water). Then the organic phase was dried over sodium sulfate and concentrated. Purification by chromatography (SiO$_2$, heptane/ethyl acetate=100:0 to 60:40) afforded the title compound (740 mg, 54%) (as the least polar component of two formed in the reaction) which was obtained as a white solid. MS: m/e=387.3 [M+H]$^+$.

EXAMPLE 27

1-[6-(5-Methyl-3-phenyl-isoxazol-4-ylmethoxy)-pyridazin-3-yl]-pyrrolidin-2-one

To a solution of 6-(5-methyl-3-phenyl-isoxazol-4-ylmethoxy)-pyridazin-3-ylamine (1.0 g, 3.5 mmol) in THF (15 ml) was added triethylamine (0.59 mL, 4.3 mmol). The mixture was cooled in an ice bath and a solution of 4-chlorobutyryl chloride (0.48 mL, 4.3 mmol) in THF (5 mL) was added dropwise. After stirring for 1 h at room temperature the precipitate was filtered and the organic phase was evaporated. The residue was dissolved in methanol (20 mL), sodium bicarbonate (1 spatula) was added and the mixture was stirred at room temperature for 1 h. The solvent was evaporated and the residue was extracted (dichloromethane/water). Then the organic phase was dried over sodium sulfate and concentrated. Purification by chromatography (SiO$_2$, heptane/ethyl acetate=100:0 to 60:40) afforded the title compound (250 mg, 20%) (as the most polar component of two formed in the reaction) which was obtained as a white solid. MS: m/e=351.4 [M+H]$^+$.

EXAMPLE 28

N-[6-(5-Methyl-3-phenyl-isoxazol-4-ylmethoxy)-pyridazin-3-yl]-oxalamic acid methyl ester As described for example 18, 6-(5-methyl-3-phenyl-isoxazol-4-ylmethoxy)-pyridazin-3-ylamine (200 mg, 0.7 mmol)

was converted, using chloro-oxo-acetic acid methyl ester instead of methoxyacetyl chloride, to the title compound (88 mg, 44%) which was obtained as a white solid. MS: m/e=369.0 [M+H]+.

EXAMPLE 29

N-[6-(5-Methyl-3-phenyl-isoxazol-4-ylmethoxy)-pyridazin-3-yl]-malonamic acid methyl ester As described for example 18, 6-(5-methyl-3-phenyl-isoxazol-4-ylmethoxy)-pyridazin-3-ylamine (200 mg, 0.7 mmol) was converted, using chlorocarbonyl-acetic acid methyl ester instead of methoxyacetyl chloride, to the title compound (88 mg, 32%) which was obtained as a white solid. MS: m/e=383.3 [M+H]+.

EXAMPLE 30

N-[6-(5-Methyl-3-phenyl-isoxazol-4-ylmethoxy)-pyridazin-3-yl]-benzamide

As described for example 18, 6-(5-methyl-3-phenyl-isoxazol-4-ylmethoxy)-pyridazin-3-ylamine (280 mg, 1 mmol) was converted, using benzoyl chloride instead of methoxyacetyl chloride, to the title compound (250 mg, 65%) which was obtained as a white solid. MS: m/e=387.4 [M+H]−.

EXAMPLE 31

4-Methyl-N-[6-(5-methyl-3-phenyl-isoxazol-4-ylmethoxy)-pyridazin-3-yl]-benzamide As described for example 18, 6-(5-methyl-3-phenyl-isoxazol-4-ylmethoxy)-pyridazin-3-ylamine (280 mg, 1 mmol) was converted, using p-toluoyl chloride instead of methoxyacetyl chloride, to the title compound (320 mg, 80%) which was obtained as a white solid. MS: m/e=401.3 [M+H]−.

EXAMPLE 32

Furan-2-carboxylic acid [6-(5-methyl-3-phenyl-isoxazol-4-ylmethoxy)-pyridazin-3-yl]-amide As described for example 18, 6-(5-methyl-3-phenyl-isoxazol-4-ylmethoxy)-pyridazin-3-ylamine (280 mg, 1 mmol) was converted, using 2-furoyl chloride instead of methoxyacetyl chloride, to the title compound (330 mg, 86%) which was obtained as a white solid. MS: m/e=377.2 [M+H]−.

EXAMPLE 33

Isoxazole-5-carboxylic acid [6-(5-methyl-3-phenyl-isoxazol-4-ylmethoxy)-pyridazin-3-yl]-amide As described for example 18, 6-(5-methyl-3-phenyl-isoxazol-4-ylmethoxy)-pyridazin-3-ylamine (280 mg, 1 mmol) was converted, using isoxazole-5-carbonyl chloride instead of methoxyacetyl chloride, to the title compound (290 mg, 77%) which was obtained as a white solid. MS: m/e=378.2 [M+H]+.

EXAMPLE 34

[6-(5-Methyl-3-phenyl-isoxazol-4-ylmethoxy)-pyridazin-3-yl]-carbamic acid ethyl ester To a solution of 6-(5-methyl-3-phenyl-isoxazol-4-ylmethoxy)-pyridazin-3-ylamine (280 mg, 1 mmol) and p-N,N-dimethylaminopyridine (61 mg, 0.5 mmol) in pyridine (5 mL) was added ethyl chloroformate (0.11 mL, 1.2 mmol) at room temperature. The resulting mixture was stirred at room temperature for 5 h. After evaporation the residue was extracted with ethyl acetate/water and the organic phase was dried over sodium sulfate and concentrated. Chromatography (SiO$_2$, heptane/ethyl acetate=100:0 to 70:30) afforded the title compound (260 mg, 73%) as a white solid. MS: m/e=355.0 [M+H]+.

EXAMPLE 35

3-(5-Methyl-3-phenyl-isoxazol-4-ylmethoxy)-6-pyrrolidin-1-yl-pyridazine

To a solution of 3-chloro-6-(5-methyl-3-phenyl-isoxazol-4-ylmethoxy)-pyridazine (300 mg, 1.0 mmol) in toluene (5 mL) was added pyrrolidine (0.10 mL, 1.2 mmol), sodium tert-butoxide (115 mg, 1.2 mmol), (±)-2,2'-bis(diphenylphosphino)-1,1-binaphtalene (19 mg, 0.03 mmol) and tris(dibenzylideneacetone)dipalladium chloroform complex (10 mg, 0.01 mmol). The resulting mixture was heated at 110° C. for 55 min with microwave heating. Then the reaction mixture was concentrated and extracted (ethyl acetate/brine). The organic phase was dried over sodium sulfate, concentrated and chromatographed (SiO$_2$, dichloromethane:methanol=100:0 to 99:1) to afford the title compound as a light yellow oil (80 mg, 24%). MS: m/e=337.5 [M+H]−.

EXAMPLE 36

4-[6-(5-Methyl-3-phenyl-isoxazol-4-ylmethoxy)-pyridazin-3-yl]-morpholine

A mixture of 3-chloro-6-(5-methyl-3-phenyl-isoxazol-4-ylmethoxy)-pyridazine (150 mg, 0.5 mmol) and morpholine (0.17 mL, 2 mmol) was stirred at 116° C. for 4 h. After extraction with ethyl acetate/water the organic phase was concentrated and chromatographed (SiO$_2$, heptane/ethyl acetate=100:0 to 70:30) to afford the title compound as a white solid (40 mg, 23%). MS: m/e=353.3 [M+H]+.

EXAMPLE 37

Methyl-[6-(5-methyl-3-phenyl-isoxazol-4-ylmethoxy)-pyridazin-3-yl]-amine HCl

3-Iodo-6-(5-methyl-3-phenyl-isoxazol-4-ylmethoxy)-pyridazine (500 mg, 1.3 mmol) was dissolved in an ethanolic solution of methylamine (7.5 mL of a 33% solution, excess). After addition of copper(I) iodide (291 mg, 1.5 mmol) the mixture was stirred for 3 h at 50° C. Then the solvent was evaporated and the residue was stirred with ethyl acetate and saturated aqueous Seignette salt solution. The organic phase was dried with sodium sulfate and evaporated. Chromatography (SiO$_2$, heptane/ethyl acetate=100:0 to 0:100) afforded the free base of the title compound as a light yellow oil. It was crystallized as the white hydrochloride salt from methanol/ether (220 mg, 53%). MS: m/e=297.1 [M+H]+.

EXAMPLE 38

Dimethyl-[6-(5-methyl-3-phenyl-isoxazol-4-ylmethoxy)-pyridazin-3-yl]-amine

3-Iodo-6-(5-methyl-3-phenyl-isoxazol-4-ylmethoxy)-pyridazine (500 mg, 1.3 mmol) was dissolved in an ethanolic solution of dimethylamine (7.5 mL of a 33% solution, excess). After addition of copper(I) bromide (219 mg, 1.5 mmol) the mixture was stirred for 72 h at room temperature followed by heating to 50° C. for 3 h. Then the solvent was evaporated and the residue was stirred with ethyl acetate and saturated aqueous Seignette salt solution. The organic phase was dried with sodium sulfate and evaporated. Chromatography (SiO$_2$, heptane/ethyl acetate=100:0 to 10:90) afforded the title compound as a light yellow oil (30 mg, 8%). MS: m/e=311.1 [M+H]$^+$.

EXAMPLE 39

3-(3,5-Dimethyl-pyrazol-1-yl)-6-(5-methyl-3-phenyl-isoxazol-4-ylmethoxy)-pyridazine To a solution of (5-methyl-3-phenyl-isoxazol-4-yl)-methanol (76 mg, 0.40 mmol) in DMF (0.8 mL) cooled to 0° C. was added sodium hydride (55% dispersion in mineral oil, 19.2 g, 0.44 mmol). The mixture was stirred at room temperature for 1 h. After addition of 3-chloro-6-(3,5-dimethylpyrazol-1-yl)-pyridazine (91.8 mg, 0.44 mmol) the mixture was stirred at room temperature overnight. Then the mixture was evaporated, extracted (ethyl acetate/water) and the organic phase was dried with sodium sulfate and concentrated. Chromatography (SiO$_2$, heptane:ethanol=100:0 to 95:5) afforded the title compound (5.0 mg, 3%) as a white solid. MS: m/e=362.4 [M+H]$^+$.

EXAMPLE 40

5-Methyl-6-(5-methyl-3-phenyl-isoxazol-4-ylmethoxy)-pyridazine-3-carboxylic acid ethyl ester As described for example 5, a mixture of 3-chloro-5-methyl-6-(5-methyl-3-phenyl-isoxazol-4-ylmethoxy)-pyridazine and 3-chloro-4-methyl-6-(5-methyl-3-phenyl-isoxazol-4-ylmethoxy)-pyridazine (3:2, 347 mg, 1.10 mmol) instead of 3-chloro-6-(5-methyl-3-phenyl-isoxazol-4-ylmethoxy)-pyridazine was converted to the title compound (SiO$_2$, heptane:ethyl acetate=100:0 to 60:40, 106 mg, 46%) which was obtained as a light yellow oil. MS: m/e=354.2 [M+H]$^-$.

EXAMPLE 41

3-Chloro-4-methyl-6-(5-methyl-3-phenyl-isoxazol-4-ylmethoxy)-pyridazine

As described for example 4, (5-methyl-3-phenyl-4-isoxazolyl)methanol (5.00 g, 26.4 mmol) was converted using 3,6-dichloro-4-methylpyridazine instead of 3-chloro-6-methylpyridazine to the title compound (4.59 g, 55%) which was obtained as a yellow oil. MS: m/e=316.1 [M]$^+$.

EXAMPLE 42

4-Methyl-6-(5-methyl-3-phenyl-isoxazol-4-ylmethoxy)-pyridazine-3-carboxylic acid ethyl ester As described for example 5, a mixture of 3-chloro-5-methyl-6-(5-methyl-3-phenyl-isoxazol-4-ylmethoxy)-pyridazine and 3-chloro-4-methyl-6-(5-methyl-3-phenyl-isoxazol-4-ylmethoxy)-pyridazine (3:2, 347 mg, 1.10 mmol) instead of 3-chloro-6-(5-methyl-3-phenyl-isoxazol-4-ylmethoxy)-pyridazine was converted to the title compound (SiO$_2$, heptane:ethyl acetate=100:0 to 60:40, 114 mg, 49%) which was obtained as a light yellow solid. MS: m/e=354.2 [M+H]$^-$.

EXAMPLE 43

4-Methyl-6-(5-methyl-3-phenyl-isoxazol-4-ylmethoxy)-pyridazine-3-carboxylic acid As described for example 11a, 4-methyl-6-(5-methyl-3-phenyl-isoxazol-4-ylmethoxy)-pyridazine-3-carboxylic acid ethyl ester (2.30 g, 6.52 mmol), instead of 6-(5-methyl-3-phenyl-isoxazol-4-ylmethoxy)-pyridazine-3-carboxylic acid ethyl ester, was converted to the title compound (1.73 g, 82%) which was obtained as an off-white solid. MS: m/e=324.4 [M−H]$^-$.

EXAMPLE 44

4-Methyl-6-(5-methyl-3-phenyl-isoxazol-4-ylmethoxy)-pyridazine-3-carboxylic acid (tetrahydro-pyran-4-yl)-amide As described for example 11b, 4-methyl-6-(5-methyl-3-phenyl-isoxazol-4-ylmethoxy)-pyridazine-3-carboxylic acid (200 mg, 0.61 mmol), instead of 6-(5-methyl-3-phenyl-isoxazol-4-ylmethoxy)-pyridazine-3-carboxylic acid, was converted, using 4-amino-tetrahydropyran instead of thiomorpholine 1,1-dioxide, to the title compound (SiO$_2$, heptane:ethyl acetate=100:0 to 60:40, 156 mg, 62%) which was obtained as a white solid. MS: m/e=409.3 [M+H]$^-$.

EXAMPLE 45

4-Methyl-6-(5-methyl-3-phenyl-isoxazol-4-ylmethoxy)-pyridazine-3-carboxylic acid cyclopropylamide As described for example 44, 4-methyl-6-(5-methyl-3-phenyl-isoxazol-4-ylmethoxy)-pyridazine-3-carboxylic acid (200 mg, 0.61 mmol) was converted, using cyclopropylamine instead of 4-amino-tetrahydropyran, to the title compound (SiO$_2$, heptane:ethyl acetate=100:0 to 60:40, 122 mg, 54%) which was obtained as a white solid. MS: m/e=365.3 [M+H]$^-$.

EXAMPLE 46

4-Methyl-6-(5-methyl-3-phenyl-isoxazol-4-ylmethoxy)-pyridazine-3-carboxylic acid isopropylamide As described for example 44, 4-methyl-6-(5-methyl-3-phenyl-isoxazol-4-ylmethoxy)-pyridazine-3-carboxylic acid (200 mg, 0.61 mmol) was converted, using isopropylamine instead of 4-amino-tetrahydropyran, to the title compound (SiO$_2$, heptane:ethyl acetate=100:0 to 60:40, 90 mg, 40%) which was obtained as a white solid. MS: m/e=367.2 [M+H]$^+$.

EXAMPLE 47

(1,1-Dioxo-1λ6-thiomorpholin-4-yl)-[4-methyl-6-(5-methyl-3-phenyl-isoxazol-4-ylmethoxy)-pyridazin-3-yl]-methanone As described for example 44, 4-methyl-6-(5-methyl-3-phenyl-isoxazol-4-ylmethoxy)-pyridazine-3-carboxylic acid (200 mg, 0.61 mmol) was converted, using thiomorpholine 1,1-dioxide instead of 4-amino-tetrahydropyran, to the title compound (SiO$_2$, heptane:ethyl acetate=100:0 to 60:40, 195 mg, 72%) which was obtained as a colourless crystalline solid. MS: m/e=443.2 [M+H]$^-$.

EXAMPLE 48

3-Chloro-6-[3-(3-fluoro-phenyl)-5-methyl-isoxazol-4-ylmethoxy]-pyridazine a) (E)- and/or (Z)-3-Fluoro-benzaldehyde oxime To a suspension of 3-fluorobenzaldehyde (6.75 g, 54 mmol) and hydroxylamine hydrochloride (4.16 g, 60 mmol) in ethanol (4.3 mL) and water (13 mL) was added ice (25 g). Then a solution of sodium hydroxide (5.5 g, 138 mmol) in water (6.5 mL) was added dropwise within a 10 min period (temperature rises from −8° C. to +7° C.) whereupon most of the solid dissolves. After 30 min stirring at room temperature a white solid precipitated and the resulting mixture was then diluted with water and acidified with HCl (4 N). The white precipitate was then filtered off, washed with water and dried under high vacuum to afford the title compound (7.0 g, 93%) which was obtained as a white solid. MS m/e (EI): 139.1 [M].

b) (E)- and/or (Z)-N-Hydroxy-3-fluoro-benzenecarboximidoyl chloride

To a solution of (E)- and/or (Z)-3-fluoro-benzaldehyde oxime (6.9 g, 50 mmol) in DMF (50 mL) was added N-chlorosuccinimide (6.6 g, 50 mmol) portionwise over 1 h, keeping the temperature below 35° C. The reaction mixture was stirred at room temperature for 1 h. The mixture was then poured onto ice-water, and extracted with ethyl acetate. The combined organic layers were then washed with water and brine, dried over sodium sulfate and evaporated to afford the title compound (6.3 g, 73%) which was obtained as an off white solid. MS m/e (EI): 173.1 [M].

c) 3-(3-Fluoro-phenyl)-5-methyl-isoxazole-4-carboxylic acid ethyl ester

To a solution of (E)- and/or (Z)-N-hydroxy-3-fluoro-benzenecarboximidoyl chloride (11.1 g, 64 mmol) in diethyl-ether (151 mL) was added ethyl 2-butynoate (7.2 g, 7.5 mL, 64 mmol) at 0° C. followed by the dropwise addition of triethylamine (7.8 g, 10.7 mL, 77 mmol) and the resulting mixture allowed to warm up to room temperature overnight. The mixture was then poured onto ice-water, and extracted with diethylether. The combined organic layers were then washed with water and brine, dried over sodium sulfate and evaporated. Purification by chromatography (SiO$_2$, heptane:ethyl acetate=100:0 to 1:1) afforded the title compound (6.3 g, 39%) which was obtained as a white solid. MS: m/e=250.1 [M+H]$^+$.

d) [3-(3-Fluoro-phenyl)-5-methyl-isoxazol-4-yl]-methanol

To a solution of 3-(3-fluoro-phenyl)-5-methyl-isoxazole-4-carboxylic acid ethyl ester (6.18 g, 25 mmol) in THF (320 mL) was added portionwise lithiumaluminiumhydride (528 mg, 14 mmol) at 0° C. and the reaction mixture was stirred at room temperature for 3 h. The mixture was then cooled to 0° C. and water (518 μL) added followed by sodium hydroxide (15% solution, 518 μL) and then again water (1.5 mL) and the mixture then stirred overnight at room temperature. The precipitate was then filtered off and washed with THF. The combined washings and filtrate were then evaporated. Purification by chromatography (SiO$_2$, heptane:ethyl acetate=100:0 to 1:1) afforded the title compound (3.9 g, 75%) which was obtained as a yellow solid. MS: m/e=208.3 [M+H]$^+$.

e) 3-Chloro-6-[3-(3-fluoro-phenyl)-5-methyl-isoxazol-4-ylmethoxy]-pyridazine

To a suspension of sodium hydride (55% dispersion in mineral oil, 632 mg, 14 mmol) in THF (21 mL) was added a solution of [3-(3-fluoro-phenyl)-5-methyl-isoxazol-4-yl]-methanol (3.0 g, 14 mmol) in THF (42 mL) at 0° C. and the reaction mixture warmed to room temperature over 30 min. Then a solution of 3,6-dichloropyridazine (2.2 g, 14 mmol) in THF (42 mL) was added dropwise at 0° C. and the reaction mixture was stirred at room temperature for 3 h. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography (SiO$_2$, heptane:ethyl acetate=100:0 to 1:1) afforded the title compound (4.3 g, 92%) which was obtained as an off white solid. MS: m/e=320.0 [M+H]$^+$.

EXAMPLE 49

6-[3-(3-Fluoro-phenyl)-5-methyl-isoxazol-4-yl-methoxy]-pyridazine-3-carboxylic acid ethyl ester To a solution of 3-chloro-6-[3-(3-fluoro-phenyl)-5-methyl-isoxazol-4-ylmethoxy]-pyridazine (4.1 g, 13 mmol) in ethanol (65 mL) was added sodium carbonate (1.37 g, 13 mmol), 1,1'-bis(diphenylphosphino)ferrocene (716 mg, 1.3 mmol) and palladium(II) acetate (290 mg, 1.3 mmol). The resulting mixture was heated at 50° C. overnight under a carbon monoxide atmosphere. After cooling to room temperature the mixture was diluted with ethanol (100 mL), filtered through Celite® and concentrated. Purification by chromatography (SiO$_2$, heptane:ethyl acetate=100:0 to 1:1) afforded the title compound (3.2 g, 70%) as an off white solid. MS: m/e=358.0 [M+H]$^-$.

EXAMPLE 50

6-[3-(3-Fluoro-phenyl)-5-methyl-isoxazol-4-yl-methoxy]-pyridazine-3-carboxylic acid methylamide A solution of trimethylaluminium (2 M in toluene, 800 μL, 1.6 mmol) was added dropwise (exothermic) to a solution of methylamine (2 M in THF, 800 μL, 1.6 mmol) in dioxane (10 mL) and the resulting mixture was stirred at room temperature for 1 h. Then a solution of 6-[3-(3-fluoro-phenyl)-5-methyl-isoxazol-4-ylmethoxy]-pyridazine-3-carboxylic acid ethyl ester (143 mg, 0.4 mmol) in dioxane (5 mL) was added. The resulting mixture was heated at 85-95° C. for 18 h, cooled to room temperature, poured into a sodium potassium tartrate solution and extracted with ethyl acetate which was then washed with brine, dried over sodium sulfate and evaporated. Purification by chromatography (SiO$_2$, heptane:ethyl acetate=100:0 to 1:1) afforded the title compound (122 mg, 99%) which was obtained as a white solid. MS: m/e=343.3 [M+H]$^-$.

EXAMPLE 51

6-[3-(3-Fluoro-phenyl)-5-methyl-isoxazol-4-yl-methoxy]-pyridazine-3-carboxylic acid ethylamide As described for example 50, 6-[3-(3-fluoro-phenyl)-5-methyl-isoxazol-4-ylmethoxy]-pyridazine-3-carboxylic acid ethyl ester (143 mg, 0.4 mmol) was converted, using ethylamine instead of methylamine, to the title compound (87 mg, 61%) which was obtained as a white solid. MS: m/e=357.3 $[M+H]^+$.

EXAMPLE 52

6-[3-(3-Fluoro-phenyl)-5-methyl-isoxazol-4-yl-methoxy]-pyridazine-3-carboxylic acid (2-hydroxy-ethyl)-amide A solution of trimethylaluminium (2 M in toluene, 800 µL, 1.6 mmol) was added dropwise (exothermic) to a solution of ethanolamine (96 µL, 1.6 mmol) in dioxane (10 mL) and the resulting mixture was stirred at room temperature for 1 h. Then a solution of 6-[3-(3-fluoro-phenyl)-5-methyl-isoxazol-4-ylmethoxy]-pyridazine-3-carboxylic acid ethyl ester (143 mg, 0.4 mmol) in dioxane (5 mL) was added. The resulting mixture was then heated at 85-95° C. for 2 h, cooled to room temperature, poured into a sodium potassium tartrate solution and extracted with ethyl acetate which was then washed with brine, dried over sodium sulfate and evaporated. Purification by chromatography ($SiO_2$, heptane:ethyl acetate=100:0 to 0:100) afforded the title compound (36 mg, 24%) which was obtained as a white solid. MS: m/e=373.1 $[M+H]^+$.

EXAMPLE 53

6-[3-(3-Fluoro-phenyl)-5-methyl-isoxazol-4-yl-methoxy]-pyridazine-3-carboxylic acid (2,2,2-trifluoro-ethyl)-amide As described for example 52, 6-[3-(3-fluoro-phenyl)-5-methyl-isoxazol-4-ylmethoxy]-pyridazine-3-carboxylic acid ethyl ester (143 mg, 0.4 mmol) was converted, using 2,2,2-trifluoroethylamine instead of ethanolamine, to the title compound (127 mg, 77%) which was obtained as an off-white solid. MS: m/e=411.1 $[M+H]^+$.

EXAMPLE 54

6-[3-(3-Fluoro-phenyl)-5-methyl-isoxazol-4-yl-methoxy]-pyridazine-3-carboxylic acid isopropylamide As described for example 52, 6-[3-(3-fluoro-phenyl)-5-methyl-isoxazol-4-ylmethoxy]-pyridazine-3-carboxylic acid ethyl ester (143 mg, 0.4 mmol) was converted, using isopropylamine instead of ethanolamine, to the title compound (58 mg, 39%) which was obtained as a white solid after recrystallisation from heptane:ethyl acetate. MS: m/e=371.0 $[M+H]^+$.

EXAMPLE 55

6-[3-(3-Fluoro-phenyl)-5-methyl-isoxazol-4-yl-methoxy]-pyridazine-3-carboxylic acid cyclopropylamide As described for example 52, 6-[3-(3-fluoro-phenyl)-5-methyl-isoxazol-4-ylmethoxy]-pyridazine-3-carboxylic acid ethyl ester (143 mg, 0.4 mmol) was converted, using cyclopropylamine instead of ethanolamine, to the title compound (122 mg, 83%) which was obtained as an off white solid. MS: m/e=369.0 $[M+H]^+$.

EXAMPLE 56

6-[3-(3-Fluoro-phenyl)-5-methyl-isoxazol-4-yl-methoxy]-pyridazine-3-carboxylic acid (tetrahydro-pyran-4-yl)-amide A solution of trimethylaluminium (2 M in toluene, 800 µL, 1.6 mmol) was added dropwise (exothermic) to a solution of 4-aminotetrahydrofuran (162 mg, 1.6 mmol) in dioxane (10 mL) and the resulting mixture was stirred at room temperature for 1 h. Then a solution of 6-[3-(3-fluoro-phenyl)-5-methyl-isoxazol-4-ylmethoxy]-pyridazine-3-carboxylic acid ethyl ester (143 mg, 0.4 mmol) in dioxane (5 mL) was added. The resulting mixture was then heated at 85-95° C. for 4 h, cooled to room temperature, poured into a sodium potassium tartrate solution and extracted with ethyl acetate which was then washed with brine, dried over sodium sulfate and evaporated. Purification by chromatography ($SiO_2$, heptane:ethyl acetate=100:0 to 0:100) afforded the title compound (146 mg, 89%) which was obtained as an off white solid. MS: m/e=413.1 $[M+H]^-$.

EXAMPLE 57

3-Chloro-6-[3-(4-fluoro-phenyl)-5-methyl-isoxazol-4-ylmethoxy]-pyridazine a) (E)- and/or (Z)-4-Fluoro-benzaldehyde oxime As described for example 48a, 4-fluorobenzaldehyde (24.8 g, 200 mmol) was converted, instead of 3-fluorobenzaldehyde, to the title compound (23.3 g, 84%) which was obtained as a white solid. MS: m/e=139.1 $[M]^+$.

b) (E)- and/or (Z)-N-Hydroxy-4-fluoro-benzenecarboximidoyl chloride

As described for example 48b, (E)- and/or (Z)-4-fluorobenzaldehyde oxime 4-fluorobenzaldehyde (23.3 g, 167 mmol) was converted, instead of (E)- and/or (Z)-3-fluorobenzaldehyde oxime, to the title compound (25.9 g, 89%) which was obtained as an off white solid. MS: m/e=173.0 $[M]^+$.

c) 3-(4-Fluoro-phenyl)-5-methyl-isoxazole-4-carboxylic acid ethyl ester

As described for example 48c, (E)- and/or (Z)-N-hydroxy-4-fluoro-benzenecarboximidoyl chloride (15.4 g, 89 mmol) was converted, instead of (E)- and/or (Z)-N-hydroxy-3-fluoro-benzenecarboximidoyl chloride, to the title compound (9.8 g, 44%) which was obtained as an off white solid. MS: m/e=250.1 $[M+H]^+$.

d) [3-(4-Fluoro-phenyl)-5-methyl-isoxazol-4-yl]-methanol

As described for example 48d, 3-(4-fluoro-phenyl)-5-methyl-isoxazole-4-carboxylic acid ethyl ester (3.0 g, 12 mmol) was converted, instead of 3-(3-fluoro-phenyl)-5-methylisoxazole-4-carboxylic acid ethyl ester, to the title compound (1.8 g, 71%) which was obtained as a white solid. MS: m/e=208.1 [M+H]$^+$.

e) 3-Chloro-6-[3-(4-fluoro-phenyl)-5-methyl-isoxazol-4-ylmethoxy]-pyridazine

As described for example 48e, [3-(4-fluoro-phenyl)-5-methyl-isoxazol-4-yl]-methanol (2.8 g, 14 mmol) was converted, instead of [3-(3-fluoro-phenyl)-5-methyl-isoxazol-4-yl]-methanol, to the title compound (3.2 g, 74%) which was obtained as a white solid. MS: m/e=319.9 [M+H].

EXAMPLE 58

6-[3-(4-Fluoro-phenyl)-5-methyl-isoxazol-4-ylmethoxy]-pyridazine-3-carboxylic acid ethyl ester As described for example 49, 3-chloro-6-[3-(4-fluoro-phenyl)-5-methyl-isoxazol-4-ylmethoxy]-pyridazine (308 mg, 9.6 mmol) was converted, instead of 3-chloro-6-[3-(3-fluoro-phenyl)-5-methyl-isoxazol-4-ylmethoxy]-pyridazine, to the title compound (281 mg, 82%) which was obtained as a white solid. MS: m/e=358.0 [M+H]$^+$.

EXAMPLE 59

6-[3-(4-Fluoro-phenyl)-5-methyl-isoxazol-4-ylmethoxy]-pyridazine-3-carboxylic acid cyclopropyl-methyl-amide As described for example 50, 6-[3-(4-fluoro-phenyl)-5-methyl-isoxazol-4-ylmethoxy]-pyridazine-3-carboxylic acid ethyl ester (143 mg, 0.4 mmol), instead of 6-[3-(3-fluoro-phenyl)-5-methyl-isoxazol-4-ylmethoxy]-pyridazine-3-carboxylic acid ethyl ester, was converted, using aminomethylcyclopropane instead of methylamine, to the title compound (39 mg, 26%) which was obtained as a white solid. MS: m/e=383.1 [M+H]$^+$.

EXAMPLE 60

6-[3-(4-Fluoro-phenyl)-5-methyl-isoxazol-4-ylmethoxy]-pyridazine-3-carboxylic acid (2,2,2-trifluoro-ethyl)-amide As described for example 59, 6-[3-(4-fluoro-phenyl)-5-methyl-isoxazol-4-ylmethoxy]-pyridazine-3-carboxylic acid ethyl ester (143 mg, 0.4 mmol) was converted, using 2,2,2-trifluoroethylamine instead of aminomethylcyclopropane, to the title compound (119 mg, 73%) which was obtained as a white solid. MS: m/e=411.1 [M+H]$^+$.

EXAMPLE 61

6-[3-(4-Fluoro-phenyl)-5-methyl-isoxazol-4-ylmethoxy]-pyridazine-3-carboxylic acid isopropylamide A solution of trimethylaluminium (2 M in toluene, 800 µL, 1.6 mmol) was added dropwise (exothermic) to a solution of isopropylamine (95 mg, 137 µL, 1.6 mmol) in dioxane (10 mL) and the resulting mixture was stirred at room temperature for 1 h. Then a solution of 6-[3-(3-fluoro-phenyl)-5-methyl-isoxazol-4-ylmethoxy]-pyridazine-3-carboxylic acid ethyl ester (143 mg, 0.4 mmol) in dioxane (5 mL) was added. The resulting mixture was heated at 85-95° C. for 6 h, cooled to room temperature, poured into a sodium potassium tartrate solution and extracted with ethyl acetate which was then washed with brine, dried over sodium sulfate and evaporated. Purification by chromatography (SiO$_2$, heptane:ethyl acetate=100:0 to 0:100) afforded the title compound (105 mg, 71%) which was obtained as a white solid. MS: m/e=371.3 [M+H]$^-$.

EXAMPLE 62

6-[3-(4-Fluoro-phenyl)-5-methyl-isoxazol-4-ylmethoxy]-pyridazine-3-carboxylic acid cyclopropylamide As described for example 59, 6-[3-(4-fluoro-phenyl)-5-methyl-isoxazol-4-ylmethoxy]-pyridazine-3-carboxylic acid ethyl ester (143 mg, 0.4 mmol) was converted, using cyclopropylamine instead of aminomethylcyclopropane, to the title compound (118 mg, 80%) which was obtained as a white solid. MS: m/e=369.1 [M+H]$^+$.

EXAMPLE 63

6-[3-(4-Fluoro-phenyl)-5-methyl-isoxazol-4-ylmethoxy]-pyridazine-3-carboxylic acid (tetrahydro-pyran-4-yl)-amide As described for example 59, 6-[3-(4-fluoro-phenyl)-5-methyl-isoxazol-4-ylmethoxy]-pyridazine-3-carboxylic acid ethyl ester (143 mg, 0.4 mmol) was converted, using 4-aminotetrahydropyran instead of aminomethylcyclopropane, to the title compound (120 mg, 73%) which was obtained as a white solid after recrystallization from heptane:ethyl acetate. MS: m/e=413.3 [M+H].

EXAMPLE 64

{6-[3-(4-Fluoro-phenyl)-5-methyl-isoxazol-4-ylmethoxy]-pyridazin-3-yl}-morpholin-4-yl-methanone As described for example 59, 6-[3-(4-fluoro-phenyl)-5-methyl-isoxazol-4-ylmethoxy]-pyridazine-3-carboxylic acid ethyl ester (143 mg, 0.4 mmol) was converted, using morpholine instead of aminomethylcyclopropane, to the title compound (132 mg, 83%) which was obtained as a light yellow solid. MS: m/e=399.1 [M+H]$^+$.

EXAMPLE 65

{6-[3-(4-Fluoro-phenyl)-5-methyl-isoxazol-4-ylmethoxy]-pyridazin-3-yl}-thiomorpholin-4-yl-methanone As described for example 59, 6-[3-(4-fluoro-phenyl)-5-methyl-isoxazol-4-ylmethoxy]-pyridazine-3-carboxylic acid ethyl ester (143 mg, 0.4 mmol) was converted, using thiomorpholine instead of aminomethylcyclopropane, to the title compound (140 mg, 85%) which was obtained as an off-white solid. MS: m/e=415.4 [M+H]$^+$.

EXAMPLE 66

(1,1-Dioxo-1λ6-thiomorpholin-4-yl)-{6-[3-(4-fluoro-phenyl)-5-methyl-isoxazol-4-ylmethoxy]-pyridazin-3-yl}-methanone As described for example 59, 6-[3-(4-fluoro-phenyl)-5-methyl-isoxazol-4-ylmethoxy]-pyridazine-3-carboxylic acid ethyl ester (143 mg, 0.4 mmol) was converted, using thiomorpholine-S,S-dioxide instead of aminomethylcyclopropane, to the title compound (131 mg, 73%) which was obtained as an off white solid. MS: m/e=447.1 $[M+H]^+$.

EXAMPLE 67

6-(5-Methyl-3-pyridin-4-yl-isoxazol-4-ylmethoxy)-pyridazine-3-carboxylic acid cyclopropylmethyl-amide a) 5-Methyl-3-pyridin-4-yl-isoxazole-4-carboxylic acid ethyl ester To a suspension of N-chlorosuccinimide (10.9 g, 81.9 mmol) in chloroform (50 mL) was added pyridine (0.66 mL, 8.2 mmol) and a solution of pyridine-4-carboxaldoxime (10.0 g, 81.2 mmol) in chloroform (150 mL) during 15 min at ambient temperature. After stirring for 30 min at this temperature a solution of ethyl (E)-3-(1-pyrrolidino)-2-butenoate (15.0 g, 81.9 mmol) in chloroform (10 mL) was added. The resulting suspension was warmed to 50° C. and a solution of triethylamine (12 mL, 86 mmol) in chloroform (10 mL) was added dropwise over a period of 1 h. Stirring was continued for 0.5 h at 50° C. and for 30 h at ambient temperature. The dark brown solution was washed with water (100 mL) and the aqueous layers were extracted with dichloromethane (50 mL) and dried over sodium sulfate. Concentration was followed by trituration of the residue in a mixture of tert-butylmethyl-ether and heptane (1:1, 20 mL) affording the title compound (8.1 g, 24%) as a brown solid. MS: m/e=233.1 $[M+H]^+$.

b) (5-Methyl-3-pyridin-4-yl-isoxazol-4-yl)-methanol

To a solution of 5-methyl-3-pyridin-4-yl-isoxazole-4-carboxylic acid ethyl ester (7.1 g, 17.3 mmol) in THF (350 mL) was added at 5° C. lithium aluminum hydride (635 mg, 16.7 mmol). After stirring for 2 h at this temperature further lithium aluminum hydride (318 mg, 8.4 mmol) was added and stirred for 1 h at 5° C. Water (1.9 mL) was added carefully followed by aqueous sodium hydroxide (15%, 1.9 mL) and water (0.54 mL). The resulting suspension was stirred for 15 min at ambient temperature and filtered over Hyflo®. Concentration and purification by chromatography ($SiO_2$, heptane:ethyl acetate=50:50 to 0:100) afforded the title compound (2.15 g, 65%) as a light yellow solid. MS: m/e=191.2 $[M+H]^+$.

c) 3-Chloro-6-(5-methyl-3-pyridin-4-yl-isoxazol-4-ylmethoxy)-pyridazine

As described for example 48e, (5-methyl-3-pyridin-4-yl-isoxazol-4-yl)-methanol (2.8 g, 14 mmol) was converted, instead of [3-(3-fluoro-phenyl)-5-methyl-isoxazol-4-yl]-methanol, to the title compound (3.2 g, 74%) which was obtained as a white solid. MS: m/e=303.0 $[M+H]^+$.

d) 6-(5-Methyl-3-pyridin-4-yl-isoxazol-4-ylmethoxy)-pyridazine-3-carboxylic acid ethyl ester As described for example 49, 3-chloro-6-(5-methyl-3-pyridin-4-yl-isoxazol-4-ylmethoxy)-pyridazine (3.8 g, 12 mmol) was converted, instead of 3-chloro-6-[3-(3-fluoro-phenyl)-5-methyl-isoxazol-4-ylmethoxy]-pyridazine, to the title compound (1.5 g, 35%) which was obtained as an orange solid. MS: m/e=341.3 $[M+H]^+$.

e) 6-(5-Methyl-3-pyridin-4-yl-isoxazol-4-ylmethoxy)-pyridazine-3-carboxylic acid cyclopropyl-methyl-amide A solution of trimethylaluminium (2 M in toluene, 587 μL, 1.2 mmol) was added dropwise (exothermic) to a solution of aminomethylcyclopropane (85 mg, 101 μL, 1.2 mmol) in dioxane (6 mL) and the resulting mixture was stirred at room temperature for 1 h. Then a solution of 6-(5-methyl-3-pyridin-4-yl-isoxazol-4-ylmethoxy)-pyridazine-3-carboxylic acid ethyl ester (100 mg, 0.29 mmol) in dioxane (4 mL) was added. The resulting mixture was heated at 85-95° C. for 3 h, cooled to room temperature, poured into a sodium potassium tartrate solution and extracted with ethyl acetate which was then washed with brine, dried over sodium sulfate and evaporated. Purification by chromatography ($SiO_2$, heptane:ethyl acetate=100:0 to 0:100) afforded the title compound (78 mg, 73%) which was obtained as a light yellow solid. MS: m/e=366.3 $[M+H]^-$.

EXAMPLE 68

6-(5-Methyl-3-pyridin-4-yl-isoxazol-4-ylmethoxy)-pyridazine-3-carboxylic acid (2,2,2-trifluoro-ethyl)-amide As described for example 67e, 6-(5-methyl-3-pyridin-4-yl-isoxazol-4-ylmethoxy)-pyridazine-3-carboxylic acid ethyl ester (100 mg, 0.29 mmol) was converted, using 2,2,2-trifluoroethylamine instead of aminomethylcyclopropane, to the title compound (76 mg, 66%) which was obtained as a white solid. MS: m/e=394.1 $[M+H]^+$.

EXAMPLE 69

6-(5-Methyl-3-pyridin-4-yl-isoxazol-4-ylmethoxy)-pyridazine-3-carboxylic acid isopropylamide As described for example 50, 6-(5-methyl-3-pyridin-4-yl-isoxazol-4-ylmethoxy)-pyridazine-3-carboxylic acid ethyl ester (100 mg, 0.29 mmol), instead of 6-[3-(3-fluoro-phenyl)-5-methyl-isoxazol-4-ylmethoxy]-pyridazine-3-carboxylic acid ethyl ester, was converted, using isopropylamine instead of methylamine, to the title compound (19 mg, 18%) which was obtained as a white solid. MS: m/e=354.3 $[M+H]^+$.

EXAMPLE 70

6-(5-Methyl-3-pyridin-4-yl-isoxazol-4-ylmethoxy)-pyridazine-3-carboxylic acid cyclopropylamide As described for example 69, 6-(5-methyl-3-pyridin-4-yl-isoxazol-4-ylmethoxy)-pyridazine-3-carboxylic acid ethyl ester (100 mg, 0.29 mmol) was converted, using cyclopropylamine instead of isopropylamine, to the title compound (85 mg, 82%) which was obtained as a light brown solid. MS: m/e=352.3 $[M+H]^+$.

EXAMPLE 71

6-(5-Methyl-3-pyridin-4-yl-isoxazol-4-ylmethoxy)-pyridazine-3-carboxylic acid (tetrahydro-pyran-4-yl)-amide As described for example 69, 6-(5-methyl-3-pyridin-4-yl-isoxazol-4-ylmethoxy)-pyridazine-3-carboxylic acid ethyl ester (100 mg, 0.29 mmol) was converted, using 4-aminotet-

EXAMPLE 72

(6-Chloro-pyridazin-3-yl)-(5-methyl-3-phenyl-isoxazol-4-ylmethyl)-amine

A solution of (5-methyl-3-phenyl-isoxazol-4-yl)-methylamine (190 mg, 1 mmol) and 3,6-dichloropyridazine (150 mg, 1 mmol) in ethanol (5 mL) was heated under reflux for 96 h. The mixture was evaporated, extracted (dichloromethane/water) and the organic phase was dried with sodium sulfate and concentrated. Chromatography (SiO$_2$, heptane:ethyl acetate=100:0 to 40:60) and trituration with hexane afforded the title compound (40 mg, 13%) as a white solid. MS: m/e=301.1 [M+H]$^+$.

EXAMPLE 73

6-[(5-Methyl-3-phenyl-isoxazol-4-ylmethyl)-amino]-pyridazine-3-carboxylic acid cyclopropylmethyl-amide a) (6-Iodo-pyridazine-3-yl)-(5-methyl-3-phenyl-isoxazol-4ylmethyl)-amine As described for example 72, (5-methyl-3-phenyl-isoxazol-4-yl)-methylamine (2.0 g, 10.6 mmol) was converted using 3-chloro-6-iodopyridazine (Goodman, A. J.; Stanforth, S. P.; Tarbit, B. *Tetrahedron* 1999, 55, 15067) instead of 3,6-dichloropyridazine to the title compound (1.0 g, 24%) which was contaminated with ca. 33% of (6-chloro-pyridazin-3-yl)-(5-methyl-3-phenyl-isoxazol-4-ylmethyl)-amine (example 72). The product was obtained as a white solid. MS: m/e=393.0 [M+H]$^+$.

b) 6-[(5-Methyl-3-phenyl-isoxazol-4-ylmethyl)-amino]-pyridazine-3-carboxylic acid methyl ester To a solution of (6-iodo-pyridazine-3-yl)-(5-methyl-3-phenyl-isoxazol-4ylmethyl)-amine (1.0 g, 2.6 mmol) in methanol (3 mL) was added sodium carbonate (270 mg, 2.6 mmol), 1,1'-bis(diphenylphosphino)ferrocene (141 mg, 0.26 mmol) and palladium(II) acetate (57 mg, 0.26 mmol). The resulting mixture was heated at 50° C. for 16 h under a carbon monoxide atmosphere. After cooling to room temperature it was filtered through Celite® and concentrated. Purification by chromatography (SiO$_2$, heptane:ethyl acetate=100:0 to 20:80) afforded the title compound (720 mg, 87%) as a light brown solid. MS: m/e=325.3 [M+H]$^+$.

c) 6-[(5-Methyl-3-phenyl-isoxazol-4-ylmethyl)-amino]-pyridazine-3-carboxylic acid cyclopropylmethyl-amide To a solution of aminomethylcyclopropane (0.11 mL, 1.2 mmol) in dioxane (5 mL) was added dropwise trimethylaluminum solution (2 M solution in hexane, 0.62 mL, 1.24 mmol). After stirring for 1 h at room temperature a suspension of 6-[(5-methyl-3-phenyl-isoxazol-4-ylmethyl)-amino]-pyridazine-3-carboxylic acid methyl ester (100 mg, 0.3 mmol) in dioxane (5 mL) was added. The reaction mixture was stirred at 90° C. for 2 h, cooled to room temperature and poured into water. Extraction (ethyl acetate/saturated aqueous Seignette salt solution) followed by drying of the organic phase over sodium sulfate and evaporation afforded an oil. Purification by chromatography (SiO$_2$, heptane:ethyl acetate=100:0 to 0:100) afforded the title compound (60 mg, 54%) which was obtained as a light yellow foam. MS: m/e=364.5 [M+H]$^+$.

EXAMPLE 74

6-[(5-Methyl-3-phenyl-isoxazol-4-ylmethyl)-amino]-pyridazine-3-carboxylic acid (2,2,2-trifluoro-ethyl)-amide As described for example 73c, 6-[(5-methyl-3-phenyl-isoxazol-4-ylmethyl)-amino]-pyridazine-3-carboxylic acid methyl ester (100 mg, 0.3 mmol) was converted, using 2,2,2-trifluoroethylamine instead of aminomethylcyclopropane, to the title compound (86 mg, 71%) which was obtained as a light yellow foam. MS: m/e=428.1 [M+H]$^+$.

EXAMPLE 75

6-[(5-Methyl-3-phenyl-isoxazol-4-ylmethyl)-amino]-pyridazine-3-carboxylic acid isopropylamide To a solution of (6-iodo-pyridazine-3-yl)-(5-methyl-3-phenyl-isoxazol-4ylmethyl)-amine (300 mg, 0.76 mmol) in DMF (3 mL) was added isopropylamine (0.66 ml, 7.6 mmol), triphenylphosphine (20 mg, 0.08 mmol) and palladium(II) acetate (17 mg, 0.08 mmol). The resulting mixture was stirred at room temperature for 16 h under a carbon monoxide atmosphere. After evaporation of the solvent the residue was extracted (ethyl acetate/water). The organic phase was dried over sodium sulfate and concentrated. Purification by chromatography (SiO$_2$, heptane:ethyl acetate=100:0 to 20:80) to afford the title compound (55 mg, 20%) as a light yellow oil. MS: m/e=352.3 [M+H]$^+$.

EXAMPLE 76

6-[(5-Methyl-3-phenyl-isoxazol-4-ylmethyl)-amino]-pyridazine-3-carboxylic acid cyclopropylamide As described for example 75, (6-iodo-pyridazine-3-yl)-(5-methyl-3-phenyl-isoxazol-4ylmethyl)-amine (300 mg, 0.76 mmol) was converted, using cyclopropylamine instead of isopropylamine, to the title compound (65 mg, 24%) which was obtained as a light yellow foam. MS: m/e=350.5 [M+H]$^+$.

EXAMPLE 77

6-[(5-Methyl-3-phenyl-isoxazol-4-ylmethyl)-amino]-pyridazine-3-carboxylic acid (tetrahydro-pyran-4-yl)-amide As described for example 73c, 6-[(5-methyl-3-phenyl-isoxazol-4-ylmethyl)-amino]-pyridazine-3-carboxylic acid methyl ester (100 mg, 0.3 mmol) was converted, using 4-aminotetrahydropyran instead of aminomethylcyclopropane, to the title compound (95 mg, 78%) which was obtained as a light yellow foam. MS: m/e=394.3 [M+H]$^+$.

EXAMPLE 78

(6-Chloro-pyridazin-3-yl)-[3-(4-fluoro-phenyl)-5-methyl-isoxazol-4-ylmethyl]-amine a) 2-[3-(4-Fluoro-phenyl)-5-methyl-isoxazol-4-ylmethyl]-isoindole-1,3-dione To a solution of [3-(4-fluoro-phenyl)-5-methyl-isoxazol-4-yl]-methanol (5.0 g, 24 mmol) in THF (290 mL) was added (continued from previous page: rahydropyran instead of isopropylamine, to the title compound (39 mg, 34%) which was obtained as a white foam. MS: m/e=396.4 [M+H]$^+$.)

phthalimide (4.7 g, 32 mmol) and triphenylphosphine (8.4 g, 32 mmol) at ambient temperature under an argon atmosphere. Then a solution of diethyl azodicarboxylate (40% in toluene, 12.5 mL, 32 mmol) was added and the reaction mixture was stirred for 1 h at room temperature. Concentration and repeated trituration and then purification by chromatography (SiO$_2$, heptane:ethyl acetate=100:0 to 1:1) afforded the title compound (6.0 g, 74%) as a white solid. MS: m/e=337.1 [M+H]$^+$.

b) C-[3-(4-Fluoro-phenyl)-5-methyl-isoxazol-4-yl]-methylamine

To a solution of 2-[3-(4-fluoro-phenyl)-5-methyl-isoxazol-4-ylmethyl]-isoindole-1,3-dione (5.9 g, 18 mmol) in THF (248 mL) and ethanol (21 mL) at 0° C. was added hydrazine hydrate (6.7 g, 6.5 mL, 134 mmol) and the resulting mixture stirred at room temperature overnight. The mixture was then filtered and the filtrate diluted with HCl (1 N) and extracted with ethyl acetate. The combined organic extracts were then washed with HCl (1 N) and the aqueous layer made basic with NaOH (6 N). The aqueous layers were extracted with ethyl acetate and the combined organic layers washed with brine and dried over sodium sulfate. Concentration afforded the title compound (2.0 g, 54%) as a light yellow oil. MS: m/e=190.3 [M+H]$^+$.

c) (6-Chloro-pyridazin-3-yl)-[3-(4-fluoro-phenyl)-5-methyl-isoxazol-4-ylmethyl]-amine A solution of C-[3-(4-fluoro-phenyl)-5-methyl-isoxazol-4-yl]-methylamine (206 mg, 1.0 mmol) and 3,6-dichloropyridazine (149 mg, 1.0 mmol) in DMSO (2 mL) containing N,N-diisopropyl ethyl amine (259 mg, 342 μL, 2.0 mmol) was heated with microwave irradiation to 160° C. for 1 h. After cooling to room temperature the reaction mixture was extracted (ethyl acetate/water). The organic phase was dried over sodium sulfate and concentrated. Purification by chromatography (SiO$_2$, heptane:ethyl acetate=100:0 to 1:1) afforded the title compound (99 mg, 31%) as an off white solid after recrystallization from heptane:ethyl acetate. MS: m/e=319.1 [M+H]$^-$.

EXAMPLE 79

6-{[3-(4-Fluoro-phenyl)-5-methyl-isoxazol-4-ylmethyl]-amino}-pyridazine-3-carboxylic acid ethyl ester As described for example 49, (6-chloro-pyridazin-3-yl)-[3-(4-fluoro-phenyl)-5-methyl-isoxazol-4-ylmethyl]-amine (1.1 g, 3.5 mmol) was converted, instead of 3-chloro-6-[3-(3-fluoro-phenyl)-5-methyl-isoxazol-4-ylmethoxy]-pyridazine, to the title compound (1.1 g, 91%) which was obtained as a light red solid. MS: m/e=357.3 [M+H]$^-$.

EXAMPLE 80

6-{[3-(4-Fluoro-phenyl)-5-methyl-isoxazol-4-ylmethyl]-amino}-pyridazine-3-carboxylic acid (2-hydroxy-ethyl)-amide A solution of trimethylaluminium (2 M in toluene, 500 μL, 1.0 mmol) was added dropwise (exothermic) to a solution of ethanolamine (61 mg, 60 μL, 1.0 mmol) in dioxane (6 mL) and the resulting mixture was stirred at room temperature for 1 h. Then a solution of 6-{[3-(4-fluoro-phenyl)-5-methyl-isoxazol-4-ylmethyl]-amino}-pyridazine-3-carboxylic acid ethyl ester (89 mg, 0.25 mmol) in dioxane (3 mL) was added. The resulting mixture was then heated at 85-95° C. for 4 h and then cooled to room temperature and then poured into a sodium potassium tartrate solution and extracted with ethyl acetate which was then washed with brine, dried over sodium sulfate and evaporated. Purification by chromatography (SiO$_2$, dichloromethane:methanol=100:0 to 9:1) afforded the title compound (19 mg, 20%) which was obtained as a light yellow foam. MS: m/e=372.3 [M+H]$^+$.

EXAMPLE 81

6-{[3-(4-Fluoro-phenyl)-5-methyl-isoxazol-4-ylmethyl]-amino}-pyridazine-3-carboxylic acid cyclopropylmethyl-amide As described for example 73c, 6-{[3-(4-fluoro-phenyl)-5-methyl-isoxazol-4-ylmethyl]-amino}-pyridazine-3-carboxylic acid ethyl ester (89 mg, 0.25 mmol) was converted, instead of 6-[(5-methyl-3-phenyl-isoxazol-4-ylmethyl)-amino]-pyridazine-3-carboxylic acid methyl ester, to the title compound (87 mg, 91%) which was obtained as an off white foam. MS: m/e=382.4 [M+H]$^+$.

EXAMPLE 82

6-{[3-(4-Fluoro-phenyl)-5-methyl-isoxazol-4-ylmethyl]-amino}-pyridazine-3-carboxylic acid (2,2,2-trifluoro-ethyl)-amide As described for example 81, 6-{[3-(4-fluoro-phenyl)-5-methyl-isoxazol-4-ylmethyl]-amino}-pyridazine-3-carboxylic acid ethyl ester (89 mg, 0.25 mmol) was converted, using 2,2,2-trifluoroethylamine instead of aminomethylcyclopropane, to the title compound (91 mg, 89%) which was obtained as an off white solid. MS: m/e=410.3 [M+H]$^+$.

EXAMPLE 83

6-{[3-(4-Fluoro-phenyl)-5-methyl-isoxazol-4-ylmethyl]-amino}-pyridazine-3-carboxylic acid isopropylamide As described for example 81, 6-{[3-(4-fluoro-phenyl)-5-methyl-isoxazol-4-ylmethyl]-amino}-pyridazine-3-carboxylic acid ethyl ester (89 mg, 0.25 mmol) was converted, using isopropylamine instead of aminomethylcyclopropane, to the title compound (49 mg, 53%) which was obtained as a white foam. MS: m/e=370.3 [M+H]$^+$.

EXAMPLE 84

6-{[3-(4-Fluoro-phenyl)-5-methyl-isoxazol-4-ylmethyl]-amino}-pyridazine-3-carboxylic acid cyclopropylamide As described for example 81, 6-{[3-(4-fluoro-phenyl)-5-methyl-isoxazol-4-ylmethyl]-amino}-pyridazine-3-carboxylic acid ethyl ester (89 mg, 0.25 mmol) was converted, using cyclopropylamine instead of aminomethylcyclopropane, to the title compound (61 mg, 66%) which was obtained as a white foam. MS: m/e=368.1 [M+H]$^+$.

EXAMPLE 85

6-{[3-(4-Fluoro-phenyl)-5-methyl-isoxazol-4-ylmethyl]-amino}-pyridazine-3-carboxylic acid (tetrahydro-pyran-4-yl)-amide As described for example 81, 6-{[3-(4-fluoro-phenyl)-5-methyl-isoxazol-4-ylmethyl]-amino}-pyridazine-3-carboxylic acid ethyl ester (89 mg, 0.25 mmol) was converted, using 4-aminotetrahydropyran instead of aminomethylcyclopropane, to the title compound (64 mg, 62%) which was obtained as a white foam. MS: m/e=412.5 [M+H]$^+$.

EXAMPLE 86

6-(5-Methyl-3-phenyl-isoxazol-4-ylmethoxy)-[1,2,4]triazolo[4,3-b]pyridazine

To a solution of (5-methyl-3-phenyl-isoxazol-4-yl)-methanol (100 mg, 0.53 mmol) in DMF (2 mL) was added sodium hydride (55% dispersion in mineral oil, 25.4 mg, 0.58 mmol). The mixture was stirred at room temperature for 15 min. After addition of 6-chloro-1,2,4-triazolo[4,3-b]pyridazine (90 mg, 0.58 mmol) the mixture was stirred at room temperature for another 2 h. Then the mixture was evaporated, extracted (ethyl acetate/water) and the organic phase was dried with sodium sulfate and concentrated. Chromatography (SiO$_2$, dichloromethane:methanol=100:0 to 9:1) afforded the title compound (80 mg, 51%) as a white solid. MS: m/e=308.4 [M+H]$^+$.

EXAMPLE 87

3-Methyl-6-(5-methyl-3-phenyl-isoxazol-4-ylmethoxy)-[1,2,4]triazolo[4,3-b]pyridazine As described for example 86, (5-methyl-3-phenyl-isoxazol-4-yl)-methanol (100 mg, 0.53 mmol) was converted, using 6-chloro-3-methyl-1,2,4-triazolo[4,3-b]pyridazine instead of 6-chloro-1,2,4-triazolo[4,3-b]pyridazine, to the title compound (70 mg, 41%) which was obtained as a white solid. MS: m/e=322.3 [M+H]$^+$.

EXAMPLE 88

6-(5-Methyl-3-phenyl-isoxazol-4-ylmethoxy)-[1,2,4]triazolo[4,3-b]pyridazine-3-carboxylic acid ethyl ester To a solution of (5-methyl-3-phenyl-isoxazol-4-yl)-methanol (60 mg, 0.32 mmol) in DMF (2 mL) was added sodium hydride (55% dispersion in mineral oil, 15 mg, 0.35 mmol). The mixture was stirred at room temperature overnight. After addition of a solution of 6-chloro-1,2,4-triazolo[4,3-b]pyridazine-3-carboxylic acid ethyl ester (79 mg, 0.35 mmol) in DMF (2 mL) the mixture was stirred at room temperature overnight. Then the mixture was evaporated, extracted (ethyl acetate/water) and the organic phase was dried with sodium sulfate and concentrated. Purification by preparative HPLC on reversed phase eluting with acetonitrile/water [0.1% aq NH$_3$ (25%)] afforded the title compound (20 mg, 14%) as a white solid. MS: m/e=380.0 [M+H]$^+$.

EXAMPLE 89

3-Furan-2-yl-6-(5-methyl-3-phenyl-isoxazol-4-ylmethoxy)-[1,2,4]triazolo[4,3-b]pyridazine To a solution of (5-methyl-3-phenyl-isoxazol-4-yl)-methanol (60 mg, 0.32 mmol) in DMF (2 mL) was added sodium hydride (55% dispersion in mineral oil, 15 mg, 0.35 mmol). The mixture was stirred at room temperature overnight. After addition of a solution of 6-chloro-3-(2-furanyl)-1,2,4-triazolo[4,3-b]pyridazine (77 mg, 0.35 mmol) in DMF (2 mL) the mixture was stirred at room temperature overnight. Then the mixture was evaporated, extracted (ethyl acetate/water) and the organic phase was dried with sodium sulfate and concentrated. Chromatography (SiO$_2$, heptane:ethyl acetate=100:0 to 1:1) afforded the title compound (105 mg, 67%) as a white foam. MS: m/e=374.5 [M+H]$^+$.

EXAMPLE 90

6-[3-(3-Fluoro-phenyl)-5-methyl-isoxazol-4-ylmethoxy]-[1,2,4]triazolo[4,3-b]pyridazine To a solution of [3-(3-fluoro-phenyl)-5-methyl-isoxazol-4-yl]-methanol (100 mg, 0.48 mmol) in DMF (2 mL) was added sodium hydride (55% dispersion in mineral oil, 23.2 mg, 0.53 mmol). The mixture was stirred at room temperature for 15 min. After addition of a solution of 6-chloro-1,2,4-triazolo[4,3-b]pyridazine (82 mg, 0.53 mmol) in DMF (3 mL) the mixture was stirred at room temperature overnight. Then the mixture was poured into water, extracted (ethyl acetate/water) and the organic phase was dried with sodium sulfate and concentrated. Chromatography (SiO$_2$, heptane:ethyl acetate=100:0 to 9:1) afforded the title compound (80 mg, 51%) as a white solid. MS: m/e=326.0 [M+H]$^+$.

EXAMPLE 91

6-[3-(4-Fluoro-phenyl)-5-methyl-isoxazol-4-ylmethoxy]-[1,2,4]triazolo[4,3-b]pyridazine As described for example 90, [3-(4-fluoro-phenyl)-5-methyl-isoxazol-4-yl]-methanol (100 mg, 0.53 mmol) was converted, instead of [3-(3-fluoro-phenyl)-5-methyl-isoxazol-4-yl]-methanol, to the title compound (99 mg, 63%) which was obtained as a white solid. MS: m/e=326.1 [M+H]$^-$.

EXAMPLE 92

3-Chloro-6-(5-methyl-3-pyridin-2-yl-isoxazol-4-ylmethoxy)-pyridazine a) Pyridine-2-carboxaldoxime As described for example 90, 2-pyridinecarboxaldehyde (53.6 g, 500 mmol) was converted, instead of 3-fluorobenzaldehyde, to the title compound (47.7 g, 78%) which was obtained as a white solid. MS: m/e=123.3 [M+H]$^-$.

b) 5-Methyl-3-pyridin-2-yl-isoxazole-4-carboxylic acid ethyl ester

As described for example 67a, pyridine-2-carboxaldoxime (42.6 g, 349 mmol) was converted, instead of pyridine-4-carboxaldoxime, to the title compound (58.9 g, 73%) which was obtained as a yellow oil. MS: m/e=233.3 [M+H]$^+$.

c) (5-Methyl-3-pyridin-2-yl-isoxazol-4-yl)-methanol

As described for example 67b, 5-methyl-3-pyridin-2-yl-isoxazole-4-carboxylic acid ethyl ester (25 g, 108 mmol) was converted, instead of 5-methyl-3-pyridin-4-yl-isoxazole-4- carboxylic acid ethyl ester, to the title compound (19.8 g, 97%) which was obtained as a light yellow solid. MS: m/e=191.3 [M+H]$^+$.

d) 3-Chloro-6-(5-methyl-3-pyridin-2-yl-isoxazol-4-ylmethoxy)-pyridazine

As described for example 48e, (5-methyl-3-pyridin-2-yl-isoxazol-4-yl)-methanol (5.0 g, 26 mmol) was converted, instead of [3-(3-fluoro-phenyl)-5-methyl-isoxazol-4-yl]-methanol, to the title compound (5.7 g, 72%) which was obtained as an off white solid. MS: m/e=303.3 [M+H]$^+$.

EXAMPLE 93

6-(5-Methyl-3-pyridin-2-yl-isoxazol-4-ylmethoxy)-pyridazine-3-carboxylic acid ethyl ester As described for example 49, 3-chloro-6-(5-methyl-3-pyridin-2-yl-isoxazol-4-ylmethoxy)-pyridazine (5.6 g, 18 mmol) was converted, instead of 3-chloro-6-[3-(3-fluoro-phenyl)-5-methyl-isoxazol-4-ylmethoxy]-pyridazine, to the title compound (5.3 g, 83%) which was obtained as an off white solid. MS: m/e=341.3 [M+H]$^-$.

EXAMPLE 94

6-(5-Methyl-3-pyridin-2-yl-isoxazol-4-ylmethoxy)-pyridazine-3-carboxylic acid (tetrahydro-pyran-4-yl)-amide A solution of trimethylaluminium (2 M in toluene, 600 µL, 1.2 mmol) was added dropwise (exothermic) to a solution of 4-aminotetrahydropyran (121 mg, 1.2 mmol) in dioxane (6 mL) and the resulting mixture was stirred at room temperature for 1 h. Then a solution of 6-(5-methyl-3-pyridin-2-yl-isoxazol-4-ylmethoxy)-pyridazine-3-carboxylic acid ethyl ester (102 mg, 0.3 mmol) in dioxane (3 mL) was added. The resulting mixture was heated at 85-95° C. for 5 h, cooled to room temperature, poured into a sodium potassium tartrate solution and extracted with ethyl acetate which was then washed with brine, dried over sodium sulfate and evaporated. Purification by chromatography (SiO$_2$, heptane:ethyl acetate=100:0 to 1:1) afforded the title compound (62 mg, 52%) which was obtained as a white solid after recrystallisation from ethylacetate:heptane. MS: m/e=396.3 [M+H]$^+$.

EXAMPLE 95

6-(5-Methyl-3-pyridin-2-yl-isoxazol-4-ylmethoxy)-pyridazine-3-carboxylic acid isopropylamide As described for example 94, (5-methyl-3-pyridin-2-yl-isoxazol-4-yl)-methanol (102 mg, 0.3 mmol) was converted, using isopropylamine instead of 4-aminotetrahydropyran, to the title compound (86 mg, 81%) which was obtained as a white solid. MS: m/e=354.4 [M+H]$^+$.

EXAMPLE 96

[6-(5-Methyl-3-pyridin-2-yl-isoxazol-4-ylmethoxy)-pyridazin-3-yl]-morpholin-4-yl-methanone As described for example 94, (5-methyl-3-pyridin-2-yl-isoxazol-4-yl)-methanol (102 mg, 0.3 mmol) was converted, using morpholine instead of 4-aminotetrahydropyran, to the title compound (85 mg, 74%) which was obtained as a white solid. MS: m/e=382.5 [M+H]$^+$.

EXAMPLE 97

6-(5-Methyl-3-pyridin-2-yl-isoxazol-4-ylmethoxy)-pyridazine-3-carboxylic acid cyclopropylamide As described for example 94, (5-methyl-3-pyridin-2-yl-isoxazol-4-yl)-methanol (102 mg, 0.3 mmol) was converted, using cyclopropylamine instead of 4-aminotetrahydropyran, to the title compound (74 mg, 70%) which was obtained as a white solid. MS: m/e=352.5 [M+H]$^+$.

EXAMPLE 98

6-(5-Methyl-3-pyridin-2-yl-isoxazol-4-ylmethoxy)-pyridazine-3-carboxylic acid (2,2,2-trifluoro-ethyl)-amide As described for example 94, (5-methyl-3-pyridin-2-yl-isoxazol-4-yl)-methanol (102 mg, 0.3 mmol) was converted, using 2,2,2-trifluoroethylamine instead of 4-aminotetrahydropyran, to the title compound (110 mg, 93%) which was obtained as a white solid. MS: m/e=394.3 [M+H]$^+$.

EXAMPLE 99

(1,1-Dioxo-1λ6-thiomorpholin-4-yl)-[6-(5-methyl-3-pyridin-2-yl-isoxazol-4-ylmethoxy)-pyridazin-3-yl]-methanone As described for example 94, (5-methyl-3-pyridin-2-yl-isoxazol-4-yl)-methanol (102 mg, 0.3 mmol) was converted, using thiomorpholin 1,1-dioxide instead of 4-aminotetrahydropyran, to the title compound (101 mg, 78%) which was obtained as a light yellow solid. MS: m/e=430.1 [M+H]$^-$.

EXAMPLE 100

6-(5-Methyl-3-pyridin-2-yl-isoxazol-4-ylmethoxy)-pyridazine-3-carboxylic acid cyclopropylmethyl-amide As described for example 94, (5-methyl-3-pyridin-2-yl-isoxazol-4-yl)-methanol (102 mg, 0.3 mmol) was converted, using aminomethylcyclopropane instead of 4-aminotetrahydropyran, to the title compound (85 mg, 78%) which was obtained as a white solid. MS: m/e=366.3 [M+H]$^+$.

EXAMPLE 101

6-(5-Methyl-3-pyridin-2-yl-isoxazol-4-ylmethoxy)-pyridazine-3-carboxylic acid (2-hydroxy-ethyl)-amide As described for example 94, (5-methyl-3-pyridin-2-yl-isoxazol-4-yl)-methanol (102 mg, 0.3 mmol) was converted, using aminoethanol instead of 4-aminotetrahydropyran, to the title compound (23 mg, 22%) which was obtained as a white solid. MS: m/e=356.3 [M+H]$^+$.

EXAMPLE 102

6-(5-Methyl-3-pyridin-2-yl-isoxazol-4-ylmethoxy)-pyridazine-3-carboxylic acid methylamide As described for example 94, (5-methyl-3-pyridin-2-yl-isoxazol-4-yl)-methanol (102 mg, 0.3 mmol) was converted, using methylamine (2 M solution in THF) instead of 4-aminotetrahydropyran, to the title compound (77 mg, 79%) which was obtained as a white solid. MS: m/e=326.5 [M+H]$^+$.

EXAMPLE 103

6-(5-Methyl-3-pyridin-2-yl-isoxazol-4-ylmethoxy)-pyridazine-3-carboxylic acid ethylamide As described for example 94, (5-methyl-3-pyridin-2-yl-isoxazol-4-yl)-methanol (102 mg, 0.3 mmol) was converted, using ethylamine (2 M solution in THF) instead of 4-aminotetrahydropyran, to the title compound (75 mg, 74%) which was obtained as a white solid. MS: m/e=340.4 [M+H]$^+$.

EXAMPLE 104

[6-(5-Methyl-3-pyridin-2-yl-isoxazol-4-ylmethoxy)-pyridazin-3-yl]-thiomorpholin-4-yl-methanone As described for example 94, (5-methyl-3-pyridin-2-yl-isoxazol-4-yl)-methanol (102 mg, 0.3 mmol) was converted, using thiomorpholine instead of 4-aminotetrahydropyran, to the title compound (97 mg, 81%) which was obtained as a light yellow solid. MS: m/e=398.1 [M+H]$^+$.

EXAMPLE 105

6-(5-Methyl-3-pyridin-2-yl-isoxazol-4-ylmethoxy)-pyridazine-3-carboxylic acid (2-hydroxy-1,1-dimethyl-ethyl)-amide As described for example 94, (5-methyl-3-pyridin-2-yl-isoxazol-4-yl)-methanol (102 mg, 0.3 mmol) was converted, using 2-amino-2-methyl-1-propanol instead of 4-aminotetrahydropyran, to the title compound (10 mg, 9%) which was obtained as a white solid. MS: m/e=384.1 [M+H]$^+$.

EXAMPLE 106

6-(5-Methyl-3-pyridin-2-yl-isoxazol-4-ylmethoxy)-pyridazine-3-carboxylic acid (2-methoxy-ethyl)-amide As described for example 94, (5-methyl-3-pyridin-2-yl-isoxazol-4-yl)-methanol (102 mg, 0.3 mmol) was converted, using 2-methoxyethylamine instead of 4-aminotetrahydropyran, to the title compound (50 mg, 45%) which was obtained as an off white solid. MS: m/e=370.2 [M+H]$^+$.

EXAMPLE 107

6-(5-Methyl-3-pyridin-4-yl-isoxazol-4-ylmethoxy)-pyridazine-3-carboxylic acid (2-hydroxy-ethyl)-amide As described for example 69, 6-(5-methyl-3-pyridin-4-yl-isoxazol-4-ylmethoxy)-pyridazine-3-carboxylic acid ethyl ester (100 mg, 0.29 mmol) was converted, using 2-aminoethanol instead of isopropylamine, to the title compound (24 mg, 23%) which was obtained as a light yellow solid. MS: m/e=356.3 [M+H]$^+$.

EXAMPLE 108

6-(5-Methyl-3-pyridin-4-yl-isoxazol-4-ylmethoxy)-pyridazine-3-carboxylic acid methylamide As described for example 69, 6-(5-methyl-3-pyridin-4-yl-isoxazol-4-ylmethoxy)-pyridazine-3-carboxylic acid ethyl ester (100 mg, 0.29 mmol) was converted, using methylamine (2 M solution in THF) instead of isopropylamine, to the title compound (16 mg, 17%) which was obtained as a white solid. MS: m/e=326.1 [M+H]$^-$.

EXAMPLE 109

6-(5-Methyl-3-pyridin-4-yl-isoxazol-4-ylmethoxy)-pyridazine-3-carboxylic acid ethylamide As described for example 69, 6-(5-methyl-3-pyridin-4-yl-isoxazol-4-ylmethoxy)-pyridazine-3-carboxylic acid ethyl ester (100 mg, 0.29 mmol) was converted, using ethylamine (2 M solution in THF) instead of isopropylamine, to the title compound (33 mg, 33%) which was obtained as a white solid. MS: m/e=340.1 [M+H]$^-$.

EXAMPLE 110

3-Chloro-6-[3-(5-fluoro-pyridin-2-yl)-5-methyl-isoxazol-4-ylmethoxy]-pyridazine a) 5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 [M+H]$^+$.

b) 3-(5-Fluoro-pyridin-2-yl)-5-methyl-isoxazole-4-carboxylic acid ethyl ester To a suspension of N-chlorosuccinimide (4.63 g, 35 mmol) in chloroform (21 mL) was added pyridine (0.28 mL, 3.5 mmol) and a solution of 5-fluoro-pyridine-2-carbaldehyde oxime (4.86 g, 35 mmol) in chloroform (110 mL) during 15 min at room temperature. After stirring for 30 min at this temperature a solution of ethyl (E)-3-(1-pyrrolidino)-2-butenoate (6.36 g, 35 mmol) in chloroform (4.4 mL) was added. The resulting suspension was warmed to 50° C. and a solution of triethylamine (4.83 mL, 35 mmol) in chloroform (4.4 mL) was added dropwise over a period of 30 min. Stirring was continued for 1.5 h at 50° C. and then cooled to ambient temperature. The solution was then diluted with ice-water (200 mL) and the aqueous layers were extracted with dichloromethane (50 mL) and dried over sodium sulfate and evaporation to give a dark brown oil. Purification by chromatography (SiO$_2$, heptane:ethyl acetate=100:0 to 20:80) afforded the title compound (5.83 g, 67%) as yellow oil. MS: m/e=251.1 [M+H]$^+$.

c) [3-(5-Fluoro-pyridin-2-yl)-5-methyl-isoxazol-4-yl]-methanol

To a solution of 3-(5-fluoro-pyridin-2-yl)-5-methyl-isoxazole-4-carboxylic acid ethyl ester (2.5 g, 10 mmol) in dry THF (34 mL), cooled to 0° C., was added lithiumaluminiumhydride (209 mg, 2.3 mmol) portionwise. After allowing to warm up to room temperature over 1 h, the mixture was cooled to 0° C. and water (0.2 mL) was added carefully followed by aqueous sodium hydroxide (15%, 0.2 mL) and water (0.6 mL). The resulting suspension was stirred for 4 h at ambient temperature and filtered over Hyflo®. The filtrate was then concentrated and purification by chromatography (SiO$_2$, heptane:ethyl acetate=50:50 to 0:100) afforded the title compound (1.47 g, 71%) as a light yellow solid. MS: m/e=209.1 [M+H]$^+$.

d) 3-Chloro-6-[3-(5-fluoro-pyridin-2-yl)-5-methyl-isoxazol-4-ylmethoxy]-pyridazine As described for example 92, [3-(5-fluoro-pyridin-2-yl)-5-methyl-isoxazol-4-yl]-methanol (803 mg, 3.9 mmol) was converted, instead of (5-methyl-3-pyridin-2-yl-isoxazol-4-yl)-methanol, to the title compound (521 g, 42%) which was obtained as an off white solid. MS: m/e=321.1 [M+H]$^+$.

EXAMPLE 111

6-[3-(5-Fluoro-pyridin-2-yl)-5-methyl-isoxazol-4-ylmethoxy]-pyridazine-3-carboxylic acid ethyl ester As described for example 93, 3-chloro-6-[3-(5-fluoro-pyridin-2-yl)-5-methyl-isoxazol-4-ylmethoxy]-pyridazine (489 mg, 1.5 mmol) was converted, instead of 3-chloro-6-(5-methyl-3-pyridin-2-yl-isoxazol-4-ylmethoxy)-pyridazine, to the title compound (436 mg, 80%) which was obtained as a white solid. MS: m/e=359.1 [M+H].

EXAMPLE 112

6-[3-(5-Fluoro-pyridin-2-yl)-5-methyl-isoxazol-4-ylmethoxy]-pyridazine-3-carboxylic acid (2-hydroxy-1,1-dimethyl-ethyl)-amide a) 6-[3-(5-Fluoro-pyridin-2-yl)-5-methyl-isoxazol-4-ylmethoxy]-pyridazine-3-carboxylic acid To a solution of 6-[3-(5-fluoro-pyridin-2-yl)-5-methyl-isoxazol-4-ylmethoxy]-pyridazine-3-carboxylic acid ethyl ester (379 mg, 1.1 mmol) in THF (2.6 mL), water (2.6 mL) and methanol (0.5 mL) was added lithium hydroxide monohydrate (88.8 mg, 2.1 mmol) and the resulting mixture stirred at room temperature overnight and then acidified with HCl (4 N) and extracted with ethyl acetate. The combined organic layers were then washed with water and brine, dried over sodium sulfate and evaporated to afford the title product (329 mg, 94%) which was obtained as white solid. MS: m/e=329.1 [M−H]$^-$.

b) 6-[3-(5-Fluoro-pyridin-2-yl)-5-methyl-isoxazol-4-ylmethoxy]-pyridazine-3-carboxylic acid (2-hydroxy-1,1-dimethyl-ethyl)-amide To a solution of 6-[3-(5-fluoro-pyridin-2-yl)-5-methyl-isoxazol-4-ylmethoxy]-pyridazine-3-carboxylic acid (69.4 mg, 0.21 mmol) in DMF (1.1 mL) were added 2-(1H-benzotriazole-1-yl)-1,1,3,3-tetramethyluronium tetrafluoroborate (74.1 mg, 0.23 mmol), N,N-diisopropyl ethyl amine (179 µL, 1.05 mmol) and 2-amino-2-methyl-1-propanol (20.6 mg, 0.23 mmol). The resulting reaction mixture was stirred for 30 min at room temperature and diluted with water. The mixture was then extracted with ethyl acetate and the combined organic layers washed with aqueous sodium carbonate (saturated) and dried over sodium sulfate. Concentration and purification by chromatography (SiO$_2$, heptane:ethyl acetate=1:0 to 3:7) afforded the title compound (74 mg, 88%) which was obtained as an off white solid. MS: m/e=402.4 [M+H]$^+$.

EXAMPLE 113

6-[3-(5-Chloro-pyridin-2-yl)-5-methyl-isoxazol-4-ylmethoxy]-pyridazine-3-carboxylic acid a) 5-Chloro-pyridine-2-carbaldehyde

To a solution of 2-bromo-5-chloropyridine (14.8 g, 77 mmol) in THF (38.5 mL) was added dropwise a a solution of i-PrMgCl.LiCl (14% in THF, 81 mL, 85 mmol) at 0-5° C. and the resulting mixture stirred at 0° C. for 1 h. Then DMF (7.7 mL, 100 mmol) was added dropwise at −5° C. and the temperature maintained at 0° C. for 2 h. The reaction mixture was then poured into ice cold saturated brine (500 mL) and then extracted with ethylacetate (2×300 mL). The combined organic layers were washed with saturated sodiumhydrogencarbonate solution, brine, dried over sodium sulfate, filtered and evaporated. Purification by chromatography (SiO$_2$, heptane:ethyl acetate=1:0 to 9:1) afforded the title compound (6.24 g, 57%) which was obtained as a brown solid. MS: m/e=141.0 [M]$^+$.

b) 5-Chloro-pyridine-2-carbaldehyde oxime

As described for example 110a, 5-chloro-pyridine-2-carbaldehyde (6.9 g, 4.8 mmol) was converted, instead of 5-fluoro-2-formylpyridine, to the title compound (6.7 g, 89%) which was obtained as a light brown solid. MS: m/e=157.1 [M+H]$^+$.

c) 3-(5-Chloro-pyridin-2-yl)-5-methyl-isoxazole-4-carboxylic acid ethyl ester As described for example 110b, 5-chloro-pyridine-2-carbaldehyde oxime (5.6 g, 36 mmol) was converted, instead of 5-fluoro-pyridine-2-carbaldehyde oxime, to the title compound (7.7 g, 80%) which was obtained as a yellow oil. MS: m/e=267.0 [M+H]$^+$.

d) [3-(5-Chloro-pyridin-2-yl)-5-methyl-isoxazol-4-yl]-methanol

As described for example 110c, 3-(5-chloro-pyridin-2-yl)-5-methyl-isoxazole-4-carboxylic acid ethyl ester (1.26 g, 4.7 mmol) was converted, instead of 3-(5-fluoro-pyridin-2-yl)-5-methyl-isoxazole-4-carboxylic acid ethyl ester, to the title compound (773 mg, 73%) which was obtained as an off white solid. MS: m/e=224.9 [M+H]$^-$.

e) 3-Chloro-6-[3-(5-chloro-pyridin-2-yl)-5-methyl-isoxazol-4-ylmethoxy]-pyridazine As described for example 110d, [3-(5-chloro-pyridin-2-yl)-5-methyl-isoxazol-4-yl]-methanol (2.0 g, 8.9 mmol) was converted, instead of [3-(5-fluoro-pyridin-2-yl)-5-methyl-isoxazol-4-yl]-methanol, to the title compound (2.47 g, 83%) which was obtained as a light brown solid. MS: m/e=337.0 [M+H]$^+$.

f) 6-[3-(5-Chloro-pyridin-2-yl)-5-methyl-isoxazol-4-ylmethoxy]-pyridazine-3-carboxylic acid ethyl ester As described for example 111, 3-chloro-6-[3-(5-chloro-pyridin-2-yl)-5-methyl-isoxazol-4-ylmethoxy]-pyridazine (2.36 g, 7.0 mmol) was converted, instead of 3-chloro-6-[3-(5-fluoro-pyridin-2-yl)-5-methyl-isoxazol-4-ylmethoxy]-pyridazine, to the title compound (1.89 g, 72%) which was obtained as a white solid. MS: m/e=375.3 [M+H]$^+$.

g) 6-[3-(5-Chloro-pyridin-2-yl)-5-methyl-isoxazol-4-ylmethoxy]-pyridazine-3-carboxylic acid As described for example 112a, 6-[3-(5-chloro-pyridin-2-yl)-5-methyl-isoxazol-4-ylmethoxy]-pyridazine-3-carboxylic acid ethyl ester (1.82 g, 4.9 mmol) was converted, instead of 5-[3-(4-chloro-phenyl)-isoxazol-4-ylmethoxy]-pyrazine-2-carboxylic acid methyl ester, to the title compound (1.57 g, 93%) which was obtained as a white solid. MS: m/e=345.3 [M−H]$^−$.

EXAMPLE 114

6-(5-Methyl-3-pyrimidin-4-yl-isoxazol-4-ylmethoxy)-pyridazine-3-carboxylic acid (2-hydroxy-ethyl)-amide a) (E)-4-Dimethylamino-1,1-dimethoxy-but-3-en-2-one

A mixture of N,N-dimethylformamide dimethylacetal (86.0 g, 584 mmol) and methylglyoxal 1,1-dimethylacetal (85.6 g, 724 mmol) in isobutanol (500 mL) was heated at 100° C. overnight. The mixture was then cooled and evaporated. Purification by distillation afforded the title product (49.9 g, 48%) as an orange liquid. Bp 123-124° C. at 0.9 mbar. MS: m/e=174.4 [M+H]$^+$.

b) 4-Dimethoxymethyl-pyrimidine

A mixture of (E)-4-dimethylamino-1,1-dimethoxy-but-3-en-2-one (49.6 g, 286 mmol) and formamidine acetate (44.7 g, 429 mmol) was heated at 120° C. for 4 h. After cooling to room temperature the mixture was poured into water and extracted with dichloromethane. The combined organic extracts were then dried over sodium sulfate, filtered and evaporated. Purification by distillation afforded the title product (31 g, 70%) as a colourless liquid. Bp 59-60° C. at 1.3 mbar. MS: m/e=155.0 [M+H]$^+$.

c) Pyrimidine-4-carbaldehyde

A solution of 4-dimethoxymethyl-pyrimidine (30.6 g, 199 mmol) in water (235 mL) and concentrated sulfuric acid (2.9 g, 30 mmol) was heated at 60° C. for 24 h. After cooling to room temperature the pH was set to 8 with saturated aqueous sodium hydrogen carbonate solution. The mixture was then extracted overnight in a continuous extraction (Keberle) for 48 h with chloroform. The chloroform extract was then dried over sodium sulfate, filtered and evaporated. Purification by chromatography (SiO$_2$, dichloromethane:methanol=1:0 to 95:5) afforded the title compound (8.1 g, 26%) which was obtained as a brown oil. MS: m/e=108.0 [M]$^+$.

d) Pyrimidine-4-carbaldehyde oxime

As described for example 110a, pyrimidine-4-carbaldehyde (8.1 g, 51 mmol) was converted, instead of 5-fluoro-2-formylpyridine, to the title compound (2.2 g, 35%) which was obtained as a light brown solid. MS: m/e=124.0 [M+H]$^+$.

e) 5-Methyl-3-pyrimidin-4-yl-isoxazole-4-carboxylic acid ethyl ester

As described for example 110b, pyrimidine-4-carbaldehyde oxime (2.2 g, 18 mmol) was converted, instead of 5-fluoro-pyridine-2-carbaldehyde oxime, to the title compound (2.6 g, 63%) which was obtained as a light brown oil. MS: m/e=233.9 [M+H]$^+$.

f) 5-Methyl-3-pyrimidin-4-yl-isoxazole-4-carboxylic acid

As described for example 112a, 5-methyl-3-pyrimidin-4-yl-isoxazole-4-carboxylic acid ethyl ester (500 mg, 2.1 mmol) was converted, instead of 5-[3-(4-chloro-phenyl)-isoxazol-4-ylmethoxy]-pyrazine-2-carboxylic acid methyl ester, to the title compound (321 mg, 73%) which was obtained as an off white solid. MS: m/e=204.1 [M−H]$^−$.

g) (5-Methyl-3-pyrimidin-4-yl-isoxazol-4-yl)-methanol

To a solution of 5-methyl-3-pyrimidin-4-yl-isoxazole-4-carboxylic acid (300 mg, 1.46 mmol) in THF (4 mL) at −10° C. was added triethylamine (203 µL, 1.46 mmol) and then a solution of ethylchloroformate (139 µL, 1.46 mmol) in THF (1 mL) added keeping the temperature below −5° C. After 1 h the mixture was filtered and the filtrate cooled to −10° C. and a suspension of sodiumborohydride (138 mg, 3.66 mmol) in water (1.5 mL) added over 15 minutes keeping the temperature below −5° C. The mixture was then allowed to warm up to room temperature over 2 h and diluted with aqueous sodium hydroxide (1 N) and extracted with ethylacetate. The combined organic layers were then washed with water and brine, dried over sodium sulfate and evaporated. Purification by chromatography (SiO$_2$, dichloromethane:methanol=9:1) afforded the title product (52.5 mg, 19%) which was obtained as white solid. MS: m/e=190.0 [M−H]$^−$.

h) 3-Chloro-6-(5-methyl-3-pyrimidin-4-yl-isoxazol-4-ylmethoxy)-pyridazine

As described for example 110d, (5-methyl-3-pyrimidin-4-yl-isoxazol-4-yl)-methanol (400 mg, 2.1 mmol) was converted, instead of [3-(5-fluoro-pyridin-2-yl)-5-methyl-isoxazol-4-yl]-methanol, to the title compound (497 mg, 78%) which was obtained as a white solid. MS: m/e=304.0 [M+H]$^+$.

i) 6-(5-Methyl-3-pyrimidin-4-yl-isoxazol-4-ylmethoxy)-pyridazine-3-carboxylic acid ethyl ester As described for example 111, 3-chloro-6-(5-methyl-3-pyrimidin-4-yl-isoxazol-4-ylmethoxy)-pyridazine (654 mg, 2.2 mmol) was converted, instead of 3-chloro-6-[3-(5-fluoro-pyridin-2-yl)-5-methyl-isoxazol-4-ylmethoxy]-pyridazine, j) 6-(5-Methyl-3-pyrimidin-4-yl-isoxazol-4-yl-methoxy)-pyridazine-3-carboxylic acid As described for example 112a, 6-(5-methyl-3-pyrimidin-4-yl-isoxazol-4-ylmethoxy)-pyridazine-3-carboxylic acid ethyl ester (616 mg, 1.8 mmol) was converted, instead of 5-[3-(4-chloro-phenyl)-isoxazol-4-ylmethoxy]-pyrazine-2-carboxylic acid methyl ester, to the title compound (520 mg, 92%) which was obtained as a white solid. MS: m/e=312.3 [M−H]⁻.

k) 6-(5-Methyl-3-pyrimidin-4-yl-isoxazol-4-yl-methoxy)-pyridazine-3-carboxylic acid (2-hydroxy-ethyl)-amide As described for example 112b, 6-(5-methyl-3-pyrimidin-4-yl-isoxazol-4-ylmethoxy)-pyridazine-3-carboxylic acid (38 mg, 0.12 mmol) was converted, instead of 6-[3-(5-fluoro-pyridin-2-yl)-5-methyl-isoxazol-4-ylmethoxy]-pyridazine-3-carboxylic acid, using ethanolamine instead of 2-amino-2-methyl-1-propanol, to the title compound (18 mg, 42%) which was obtained as a light yellow foam. MS: m/e=357.1 [M+H]⁺.

EXAMPLE 115

6-(5-Methyl-3-pyrimidin-4-yl-isoxazol-4-yl-methoxy)-pyridazine-3-carboxylic acid (2-hydroxy-1,1-dimethyl-ethyl)-amide As described for example 114k, 6-(5-methyl-3-pyrimidin-4-yl-isoxazol-4-ylmethoxy)-pyridazine-3-carboxylic acid (38 mg, 0.12 mmol) was converted, using 2-amino-2-methyl-1-propanol instead of ethanolamine, to the title compound (36 mg, 77%) which was obtained as an off white foam. MS: m/e=385.5 [M+H]⁺.

EXAMPLE 116

6-{[3-(3-Fluoro-phenyl)-5-methyl-isoxazol-4-ylmethyl]-amino}-pyridazine-3-carboxylic acid cyclopropylamide a) 2-[3-(3-Fluoro-phenyl)-5-methyl-isoxazol-4-ylmethyl]-isoindole-1,3-dione As described for example 78a, [3-(3-fluoro-phenyl)-5-methyl-isoxazol-4-yl]-methanol (5.83 g, 28 mmol) was converted, instead of [3-(4-fluoro-phenyl)-5-methyl-isoxazol-4-yl]-methanol, to the title compound (6.26 g, 66%) which was obtained as a white solid. MS: m/e=337.1 [M+H].

b) C-[3-(3-Fluoro-phenyl)-5-methyl-isoxazol-4-yl]-methylamine

As described for example 78b, 2-[3-(3-fluoro-phenyl)-5-methyl-isoxazol-4-ylmethyl]-isoindole-1,3-dione (6.26 g, 19 mmol) was converted, instead of 2-[3-(4-fluoro-phenyl)-5-methyl-isoxazol-4-ylmethyl]-isoindole-1,3-dione, to the title compound (2.95 g, 77%) which was obtained as a yellow oil. MS: m/e=207.3 [M+H]⁺.

c) (6-Chloro-pyridazin-3-yl)-[3-(3-fluoro-phenyl)-5-methyl-isoxazol-4-ylmethyl]-amine As described for example 78c, C-[3-(3-fluoro-phenyl)-5-methyl-isoxazol-4-yl]-methylamine (1.4 g, 6.8 mmol) was converted, instead of C-[3-(4-fluoro-phenyl)-5-methyl-isoxazol-4-yl]-methylamine, to the title compound (1.1 g, 51%) which was obtained as a light yellow solid. MS: m/e=319.1 [M+H]⁺.

d) 6-{[3-(3-Fluoro-phenyl)-5-methyl-isoxazol-4-ylmethyl]-amino}-pyridazine-3-carboxylic acid ethyl ester As described for example 49, (6-chloro-pyridazin-3-yl)-[3-(3-fluoro-phenyl)-5-methyl-isoxazol-4-ylmethyl]-amine (980 mg, 3.1 mmol) was converted, instead of 3-chloro-6-[3-(3-fluoro-phenyl)-5-methyl-isoxazol-4-ylmethoxy]-pyridazine, to the title compound (898 mg, 82%) which was obtained as a light red solid. MS: m/e=357.3 [M+H]⁺.

e) 6-{[3-(3-Fluoro-phenyl)-5-methyl-isoxazol-4-ylmethyl]-amino}-pyridazine-3-carboxylic acid cyclopropylamide As described for example 67e, 6-{[3-(3-fluoro-phenyl)-5-methyl-isoxazol-4-ylmethyl]-amino}-pyridazine-3-carboxylic acid ethyl ester (106 mg, 0.3 mmol) was converted, instead of 6-[(5-methyl-3-phenyl-isoxazol-4-ylmethyl)-amino]-pyridazine-3-carboxylic acid methyl ester, using cyclopropylamine instead of aminomethylcyclopropane, to the title compound (83 mg, 75%) which was obtained as a white solid. MS: m/e=368.1 [M+H]⁺.

EXAMPLE 117

6-{[3-(3-Fluoro-phenyl)-5-methyl-isoxazol-4-ylmethyl]-amino}-pyridazine-3-carboxylic acid cyclopropylmethyl-amide As described for example 116e, 6-{[3-(3-fluoro-phenyl)-5-methyl-isoxazol-4-ylmethyl]-amino}-pyridazine-3-carboxylic acid ethyl ester (107 mg, 0.3 mmol) was converted, using aminomethylcyclopropane instead of cyclopropylamine, to the title compound (72 mg, 63%) which was obtained as a white solid. MS: m/e=382.5 [M+H]⁺.

EXAMPLE 118

6-{[3-(3-Fluoro-phenyl)-5-methyl-isoxazol-4-ylmethyl]-amino}-pyridazine-3-carboxylic acid (2,2,2-trifluoro-ethyl)-amide As described for example 116e, 6-{[3-(3-fluoro-phenyl)-5-methyl-isoxazol-4-ylmethyl]-amino}-pyridazine-3-carboxylic acid ethyl ester (107 mg, 0.3 mmol) was converted, using 2,2,2-trifluoroethylamine instead of cyclopropylamine, to the title compound (72 mg, 59%) which was obtained as a white solid. MS: m/e=410.1 [M+H]⁻.

EXAMPLE 119

6-{[3-(5-Chloro-pyridin-2-yl)-5-methyl-isoxazol-4-ylmethyl]-amino}-pyridazine-3-carboxylic acid (2-hydroxy-1,1-dimethyl-ethyl)-amide a) 2-[3-(5-Chloro-pyridin-2-yl)-5-methyl-isoxazol-4-ylmethyl]-isoindole-1,3-dione As described for example 78a, [3-(5-chloro-pyridin-2-yl)-5-methyl-isoxazol-4-yl]-methanol (1.0 g, 4.45 mmol) was converted, instead of [3-(4-fluoro-phenyl)-5-methyl-isoxazol-4-yl]-methanol, to the title compound (1.35 g, 86%) which was obtained as a white solid. MS: m/e=354.1 [M+H]$^+$.

b) [3-(5-Chloro-pyridin-2-yl)-5-methyl-isoxazol-4-yl]-methylamine

As described for example 78b, 2-[3-(5-chloro-pyridin-2-yl)-5-methyl-isoxazol-4-ylmethyl]-isoindole-1,3-dione (1.3 g, 3.68 mmol) was converted, instead of 2-[3-(4-fluoro-phenyl)-5-methyl-isoxazol-4-ylmethyl]-isoindole-1,3-dione, to the title compound (570 mg, 69%) which was obtained as a white solid. MS: m/e=224.3 [M+H]$^+$.

c) (6-Chloro-pyridazin-3-yl)-[3-(5-chloro-pyridin-2-yl)-5-methyl-isoxazol-4-ylmethyl]-amine As described for example 78c, [3-(5-chloro-pyridin-2-yl)-5-methyl-isoxazol-4-yl]-methylamine (1.0 g, 4.47 mmol) was converted, instead of C-[3-(4-fluoro-phenyl)-5-methyl-isoxazol-4-yl]-methylamine, to the title compound (1.0 g, 69%) which was obtained as a light yellow solid. MS: m/e=336.3 [M+H]$^+$.

d) 6-{[3-(5-Chloro-pyridin-2-yl)-5-methyl-isoxazol-4-ylmethyl]-amino}-pyridazine-3-carboxylic acid ethyl ester As described for example 49, (6-chloro-pyridazin-3-yl)-[3-(5-chloro-pyridin-2-yl)-5-methyl-isoxazol-4-ylmethyl]-amine (930 mg, 2.76 mmol) was converted, instead of 3-chloro-6-[3-(3-fluoro-phenyl)-5-methyl-isoxazol-4-ylmethoxy]-pyridazine, to the title compound (443 mg, 43%) which was obtained as a light yellow solid. MS: m/e=374.3 [M+H]$^+$.

e) 6-{[3-(5-Chloro-pyridin-2-yl)-5-methyl-isoxazol-4-ylmethyl]-amino}-pyridazine-3-carboxylic acid As described for example 112a, 6-{[3-(5-chloro-pyridin-2-yl)-5-methyl-isoxazol-4-ylmethyl]-amino}-pyridazine-3-carboxylic acid ethyl ester (405 mg, 1.1 mmol) was converted, instead of 5-[3-(4-chloro-phenyl)-isoxazol-4-ylmethoxy]-pyrazine-2-carboxylic acid methyl ester, to the title compound (346 mg, 92%) which was obtained as an off white solid. MS: m/e=343.9 [M−H]$^-$.

f) 6-{[3-(5-Chloro-pyridin-2-yl)-5-methyl-isoxazol-4-ylmethyl]-amino}-pyridazine-3-carboxylic acid (2-hydroxy-1,1-dimethyl-ethyl)-amide As described for example 112b, 6-{[3-(5-chloro-pyridin-2-yl)-5-methyl-isoxazol-4-ylmethyl]-amino}-pyridazine-3-carboxylic acid (86 mg, 0.25 mmol) was converted, instead of 6-[3-(5-fluoro-pyridin-2-yl)-5-methyl-isoxazol-4-ylmethoxy]-pyridazine-3-carboxylic acid, to the title compound (72 mg, 69%) which was obtained as a white solid. MS: m/e=417.5 [M+H]$^+$.

EXAMPLE 120

6-[3-(4-Fluoro-phenyl)-isoxazol-4-ylmethoxy]-pyridazine-3-carboxylic acid ethyl ester a) (E)- and/or (Z)-4-Fluoro-benzaldehyde oxime

As described for example 110a, 4-fluorobenzaldehyde (24.8 g, 200 mmol) was converted, instead of 5-fluoro-2-formylpyridine, to the title compound (23.3 g, 84%) which was obtained as a white solid. MS: m/e=139.1 [M]$^+$.

b) (E)- and/or (Z)-N-Hydroxy-4-fluoro-benzenecarboximidoyl chloride

To a solution of (E)- and/or (Z)-4-fluoro-benzaldehyde oxime (100 g, 719 mmol) in DMF (500 mL) was added N-chlorosuccinimide (110 g, 791 mmol) portionwise keeping the temperature below 70° C. The reaction mixture was stirred at room temperature for 2.5 h and then extracted with tert-butyl methyl ether to afford the title compound (125 g, 100%) which was obtained as a yellow oil. MS: m/e=173.1 [M]$^+$.

c) 3-(4-Fluoro-phenyl)-isoxazole-4-carboxylic acid ethyl ester

To a solution of (E)- and/or (Z)-N-hydroxy-4-fluoro-benzenecarboximidoyl chloride (50 g, 241 mmol) in diethylether (1 L) was added a solution of ethyl 3-(N,N-dimethylamino)acrylate (87 mL, 601 mmol) and triethylamine (49 mL, 349 mmol) in diethylether (1 L). The resulting mixture was then stirred for 14 h at room temperature and evaporated. Purification by chromatography (SiO$_2$, heptane:ethyl acetate=100:0 to 4:1) afforded the title product (50.2 g, 88%) which was obtained as a light yellow solid. MS: m/e=236.1 [M+H]$^+$.

d) 3-(4-Fluoro-phenyl)-isoxazole-4-carboxylic acid

To a solution of 3-(4-fluoro-phenyl)-isoxazole-4-carboxylic acid ethyl ester (49 g, 208 mmol) in ethanol (215 mL) was added aqueous sodium hydroxide (2 N, 161 mL, 323 mmol) and the resulting mixture stirred overnight at room temperature. The mixture was then acidified with HCl solution (4 N, 85 mL) to pH 2-3. The precipitate was then filtered off and dissolved in THF (700 mL) and then washed with saturated sodium chloride solution. The aqueous phase was then extracted with ethyl acetate and THF (1:1, 300 mL) and the combined organic phases dried over sodium sulfate and evaporated to afford the title compound (40.8 g, 94%) which was obtained as an orange solid. MS: m/e=206.1 [M−H]$^-$.

e) [3-(4-Fluoro-phenyl)-isoxazol-4-yl]-methanol

To a solution of 3-(4-fluoro-phenyl)-isoxazole-4-carboxylic acid (40 g, 193 mmol) in THF (400 mL) at −10° C. was added triethylamine (27.1 mL, 193 mmol) and then a solution of ethylchloroformate (18.8 mL, 193 mmol) in THF (120 mL) added keeping the temperature below −5° C. After 1 h the mixture was filtered and the filtrate cooled to −10° C. and a suspension of sodiumborohydride (19 g, 483 mmol) in water (120 mL) added over 15 minutes keeping the temperature below −5° C. The mixture was then allowed to warm up to room temperature over 2 h and diluted with aqueous sodium hydroxide (1 N, 700 mL) and extracted with tert-butylmethylether. The combined organic layers were then washed with water and brine, dried over sodium sulfate and evaporated. Purification by chromatography (SiO$_2$, heptane:ethyl acetate=1:1) afforded the title product (20.1 g, 54%) which was obtained as a white solid. MS: m/e=194.1 [M+H]$^+$.

f) 3-Chloro-6-[3-(4-fluoro-phenyl)-isoxazol-4-ylmethoxy]-pyridazine

As described for example 48e, [3-(4-fluoro-phenyl)-isoxazol-4-yl]-methanol (2.0 g, 10.35 mmol) was converted, g) 6-[3-(4-Fluoro-phenyl)-isoxazol-4-ylmethoxy]-pyridazine-3-carboxylic acid ethyl ester As described for example 49, 3-chloro-6-[3-(4-fluoro-phenyl)-isoxazol-4-ylmethoxy]-pyridazine (2.3 g, 7.52 mmol) was converted, instead of 3-chloro-6-[3-(3-fluoro-phenyl)-5-methyl-isoxazol-4-ylmethoxy]-pyridazine, to the title compound (1.1 g, 42%) which was obtained as a white solid. MS: m/e=344.2 [M+H]$^+$.

EXAMPLE 121

6-[3-(4-Fluoro-phenyl)-isoxazol-4-ylmethoxy]-pyridazine-3-carboxylic acid isopropylamide As described for example 67e, 6-[3-(4-fluoro-phenyl)-isoxazol-4-ylmethoxy]-pyridazine-3-carboxylic acid ethyl ester (200 mg, 0.58 mmol) was converted, instead of 6-[(5-methyl-3-phenyl-isoxazol-4-ylmethyl)-amino]-pyridazine-3-carboxylic acid methyl ester, using isopropylamine instead of aminomethylcyclopropane, to the title compound (170 mg, 82%) which was obtained as a white solid. MS: m/e=357.2 [M+H]$^+$.

EXAMPLE 122

6-[3-(4-Fluoro-phenyl)-isoxazol-4-ylmethoxy]-pyridazine-3-carboxylic acid (tetrahydro-pyran-4-yl)-amide As described for example 121, 6-[3-(4-fluoro-phenyl)-isoxazol-4-ylmethoxy]-pyridazine-3-carboxylic acid ethyl ester (200 mg, 0.58 mmol) was converted, using 4-aminotetrahydropyran instead of isopropylamine, to the title compound (190 mg, 82%) which was obtained as a white solid. MS: m/e=399.1 [M+H]$^+$.

EXAMPLE 123

6-(3-Pyridin-2-yl-isoxazol-4-ylmethoxy)-pyridazine-3-carboxylic acid isopropylamide a) 3-Pyridin-2-yl-isoxazole-4-carboxylic acid ethyl ester

To a solution of N-chlorosuccinimide (54.7 g, 409 mmol) in DMF (1 L) was added pyridine-2-carbaldoxime (50 g, 409 mmol) portionwise and the resulting mixture was then stirred for 64 h at room temperature. To this solution was then added ethyl 3-(N,N-dimethylamino)acrylate (58.6 g, 409 mmol) and triethylamine (82.9 mL, 819 mmol) in chloroform (10 mL) and the resulting mixture was then stirred for 14 h at room temperature and poured onto a mixture of ice water and HCl (4 N, 100 mL) and extracted with ethylacetate. The organic extract was then washed with water, saturated aqueous sodium hydrogen carbonate solution, brine, dried with sodium sulfate, filtered and evaporated. Purification by distillation afforded the title product (58.9 g, 66%) which was obtained as a light brown liquid. Bp 125-127° C. at 0.4 mbar. MS: m/e=219.2 [M+H]$^+$.

b) 3-Pyridin-2-yl-isoxazole-4-carboxylic acid

As described for example 112a, 3-pyridin-2-yl-isoxazole-4-carboxylic acid ethyl ester (9.6 g, 44 mmol), instead of 6-[3-(5-fluoro-pyridin-2-yl)-5-methyl-isoxazol-4-ylmethoxy]-pyridazine-3-carboxylic acid ethyl ester, was converted to the title compound (6.5 g, 79%) which was obtained as an off-white solid. MS: m/e=189.3 [M–H]$^-$.

c) (3-Pyridin-2-yl-isoxazol-4-yl)-methanol

As described for example 114g, 3-pyridin-2-yl-isoxazole-4-carboxylic acid (39.0 g, 200 mmol) was converted, instead of 5-methyl-3-pyrimidin-4-yl-isoxazole-4-carboxylic acid, to the title compound (26.8 g, 76%) which was obtained as a white solid. MS: m/e=177.2 [M]$^-$.

d) 3-Chloro-6-(3-pyridin-2-yl-isoxazol-4-ylmethoxy)-pyridazine

As described for example 48e, (3-pyridin-2-yl-isoxazol-4-yl)-methanol (1.0 g, 5.68 mmol) was converted, instead of [3-(3-fluoro-phenyl)-5-methyl-isoxazol-4-yl]-methanol, to the title compound (1.16 g, 71%) which was obtained as a white solid. MS: m/e=289.0 [M+H]$^+$.

e) 6-(3-Pyridin-2-yl-isoxazol-4-ylmethoxy)-pyridazine-3-carboxylic acid ethyl ester As described for example 49, 3-chloro-6-(3-pyridin-2-yl-isoxazol-4-ylmethoxy)-pyridazine (1.1 g, 3.81 mmol) was converted, instead of 3-chloro-6-[3-(3-fluoro-phenyl)-5-methyl-isoxazol-4-ylmethoxy]-pyridazine, to the title compound (736 mg, 59%) which was obtained as an orange solid. MS: m/e=327.3 [M+H]$^-$.

f) 6-(3-Pyridin-2-yl-isoxazol-4-ylmethoxy)-pyridazine-3-carboxylic acid

As described for example 112a, 6-(3-pyridin-2-yl-isoxazol-4-ylmethoxy)-pyridazine-3-carboxylic acid ethyl ester (693 mg, 2.12 mmol) was converted, instead of 5-[3-(4-chloro-phenyl)-isoxazol-4-ylmethoxy]-pyrazine-2-carboxylic acid methyl ester, to the title compound (544 mg, 86%) which was obtained as a grey solid. MS: m/e=297.5 [M–H]$^-$.

g) 6-(3-Pyridin-2-yl-isoxazol-4-ylmethoxy)-pyridazine-3-carboxylic acid isopropylamide As described for example 112b, 6-(3-pyridin-2-yl-isoxazol-4-ylmethoxy)-pyridazine-3-carboxylic acid (70 mg, 0.24 mmol) was converted, instead of 6-[3-(5-fluoro-pyridin-2-yl)-5-methyl-isoxazol-4-ylmethoxy]-pyridazine-3-carboxylic acid, using isopropylamine instead of 2-amino-2-methyl-1-propanol, to the title compound (64 mg, 80%) which was obtained as a white solid. MS: m/e=340.3 [M+H]$^+$.

EXAMPLE 124

6-(3-Pyridin-2-yl-isoxazol-4-ylmethoxy)-pyridazine-3-carboxylic acid cyclopropylamide As described for example 123 g, 6-(3-pyridin-2-yl-isoxazol-4-ylmethoxy)-pyridazine-3-carboxylic acid (70 mg, 0.24 mmol) was converted, using cyclopropylamine instead of isopropylamine, to the title compound (52 mg, 66%) which was obtained as a white solid. MS: m/e=338.4 [M+H]+.

EXAMPLE 125

6-(3-Pyridin-2-yl-isoxazol-4-ylmethoxy)-pyridazine-3-carboxylic acid cyclopropylmethyl-amide As described for example 123 g, 6-(3-pyridin-2-yl-isoxazol-4-ylmethoxy)-pyridazine-3-carboxylic acid (70 mg, 0.24 mmol) was converted, using aminomethylcyclopropane instead of isopropylamine, to the title compound (50 mg, 61%) which was obtained as an off white solid. MS: m/e=352.3 [M+H]+.

EXAMPLE 126

6-(3-Pyridin-2-yl-isoxazol-4-ylmethoxy)-pyridazine-3-carboxylic acid (2,2,2-trifluoro-ethyl)-amide As described for example 123g, 6-(3-pyridin-2-yl-isoxazol-4-ylmethoxy)-pyridazine-3-carboxylic acid (70 mg, 0.24 mmol) was converted, using aminomethylcyclopropane instead of isopropylamine, to the title compound (77 mg, 87%) which was obtained as an off white solid. MS: m/e=380.0 [M+H]+.

EXAMPLE 127

6-[3-(5-Fluoro-pyridin-2-yl)-isoxazol-4-ylmethoxy]-pyridazine-3-carboxylic acid (2-hydroxy-1,1-dimethyl-ethyl)-amide a) 3-(5-Fluoro-pyridin-2-yl)-isoxazole-4-carboxylic acid ethyl ester To a solution of N-chlorosuccinimide (17.34 g, 130 mmol) in DMF (128 mL) was added 5-fluoro-pyridine-2-carbaldehyde oxime (18.2 g, 130 mmol) portionwise over 2 h at room temperature and as the reaction warmed up to 60° C. the mixture was cooled back to room temperature with an ice-water bath and the resulting mixture was then stirred for 64 h at room temperature. To this solution was then added ethyl 3-(N,N-dimethylamino)acrylate (18.6 g, 130 mmol) and tri-ethylamine (36.2 mL, 260 mmol) in chloroform (64 mL) and the resulting mixture was then stirred for 1 h at room temperature and poured onto a mixture of ice water and HCl (4 N, 1 L) and extracted with ethylacetate. The organic extract was then washed with water, saturated aqueous sodium hydrogen carbonate solution, brine, dried with sodium sulfate, filtered and evaporated. Purification by chromatography ($SiO_2$, heptane:ethylacetate=100:0 to 1:1) afforded the title product (21.96 g, 72%) which was obtained as a yellow solid. MS: m/e=237.1 [M+H]+.

bi) [3-(5-Fluoro-pyridin-2-yl)-isoxazol-4-yl]-methanol

To a solution of 3-(5-fluoro-pyridin-2-yl)-isoxazole-4-carboxylic acid ethyl ester (1.0 g, 4.23 mmol) in THF (52 mL) was added portionwise lithiumaluminiumhydride (89 mg, 2.33 mmol) at 0° C. and the reaction mixture was stirred at room temperature for 1 h. The mixture was then cooled to 0° C. and water (88 µL) added followed by sodium hydroxide (15% solution, 88 □L) and then again water (264 µL) and the mixture then stirred overnight at room temperature. The precipitate was then filtered off and washed with THF. The combined washings and filtrate were then evaporated. Purification by chromatography ($SiO_2$, heptane:ethyl acetate=100:0 to 1:1) afforded the title compound (249 mg, 30%) which was obtained as a light yellow solid. MS: m/e=195.1 [M+H]+.

Or alternatively via bii) 3-(5-Fluoro-pyridin-2-yl)-isoxazole-4-carboxylic acid

As described for example 112a, 3-(5-fluoro-pyridin-2-yl)-isoxazole-4-carboxylic acid ethyl ester (1.0 g, 4.23 mmol) was converted, instead of 5-[3-(4-chloro-phenyl)-isoxazol-4-ylmethoxy]-pyrazine-2-carboxylic acid methyl ester, to the title compound (587 mg, 67%) which was obtained as a dark brown solid. MS: m/e=207.1 [M−H]−.

biii) [3-(5-Fluoro-pyridin-2-yl)-isoxazol-4-yl]-methanol

As described for example 114g, 3-(5-fluoro-pyridin-2-yl)-isoxazole-4-carboxylic acid (562 mg, 2.7 mmol) was converted, instead of 5-methyl-3-pyrimidin-4-yl-isoxazole-4-carboxylic acid, to the title compound (367 mg, 70%) which was obtained as an off white solid. MS: m/e=195.2 [M+H]+.

c) 3-Chloro-6-[3-(5-fluoro-pyridin-2-yl)-isoxazol-4-ylmethoxy]-pyridazine

As described for example 48e, [3-(5-fluoro-pyridin-2-yl)-isoxazol-4-yl]-methanol (1.0 g, 5.15 mmol) was converted, instead of [3-(3-fluoro-phenyl)-5-methyl-isoxazol-4-yl]-methanol, to the title compound (1.03 g, 65%) which was obtained as a white solid. MS: m/e=307.1 [M+H]+.

d) 6-[3-(5-Fluoro-pyridin-2-yl)-isoxazol-4-ylmethoxy]-pyridazine-3-carboxylic acid ethyl ester As described for example 49, 3-chloro-6-[3-(5-fluoro-pyridin-2-yl)-isoxazol-4-ylmethoxy]-pyridazine (1.0 g, 3.26 mmol) was converted, instead of 3-chloro-6-[3-(3-fluoro-phenyl)-5-methyl-isoxazol-4-ylmethoxy]-pyridazine, to the title compound (348 mg, 31%) which was obtained as a white solid. MS: m/e=345.0 [M+H]+.

e) 6-[3-(5-Fluoro-pyridin-2-yl)-isoxazol-4-ylmethoxy]-pyridazine-3-carboxylic acid As described for example 112a, 6-[3-(5-fluoro-pyridin-2-yl)-isoxazol-4-ylmethoxy]-pyridazine-3-carboxylic acid ethyl ester (405 mg, 1.18 mmol) was converted, instead of 5-[3-(4-chloro-phenyl)-isoxazol-4-ylmethoxy]-pyrazine-2-carboxylic acid methyl ester, to the title compound (349 mg, 94%) which was obtained as an off white solid. MS: m/e=315.1 [M−H]−.

f) 6-[3-(5-Fluoro-pyridin-2-yl)-isoxazol-4-ylmethoxy]-pyridazine-3-carboxylic acid (2-hydroxy-1,1-dimethyl-ethyl)-amide As described for example 112b, 6-[3-(5-fluoro-pyridin-2-yl)-isoxazol-4-ylmethoxy]-pyridazine-3-carboxylic acid (79 mg, 0.25 mmol) was converted, instead of 6-[3-(5-fluoro-pyridin-2-yl)-5-methyl-isoxazol-4-ylmethoxy]-pyridazine-3-carboxylic acid, to the title compound (29 mg, 30%) which was obtained as a light yellow solid. MS: m/e=388.2 [M+H]+.

The invention claimed is:
1. A compound of formula I

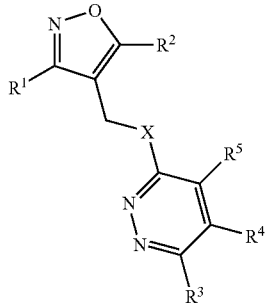

wherein
X is O or NH;
$R^1$ is phenyl, pyridinyl, or pyrimidinyl each optionally substituted with one, two or three halo,
$R^2$ is $C_{1-4}$alkyl, H or $C_{1-4}$haloalkyl;
$R^3$, $R^4$, and $R^5$ each are independently
H,
$C_{1-7}$alkyl, optionally substituted with one or more halo, cyano, or hydroxy,
$C_{1-7}$alkoxy, optionally substituted with one or more halo,
CN,
halo,
$NO_2$,
—C(O)—$R^a$, wherein $R^a$ is hydroxy, $C_{1-7}$alkoxy, $C_{1-7}$alkyl, phenoxy or phenyl,
—$NR^bR^c$, wherein $R^b$ and $R^c$ are each independently
hydrogen,
$C_{1-7}$alkyl,
—C(O)$C_{1-7}$alkyl, optionally substituted with one or more halo,
—C(O)(CH$_2$)$_m$—O—$C_{1-7}$alkyl, wherein m is 0, 1, 2, 3, 4, 5 or 6,
—C(O)C(O)O$C_{1-7}$-alkyl,
—C(O)CH$_2$C(O)O$C_{1-7}$-alkyl,
—C(O)$R^i$, wherein $R^i$ is phenyl or 5- to 6-membered heteroaryl, each optionally substituted with one or more E,
—C(O)—$C_{3-7}$cycloalkyl, optionally substituted with one or more B,
—C(O)—$R^{ii}$, wherein $R^{ii}$ is 3- to 7-membered heterocyclyl, optionally substituted by one or more A,
3- to 7-membered heterocyclyl, optionally substituted with one or more A,
5- or 6-membered heteroaryl, optionally substituted with one or more E,
—C(O)—$NR^dR^e$, wherein $R^d$ and $R^e$ are each independently
H,
$C_{1-7}$alkyl, optionally substituted with one or more halo, hydroxy, or cyano,
—(CH$_2$)$_t$—$C_{3-7}$cycloalkyl, optionally substituted by one or more B, and t is 0, 1, 2, 3 or 4,
—(CH$_2$)$_u$—O—$C_{1-7}$alkyl, wherein u is 2, 3, 4, 5 or 6,
—(CH$_2$)$_x$-heterocyclyl, wherein x is 0, 1, 2, 3 or 4, and wherein heterocyclyl is optionally substituted by one or more A $R^d$ and $R^e$ together with the nitrogen to which they are bound form a heterocyclyl moiety, optionally substituted with one or more A, or
$R^3$ together with the neighboring pyridazine-nitrogen form a 5-membered annelated aromatic ring with two additional ring nitrogen atoms, the annelated ring is optionally substituted by $R^f$, wherein $R^f$ is $C_{1-7}$-alkyl, —C(O)O$C_{1-7}$alkyl, —C(O)$C_{1-7}$alkyl, 5- or 6-membered heteroaryl or phenyl, each optionally substituted by one or more E,
A is hydroxy, oxo, $C_{1-7}$alkyl, $C_{1-7}$alkoxy, $C_{1-7}$haloalkyl, $C_{1-7}$hydroxyalkyl, halo, or CN,
B is halo, hydroxy, CN, $C_{1-4}$alkyl, or $C_{1-4}$haloalkyl,
E is halo, CN, $NO_2$, hydroxy, $C_{1-7}$alkyl, $C_{1-7}$alkoxy, $C_{1-7}$haloalkyl, $C_{1-7}$hydroxyalkyl, $C_{1-7}$cyanoalkyl, $C_{1-7}$haloalkoxy, or $C_{3-7}$cycloalkyl,
or a pharmaceutically acceptable salt thereof.

2. The compound of claim 1, wherein $R^4$ and $R^5$ are each independently H or $C_{1-7}$alkyl.

3. The compound of claim 2, wherein $R^4$ and $R^5$ are each independently H or Me.

4. The compound of claim 1, wherein $R^3$ is
H,
$C_{1-7}$alkyl, optionally substituted with one or more halo, cyano, or hydroxy,
$C_{1-7}$alkoxy, optionally substituted with one or more halo,
—C(O)—$R^a$, wherein $R^a$ is hydroxy, $C_{1-7}$alkoxy, or $C_{1-7}$alkyl,
—$NR^bR^c$, wherein $R^b$ and $R^c$ are each independently
hydrogen,
$C_{1-7}$alkyl,
—C(O)$C_{1-7}$alkyl, optionally substituted with one or more halo,
—C(O)(CH$_2$)$_m$—O—$C_{1-7}$alkyl, wherein m is 0 or 1,
—C(O)C(O)O$C_{1-7}$-alkyl,
—C(O)CH$_2$C(O)O$C_{1-7}$-alkyl,
—C(O)$R^i$, wherein $R^i$ is phenyl, furanyl, or isoxazolyl, each optionally substituted with one or more E,
—C(O)—$C_{3-7}$cycloalkyl, optionally substituted with one or more B,
—C(O)—$R^{ii}$, wherein $R^{ii}$ is tetrahydropyranyl, optionally substituted with one or more A,
pyrrolidinyl or morpholinyl, each optionally substituted with one or more A,
pyrazolyl, optionally substituted with one or more E,
—C(O)—$NR^dR^e$, wherein $R^d$ and $R^e$ are each independently
H,
$C_{1-7}$alkyl, optionally substituted with one or more halo, or hydroxy,
—(CH$_2$)$_t$—$C_{3-7}$cycloalkyl, optionally substituted by one or more B, and t is 0 or 1;
—(CH$_2$)$_2$—O—$C_{1-7}$alkyl,
tetrahydropyranyl, optionally substituted by one or more A
$R^d$ and $R^e$ together with the nitrogen to which they are bound form morpholinyl, or thiomorpholinyl, each optionally substituted with one or more A, or
$R^3$ together with the neighboring pyridazine-nitrogen form a 5-membered annelated aromatic ring with two additional ring nitrogen atoms, the annelated ring is optionally substituted by $R^f$, wherein $R^f$ is $C_{1-7}$-alkyl, —C(O)O$C_{1-7}$alkyl, or furanyl,
A is hydroxy, oxo, $C_{1-7}$alkyl, $C_{1-7}$alkoxy, $C_{1-7}$haloalkyl, $C_{1-7}$hydroxyalkyl, halo, or CN,
B is halo, hydroxy, CN, $C_{1-4}$alkyl, or $C_{1-4}$haloalkyl, E is halo, CN, NO$_2$, hydroxy, C$_{1-7}$alkyl, C$_{1-7}$alkoxy, C$_{1-7}$haloalkyl, C$_{1-7}$hydroxyalkyl, C$_{1-7}$cyanoalkyl, C$_{1-7}$haloalkoxy, or C$_{3-7}$cycloalkyl.

5. A compound of claim 1

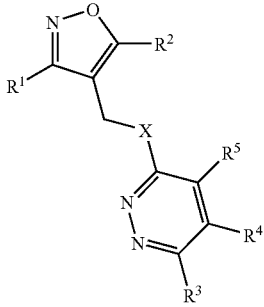

I wherein
X is O or NH;
R$^1$ is phenyl, pyridinyl, or pyrimidinyl, each optionally substituted with one halo;
R$^2$ is H or C$_{1-4}$alkyl;
R$^4$ is H or C$_{1-7}$alkyl;
R$^5$ is H or C$_{1-7}$alkyl;
R$^3$ is H,
  C$_{1-7}$alkyl,
  C$_{1-7}$alkoxy;
  halo,
  —C(O)—R$^a$, wherein R$^a$ is hydroxy, C$_{1-7}$alkoxy;
  —NR$^b$R$^c$, wherein R$^b$ and R$^c$ are each independently
    hydrogen,
    C$_{1-7}$alkyl,
    —C(O)C$_{1-7}$alkyl, optionally substituted with one or more halo,
    —C(O)(CH$_2$)$_m$—O—C$_{1-7}$alkyl, wherein m is 0 or 1;
    —C(O)C(O)OC$_{1-7}$-alkyl,
    —C(O)CH$_2$C(O)OC$_{1-7}$-alkyl,
    —C(O)R$^i$, wherein R$^i$ is phenyl or 5- to 6-membered heteroaryl, each optionally substituted with one E,
    —C(O)—C$_{3-7}$cycloalkyl;
    —C(O)—R$^{ii}$, wherein R$^{ii}$ is 3- to 7-membered heterocyclyl,
  3- to 7-membered heterocyclyl, optionally substituted with one A;
  5- or 6-membered heteroaryl;
  —C(O)—NR$^d$R$^e$, wherein R$^d$ and R$^e$ are each independently
    H,
    C$_{1-7}$alkyl, optionally substituted with one or more halo or hydroxy;
    —(CH$_2$)$_t$—C$_{3-7}$cycloalkyl, and t is 0, 1;
    —(CH$_2$)$_u$—O—C$_{1-7}$alkyl, wherein u is 2;
    -heterocyclyl;
    R$^d$ and R$^e$ together with the nitrogen to which they are bound form a heterocyclyl moiety, or
  R$^3$ together with the neighboring pyridazine-nitrogen form a 5-membered annelated aromatic ring with two additional ring nitrogen atoms, the annelated ring is optionally substituted by R$^f$, wherein R$^f$ is C$_{1-7}$-alkyl, —C(O)OC$_{1-7}$alkyl or 5- or 6-membered heteroaryl;
A is oxo;
E is C$_{1-7}$alkyl;
or a pharmaceutically acceptable salt thereof.

6. The compound of claim 1, where in R$^3$, R$^4$, and R$^5$ all are not hydrogen.

7. The compound of claim 1, selected from the group consisting of
3-chloro-6-(5-methyl-3-phenyl-isoxazol-4-ylmethoxy)-pyridazine,
3-bromo-6-(5-methyl-3-phenyl-isoxazol-4-ylmethoxy)-pyridazine,
3-methyl-6-(5-methyl-3-phenyl-isoxazol-4-ylmethoxy)-pyridazine,
6-(5-methyl-3-phenyl-isoxazol-4-ylmethoxy)-pyridazine-3-carboxylic acid ethyl ester,
6-(5-methyl-3-phenyl-isoxazol-4-ylmethoxy)-pyridazine-3-carboxylic acid (2-methoxy-ethyl)-amide,
6-(5-methyl-3-phenyl-isoxazol-4-ylmethoxy)-pyridazine-3-carboxylic acid isopropylamide,
6-(5-methyl-3-phenyl-isoxazol-4-ylmethoxy)-pyridazine-3-carboxylic acid cyclopropylamide,
6-(5-methyl-3-phenyl-isoxazol-4-ylmethoxy)-pyridazine-3-carboxylic acid (tetrahydro-pyran-4-yl)-amide,
6-(5-methyl-3-phenyl-isoxazol-4-ylmethoxy)-pyridazine-3-carboxylic acid (2-hydroxy-ethyl)-amide,
6-(5-methyl-3-phenyl-isoxazol-4-ylmethoxy)-pyridazine-3-carboxylic acid (2-hydroxy-1,1-dimethyl-ethyl)-amide, and
3-methoxy-6-(5-methyl-3-phenyl-isoxazol-4-yl-methoxy)-pyridazine.

8. The compound of claim 1, selected from the group consisting of
6-(5-methyl-3-phenyl-isoxazol-4-ylmethoxy)-pyridazin-3-ylamine,
N-[6-(5-methyl-3-phenyl-isoxazol-4-ylmethoxy)-pyridazin-3-yl]-acetamide,
N-[6-(5-methyl-3-phenyl-isoxazol-4-ylmethoxy)-pyridazin-3-yl]-isobutyramide,
cyclopropanecarboxylic acid [6-(5-methyl-3-phenyl-isoxazol-4-ylmethoxy)-pyridazin-3-yl]-amide,
cyclobutanecarboxylic acid [6-(5-methyl-3-phenyl-isoxazol-4-ylmethoxy)-pyridazin-3-yl]-amide,
tetrahydro-pyran-4-carboxylic acid [6-(5-methyl-3-phenyl-isoxazol-4-ylmethoxy)-pyridazin-3-yl]-amide,
1-[6-(5-methyl-3-phenyl-isoxazol-4-ylmethoxy)-pyridazin-3-yl]-pyrrolidin-2-one,
N-[6-(5-methyl-3-phenyl-isoxazol-4-ylmethoxy)-pyridazin-3-yl]-oxalamic acid methyl ester,
N-[6-(5-methyl-3-phenyl-isoxazol-4-ylmethoxy)-pyridazin-3-yl]-benzamide,
furan-2-carboxylic acid [6-(5-methyl-3-phenyl-isoxazol-4-ylmethoxy)-pyridazin-3-yl]-amide, and
isoxazole-5-carboxylic acid [6-(5-methyl-3-phenyl-isoxazol-4-ylmethoxy)-pyridazin-3-yl]-amide.

9. The compound of claim 1, selected from the group consisting of
[6-(5-methyl-3-phenyl-isoxazol-4-ylmethoxy)-pyridazin-3-yl]-carbamic acid ethyl ester,
4-[6-(5-methyl-3-phenyl-isoxazol-4-ylmethoxy)-pyridazin-3-yl]-morpholine,
methyl-[6-(5-methyl-3-phenyl-isoxazol-4-ylmethoxy)-pyridazin-3-yl]-amine,
dimethyl-[6-(5-methyl-3-phenyl-isoxazol-4-ylmethoxy)-pyridazin-3-yl]-amine,
3-(3,5-dimethyl-pyrazol-1-yl)-6-(5-methyl-3-phenyl-isoxazol-4-ylmethoxy)-pyridazine,
5-methyl-6-(5-methyl-3-phenyl-isoxazol-4-ylmethoxy)-pyridazine-3-carboxylic acid ethyl ester,
3-chloro-4-methyl-6-(5-methyl-3-phenyl-isoxazol-4-yl-methoxy)-pyridazine, 4-methyl-6-(5-methyl-3-phenyl-isoxazol-4-ylmethoxy)-pyridazine-3-carboxylic acid ethyl ester,
4-methyl-6-(5-methyl-3-phenyl-isoxazol-4-ylmethoxy)-pyridazine-3-carboxylic acid (tetrahydro-pyran-4-yl)-amide,
4-methyl-6-(5-methyl-3-phenyl-isoxazol-4-ylmethoxy)-pyridazine-3-carboxylic acid cyclopropylamide, and
4-methyl-6-(5-methyl-3-phenyl-isoxazol-4-ylmethoxy)-pyridazine-3-carboxylic acid isopropylamide.

10. The compound of claim 1, selected from the group consisting of
6-[3-(3-fluoro-phenyl)-5-methyl-isoxazol-4-ylmethoxy]-pyridazine-3-carboxylic acid ethyl ester,
6-[3-(3-fluoro-phenyl)-5-methyl-isoxazol-4-ylmethoxy]-pyridazine-3-carboxylic acid methylamide,
6-[3-(3-fluoro-phenyl)-5-methyl-isoxazol-4-ylmethoxy]-pyridazine-3-carboxylic acid ethylamide,
6-[3-(3-fluoro-phenyl)-5-methyl-isoxazol-4-ylmethoxy]-pyridazine-3-carboxylic acid (2-hydroxy-ethyl)-amide,
6-[3-(3-fluoro-phenyl)-5-methyl-isoxazol-4-ylmethoxy]-pyridazine-3-carboxylic acid isopropylamide,
6-[3-(3-fluoro-phenyl)-5-methyl-isoxazol-4-ylmethoxy]-pyridazine-3-carboxylic acid cyclopropylamide,
3-chloro-6-[3-(4-fluoro-phenyl)-5-methyl-isoxazol-4-ylmethoxy]-pyridazine,
6-[3-(4-fluoro-phenyl)-5-methyl-isoxazol-4-ylmethoxy]-pyridazine-3-carboxylic acid ethyl ester,
6-[3-(4-fluoro-phenyl)-5-methyl-isoxazol-4-ylmethoxy]-pyridazine-3-carboxylic acid cyclopropylmethyl-amide,
6-[3-(4-fluoro-phenyl)-5-methyl-isoxazol-4-ylmethoxy]-pyridazine-3-carboxylic acid (2,2,2-trifluoro-ethyl)-amide, and
6-[3-(4-fluoro-phenyl)-5-methyl-isoxazol-4-ylmethoxy]-pyridazine-3-carboxylic acid isopropylamide.

11. The compound of claim 1, selected from the group consisting of
6-[3-(4-fluoro-phenyl)-5-methyl-isoxazol-4-ylmethoxy]-pyridazine-3-carboxylic acid cyclopropylamide,
6-[3-(4-fluoro-phenyl)-5-methyl-isoxazol-4-ylmethoxy]-pyridazine-3-carboxylic acid (tetrahydro-pyran-4-yl)-amide,
(1,1-dioxo-1λ6-thiomorpholin-4-yl)-{6-[3-(4-fluoro-phenyl)-5-methyl-isoxazol-4-ylmethoxy]-pyridazin-3-yl}-methanone,
6-(5-methyl-3-phenyl-isoxazol-4-ylmethoxy)-[1,2,4]triazolo[4,3-b]pyridazine,
6-(5-methyl-3-phenyl-isoxazol-4-ylmethoxy)-[1,2,4]triazolo[4,3-b]pyridazine-3-carboxylic acid ethyl ester,
6-[3-(4-fluoro-phenyl)-5-methyl-isoxazol-4-ylmethoxy]-[1,2,4]triazolo[4,3-b]pyridazine,
3-chloro-6-(5-methyl-3-pyridin-2-yl-isoxazol-4-ylmethoxy)-pyridazine,
6-(5-methyl-3-pyridin-2-yl-isoxazol-4-ylmethoxy)-pyridazine-3-carboxylic acid ethyl,
6-(5-methyl-3-pyridin-2-yl-isoxazol-4-ylmethoxy)-pyridazine-3-carboxylic acid (tetrahydro-pyran-4-yl)-amide,
6-(5-methyl-3-pyridin-2-yl-isoxazol-4-ylmethoxy)-pyridazine-3-carboxylic acid isopropylamide, and
[6-(5-methyl-3-pyridin-2-yl-isoxazol-4-ylmethoxy)-pyridazin-3-yl]-morpholin-4-yl-methanone.

12. The compound of claim 1, selected from the group consisting of
6-(5-methyl-3-pyridin-2-yl-isoxazol-4-ylmethoxy)-pyridazine-3-carboxylic acid cyclopropylamide,
6-(5-methyl-3-pyridin-2-yl-isoxazol-4-ylmethoxy)-pyridazine-3-carboxylic acid (2,2,2-trifluoro-ethyl)-amide,
(1,1-dioxo-1λ6-thiomorpholin-4-yl)-[6-(5-methyl-3-pyridin-2-yl-isoxazol-4-ylmethoxy)-pyridazin-3-yl]-methanone,
6-(5-methyl-3-pyridin-2-yl-isoxazol-4-ylmethoxy)-pyridazine-3-carboxylic acid cyclopropylmethyl-amide,
6-(5-methyl-3-pyridin-2-yl-isoxazol-4-ylmethoxy)-pyridazine-3-carboxylic acid (2-hydroxy-ethyl)-amide,
6-(5-methyl-3-pyridin-2-yl-isoxazol-4-ylmethoxy)-pyridazine-3-carboxylic acid methylamide,
6-(5-methyl-3-pyridin-2-yl-isoxazol-4-ylmethoxy)-pyridazine-3-carboxylic acid ethylamide,
[6-(5-methyl-3-pyridin-2-yl-isoxazol-4-ylmethoxy)-pyridazin-3-yl]-thiomorpholin-4-yl-methanone,
6-(5-methyl-3-pyridin-2-yl-isoxazol-4-ylmethoxy)-pyridazine-3-carboxylic acid (2-hydroxy-1,1-dimethyl-ethyl)-amide,
6-(5-methyl-3-pyridin-2-yl-isoxazol-4-ylmethoxy)-pyridazine-3-carboxylic acid (2-methoxy-ethyl)-amide, and
6-(5-methyl-3-pyridin-4-yl-isoxazol-4-ylmethoxy)-pyridazine-3-carboxylic acid (2-hydroxy-ethyl)-amide.

13. The compound of claim 1, selected from the group consisting of
6-(5-methyl-3-pyridin-4-yl-isoxazol-4-ylmethoxy)-pyridazine-3-carboxylic acid methylamide,
6-(5-methyl-3-pyridin-4-yl-isoxazol-4-ylmethoxy)-pyridazine-3-carboxylic acid ethylamide,
3-chloro-6-[3-(5-fluoro-pyridin-2-yl)-5-methyl-isoxazol-4-ylmethoxy]-pyridazine,
6-[3-(5-fluoro-pyridin-2-yl)-5-methyl-isoxazol-4-ylmethoxy]-pyridazine-3-carboxylic acid ethyl ester,
6-[3-(5-fluoro-pyridin-2-yl)-5-methyl-isoxazol-4-ylmethoxy]-pyridazine-3-carboxylic acid (2-hydroxy-1,1-dimethyl-ethyl)-amide,
6-[3-(5-chloro-pyridin-2-yl)-5-methyl-isoxazol-4-ylmethoxy]-pyridazine-3-carboxylic acid,
6-(5-methyl-3-pyrimidin-4-yl-isoxazol-4-ylmethoxy)-pyridazine-3-carboxylic acid (2-hydroxy-ethyl)-amide,
6-(5-methyl-3-pyrimidin-4-yl-isoxazol-4-ylmethoxy)-pyridazine-3-carboxylic acid (2-hydroxy-1,1-dimethyl-ethyl)-amide,
6-{[3-(3-fluoro-phenyl)-5-methyl-isoxazol-4-ylmethyl]-amino}-pyridazine-3-carboxylic acid cyclopropylamide,
6-{[3-(3-fluoro-phenyl)-5-methyl-isoxazol-4-ylmethyl]-amino}-pyridazine-3-carboxylic acid cyclopropylmethyl-amide, and
6-{[3-(3-fluoro-phenyl)-5-methyl-isoxazol-4-ylmethyl]-amino}-pyridazine-3-carboxylic acid (2,2,2-trifluoro-ethyl)-amide.

14. The compound of claim 1, selected from the group consisting of
6-{[3-(5-chloro-pyridin-2-yl)-5-methyl-isoxazol-4-ylmethyl]-amino}-pyridazine-3-carboxylic acid (2-hydroxy-1,1-dimethyl-ethyl)-amide,
6-[3-(4-fluoro-phenyl)-isoxazol-4-ylmethoxy]-pyridazine-3-carboxylic acid ethyl ester,
6-[3-(4-fluoro-phenyl)-isoxazol-4-ylmethoxy]-pyridazine-3-carboxylic acid isopropylamide,
6-[3-(4-fluoro-phenyl)-isoxazol-4-ylmethoxy]-pyridazine-3-carboxylic acid (tetrahydro-pyran-4-yl)-amide,
6-(3-pyridin-2-yl-isoxazol-4-ylmethoxy)-pyridazine-3-carboxylic acid isopropylamide, 6-(3-pyridin-2-yl-isoxazol-4-ylmethoxy)-pyridazine-3-carboxylic acid cyclopropylamide, 6-(3-pyridin-2-yl-isoxazol-4-ylmethoxy)-pyridazine-3-carboxylic acid cyclopropylmethyl-amide, 6-(3-pyridin-2-yl-isoxazol-4-ylmethoxy)-pyridazine-3-carboxylic acid (2,2,2-trifluoro-ethyl)-amide, and 6-[3-(5-fluoro-pyridin-2-yl)-isoxazol-4-ylmethoxy]-pyridazine-3-carboxylic acid (2-hydroxy-1,1-dimethyl-ethyl)-amide.

15. A pharmaceutical composition comprising a therapeutically effective amount of a compound of formula I

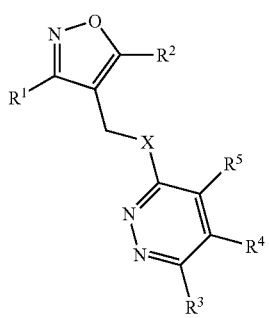

I wherein

X is O or NH;

$R^1$ is phenyl, pyridinyl, or pyrimidinyl each optionally substituted with one, two or three halo, $R^2$ is $C_{1-4}$alkyl, H or $C_{1-4}$haloalkyl;

$R^3$, $R^4$, and $R^5$ each are independently

H, $C_{1-7}$alkyl, optionally substituted with one or more halo, cyano, or hydroxy, $C_{1-7}$alkoxy, optionally substituted with one or more halo,

CN, halo, $NO_2$,

—C(O)—$R^a$, wherein $R^a$ is hydroxy, $C_{1-7}$alkoxy, $C_{1-7}$alkyl, phenoxy or phenyl, —$NR^bR^c$, wherein $R^b$ and $R^c$ are each independently hydrogen, $C_{1-7}$alkyl, —C(O)$C_{1-7}$alkyl, optionally substituted with one or more halo, —C(O)(CH$_2$)$_m$—O—$C_{1-7}$alkyl, wherein m is 0, 1, 2, 3, 4, 5 or 6, —C(O)C(O)O$C_{1-7}$-alkyl, —C(O)CH$_2$C(O)O$C_{1-7}$-alkyl, —C(O)$R^i$, wherein $R^i$ is phenyl or 5- to 6-membered heteroaryl, each optionally substituted with one or more E, —C(O)—$C_{3-7}$cycloalkyl, optionally substituted with one or more B, —C(O)—$R^i$, wherein $R^i$ is 3- to 7-membered heterocyclyl, optionally substituted by one or more A, 3- to 7-membered heterocyclyl, optionally substituted with one or more A, 5- or 6-membered heteroaryl, optionally substituted with one or more E, —C(O)—$NR^dR^e$, wherein $R^d$ and $R^e$ are each independently

H, $C_{1-7}$alkyl, optionally substituted with one or more halo, hydroxy, or cyano, —(CH$_2$)$_t$—$C_{3-7}$cycloalkyl, optionally substituted by one or more B, and t is 0, 1, 2, 3 or 4, —(CH$_2$)$_u$—O—$C_{1-7}$alkyl, wherein u is 2, 3, 4, 5 or 6, —(CH$_2$)$_x$-heterocyclyl, wherein x is 0, 1, 2, 3 or 4, and wherein heterocyclyl is optionally substituted by one or more A $R^d$ and $R^e$ together with the nitrogen to which they are bound form a heterocyclyl moiety, optionally substituted with one or more A, or $R^3$ together with the neighboring pyridazine-nitrogen form a 5-membered annelated aromatic ring with two additional ring nitrogen atoms, the annelated ring is optionally substituted by $R^f$, wherein $R^f$ is $C_{1-7}$-alkyl, —C(O)O$C_{1-7}$alkyl, —C(O)$C_{1-7}$alkyl, 5- or 6-membered heteroaryl or phenyl, each optionally substituted by one or more E, A is hydroxy, oxo, $C_{1-7}$alkyl, $C_{1-7}$alkoxy, $C_{1-7}$haloalkyl, $C_{1-7}$hydroxyalkyl, halo, or CN, B is halo, hydroxy, CN, $C_{1-4}$alkyl, or $C_{1-4}$haloalkyl, E is halo, CN, $NO_2$, hydroxy, $C_{1-7}$alkyl, $C_{1-7}$alkoxy, $C_{1-7}$haloalkyl, $C_{1-7}$hydroxyalkyl, $C_{1-7}$cyanoalkyl, $C_{1-7}$haloalkoxy, or $C_{3-7}$cycloalkyl, or a pharmaceutically acceptable salt thereof and a pharmaceutically acceptable carrier.

* * * * *